US00RE46543E

(19) United States
(12) Reissued Patent
Trevor-Wilson et al.

(10) Patent Number: US RE46,543 E
(45) Date of Reissued Patent: Sep. 12, 2017

(54) BREATHABLE GAS APPARATUS WITH HUMIDIFIER

(71) Applicant: ResMed Limited

(72) Inventors: Duncan Lovel Trevor-Wilson, Sydney (AU); Perry David Lithgow, Sydney (AU); Alexander Virr, Gosford (AU); Andrew Roderick Bath, Sydney (AU); Michael Thomas Janiak, Sydney (AU); Dan Kao, Sydney (AU); Jim Saada, Sydney (AU)

(73) Assignee: ResMed Limited, Bella Vista (AU)

(21) Appl. No.: 15/079,098

(22) Filed: Mar. 24, 2016

Related U.S. Patent Documents

Reissue of:
(64) Patent No.: 8,042,535
Issued: Oct. 25, 2011
Appl. No.: 13/080,300
Filed: Apr. 5, 2011

U.S. Applications:
(63) Continuation of application No. 10/533,940, filed as application No. PCT/AU2004/000810 on Jun. 21, 2004, now Pat. No. 8,006,691.

(30) Foreign Application Priority Data

| | | |
|---|---|---|
| Jun. 20, 2003 | (AU) | 2003903139 |
| Sep. 22, 2003 | (AU) | 2003905136 |
| Feb. 27, 2004 | (AU) | 2004901008 |

(51) Int. Cl.
*A62B 9/00* (2006.01)
*A61M 16/00* (2006.01)
(Continued)

(52) U.S. Cl.
CPC ..... *A61M 16/162* (2013.01); *A61M 16/00* (2013.01); *A61M 16/0003* (2014.02);
(Continued)

(58) Field of Classification Search
CPC ..... A61M 16/00; A61M 16/105; A61M 16/0057; A61M 16/0066; A61M 16/16;
(Continued)

(56) References Cited

U.S. PATENT DOCUMENTS

| | | | |
|---|---|---|---|
| 1,085,833 | A | 2/1914 | Wilson |
| 1,974,843 | A | 9/1934 | Blashfield |

(Continued)

FOREIGN PATENT DOCUMENTS

| | | |
|---|---|---|
| AU | 200065475 | 4/2001 |
| CA | 2099665 | 7/1992 |

(Continued)

OTHER PUBLICATIONS

RESMED Sullivan Humidaire™ User Instruction Manual (1998).*

(Continued)

*Primary Examiner* — Jeffrey R Jastrzab
(74) *Attorney, Agent, or Firm* — Nixon & Vanderhye P.C.

(57) ABSTRACT

Apparatus for treatment of obstructive sleep apnea includes a CPAP device and a detachable humidifier. The humidifier includes a tank that is removably insertable into a humidifier base. A sealed air flow path from the CPAP device and through the water tank is established when the water tank is placed in the humidifier base.

30 Claims, 31 Drawing Sheets

(51) Int. Cl.

| | |
|---|---|
| ***F22B 1/00*** | (2006.01) |
| ***A61M 16/16*** | (2006.01) |
| ***A61M 16/08*** | (2006.01) |
| ***A61M 16/10*** | (2006.01) |
| *B01F 3/04* | (2006.01) |
| *B29L 31/00* | (2006.01) |

(52) U.S. Cl.

CPC .... *A61M 16/0051* (2013.01); *A61M 16/0057* (2013.01); *A61M 16/0816* (2013.01); *A61M 16/0875* (2013.01); *A61M 16/105* (2013.01); *A61M 16/109* (2014.02); *A61M 16/16* (2013.01); *A61M 16/0066* (2013.01); *A61M 2205/123* (2013.01); *A61M 2205/14* (2013.01); *A61M 2205/3303* (2013.01); *A61M 2205/3306* (2013.01); *A61M 2205/42* (2013.01); *A61M 2205/50* (2013.01); *A61M 2205/502* (2013.01); *A61M 2205/52* (2013.01); *A61M 2205/6063* (2013.01); *A61M 2206/16* (2013.01); *A61M 2230/005* (2013.01); *A61M 2230/46* (2013.01); *A62B 9/003* (2013.01); *B01F 3/0446* (2013.01); *B01F 2003/04872* (2013.01); *B01F 2215/0091* (2013.01); *B29L 2031/753* (2013.01)

(58) Field of Classification Search

CPC ..... A61M 16/162; A61M 16/109; A61M 16/0003; A61M 16/0875; A61M 16/0816; A61M 16/0051; A61M 2205/14; A61M 2205/42; A61M 2205/50; A61M 2205/502; A61M 2205/52; A61M 2205/6063; A61M 2205/36; A61M 2206/16; A61M 2205/3303; A61M 2230/005; A61M 2205/3306; A61M 2230/46; A62B 9/003; B29L 2031/753; B01F 3/0446; B01F 2003/04872; B01F 2215/0091

USPC ..... 261/130, 142, DIG. 65, 129, 154, 119.1, 261/72.1; 128/200.24, 203.12–205.26; 122/4 A, 4 R, 5.51, 7 B, 13.01, 13.3–19.2, 122/33, 487

See application file for complete search history.

(56) References Cited

U.S. PATENT DOCUMENTS

| | | | |
|---|---|---|---|
| RE19,826 | E | 1/1936 | Aisenstein |
| 2,220,669 | A | 11/1940 | Allen |
| 2,598,978 | A | 6/1952 | De Martin |
| 2,780,708 | A | 2/1957 | Glynn et al. |
| 2,945,619 | A | 7/1960 | Ballard |
| 3,171,353 | A | 3/1965 | McMahan |
| 3,316,910 | A | 5/1967 | Davis |
| 3,584,401 | A | 6/1971 | Cryer et al. |
| 3,612,710 | A | 10/1971 | Mount |
| 3,620,638 | A | 11/1971 | Kaye et al. |
| 3,638,926 | A | 2/1972 | Melville et al. |
| 3,659,604 | A | 5/1972 | Melville et al. |
| 3,690,317 | A | 9/1972 | Millman |
| 3,806,102 | A | 4/1974 | Valenta et al. |
| 3,864,440 | A | 2/1975 | Giocoechea |
| 3,954,920 | A | 5/1976 | Heath |
| 4,025,590 | A | 5/1977 | Igich |
| 4,037,994 | A | 7/1977 | Bird |
| 4,051,205 | A | 9/1977 | Grant |
| 4,060,576 | A | 11/1977 | Grant |
| 4,098,853 | A | 7/1978 | Brown et al. |
| 4,105,372 | A | 8/1978 | Mishina et al. |
| 4,152,379 | A | 5/1979 | Suhr |
| 4,171,190 | A | 10/1979 | Hudson |
| 4,222,971 | A | 9/1980 | Eilert |
| 4,229,142 | A | 10/1980 | Le Dall et al. |
| 4,237,080 | A | 12/1980 | Elliott |
| 4,243,396 | A | 1/1981 | Cronenberg |
| 4,336,798 | A | 6/1982 | Beran |
| 4,351,327 | A | 9/1982 | Rinne et al. |
| 4,383,800 | A | 5/1983 | Becker et al. |
| 4,523,896 | A | 6/1985 | Lhenry et al. |
| 4,532,088 | A | 7/1985 | Miller |
| 4,576,616 | A | 3/1986 | Mottram et al. |
| 4,588,425 | A | 5/1986 | Usry et al. |
| 4,621,632 | A | 11/1986 | Bartels et al. |
| 4,629,590 | A | 12/1986 | Bagwell |
| 4,644,790 | A | 2/1987 | Mizoguchi |
| 4,657,713 | A | 4/1987 | Miller |
| 4,676,237 | A | 6/1987 | Wood et al. |
| 4,686,354 | A | 8/1987 | Makin |
| 4,753,758 | A | 6/1988 | Miller |
| 4,767,576 | A | 8/1988 | Bagwell |
| 4,789,388 | A | 12/1988 | Nishibata |
| 4,799,287 | A | 1/1989 | Belanger |
| 4,802,819 | A | 2/1989 | Bevington et al. |
| 4,807,616 | A | 2/1989 | Adahan |
| 4,819,625 | A | 4/1989 | Howe |
| 4,823,787 | A | 4/1989 | Adahan |
| 4,838,258 | A | 6/1989 | Dryden et al. |
| 4,870,961 | A | 10/1989 | Barnard |
| 4,906,417 | A | 3/1990 | Gentry |
| 4,913,140 | A | 4/1990 | Orec et al. |
| 4,921,642 | A | 5/1990 | LaTorraca |
| 4,926,856 | A | 5/1990 | Cambio et al. |
| 4,941,469 | A | 7/1990 | Adahan |
| 4,943,704 | A | 7/1990 | Rabenau |
| 4,946,348 | A | 8/1990 | Yapp |
| 4,953,546 | A | 9/1990 | Blackmer et al. |
| 4,973,234 | A | 11/1990 | Swenson |
| 4,993,411 | A | 2/1991 | Callaway |
| 5,061,405 | A | 10/1991 | Stanek et al. |
| 5,080,093 | A | 1/1992 | Raabe |
| 5,086,766 | A | 2/1992 | Beacham |
| 5,097,424 | A | 3/1992 | Ginevri et al. |
| 5,127,800 | A | 7/1992 | Hyll et al. |
| 5,199,009 | A | 3/1993 | Svast |
| 5,231,979 | A | 8/1993 | Rose et al. |
| 5,231,981 | A | 8/1993 | Schreiber |
| 5,237,987 | A | 8/1993 | Anderson et al. |
| 5,259,370 | A | 11/1993 | Howe |
| 5,271,391 | A | 12/1993 | Graves |
| 5,329,939 | A | 7/1994 | Howe |
| 5,339,825 | A | 8/1994 | McNaughton et al. |
| 5,391,063 | A | 2/1995 | Hantle et al. |
| 5,443,061 | A | 8/1995 | Champain et al. |
| 5,445,143 | A | 8/1995 | Sims |
| 5,474,112 | A | 12/1995 | Carola |
| 5,482,031 | A | 1/1996 | Lambert |
| 5,483,616 | A | 1/1996 | Chiu et al. |
| 5,537,997 | A | 7/1996 | Mechlenburg et al. |
| 5,551,419 | A | 9/1996 | Froehlich et al. |
| 5,558,084 | A | 9/1996 | Daniell et al. |
| 5,564,415 | A | 10/1996 | Dobson et al. |
| 5,573,713 | A | 11/1996 | Tomasiak et al. |
| 5,577,496 | A | 11/1996 | Blackwood et al. |
| 5,588,423 | A | 12/1996 | Smith |
| 5,598,837 | A | 2/1997 | Sirianne, Jr. et al. |
| 5,645,531 | A | 7/1997 | Thompson et al. |
| 5,651,775 | A | 7/1997 | Walker et al. |
| 5,655,522 | A | 8/1997 | Mechlenburg et al. |
| 5,673,687 | A | 10/1997 | Dobson et al. |
| 5,682,289 | A | 10/1997 | Schwegler et al. |
| 5,735,017 | A | 4/1998 | Barnes et al. |
| 5,794,219 | A | 8/1998 | Brown |
| 5,822,715 | A | 10/1998 | Worthington et al. |
| 5,828,943 | A | 10/1998 | Brown |
| 5,832,448 | A | 11/1998 | Brown |
| 5,844,862 | A | 12/1998 | Cocatre-Zilgien |
| 5,848,592 | A | 12/1998 | Sibley |
| 5,865,171 | A | 2/1999 | Cinquin |
| 5,870,283 | A | 2/1999 | Maeda et al. |
| 5,878,743 | A | 3/1999 | Zdrojkowski et al. |

(56) References Cited

U.S. PATENT DOCUMENTS

| | | | |
|---|---|---|---|
| 5,879,163 | A | 3/1999 | Brown et al. |
| 5,887,133 | A | 3/1999 | Brown et al. |
| 5,888,053 | A | 3/1999 | Kobayashi et al. |
| 5,895,595 | A | 4/1999 | Haden |
| 5,897,493 | A | 4/1999 | Brown |
| 5,899,855 | A | 5/1999 | Brown |
| 5,913,310 | A | 6/1999 | Brown |
| 5,916,493 | A | 6/1999 | Miller et al. |
| 5,918,603 | A | 7/1999 | Brown |
| 5,928,177 | A | 7/1999 | Brugger et al. |
| 5,933,136 | A | 8/1999 | Brown |
| 5,940,801 | A | 8/1999 | Brown |
| 5,943,473 | A | 8/1999 | Levine |
| 5,951,300 | A | 9/1999 | Brown |
| 5,956,501 | A | 9/1999 | Brown |
| 5,960,403 | A | 9/1999 | Brown |
| 5,985,559 | A | 11/1999 | Brown |
| 5,997,476 | A | 12/1999 | Brown |
| 6,000,396 | A | 12/1999 | Melker et al. |
| D419,658 | S | 1/2000 | Matchett et al. |
| 6,023,686 | A | 2/2000 | Brown |
| 6,032,119 | A | 2/2000 | Brown et al. |
| 6,050,260 | A | 4/2000 | Daniell et al. |
| 6,052,511 | A | 4/2000 | Birdsell |
| 6,101,478 | A | 8/2000 | Brown |
| 6,109,865 | A | 8/2000 | Ishikawa |
| 6,129,524 | A | 10/2000 | Woollenweber et al. |
| 6,131,571 | A | 10/2000 | Lampotang et al. |
| 6,135,432 | A | 10/2000 | Hebblewhite et al. |
| 6,144,837 | A | 11/2000 | Quy |
| 6,152,132 | A | 11/2000 | Psaros |
| 6,158,978 | A | 12/2000 | Norbury, Jr. |
| 6,161,095 | A | 12/2000 | Brown |
| 6,185,095 | B1 | 2/2001 | Helot et al. |
| 6,186,140 | B1 | 2/2001 | Hoague |
| 6,189,870 | B1 | 2/2001 | Withall |
| 6,192,883 | B1 | 2/2001 | Miller |
| 6,202,991 | B1 | 3/2001 | Coniglio et al. |
| 6,210,116 | B1 | 4/2001 | Kuczaj et al. |
| 6,213,119 | B1 | 4/2001 | Brydon et al. |
| 6,216,691 | B1 | 4/2001 | Kenyon et al. |
| 6,257,171 | B1 | 7/2001 | Rivard |
| 6,275,652 | B1 | 8/2001 | Chauviaux |
| 6,279,574 | B1 | 8/2001 | Richardson et al. |
| 6,308,706 | B1 | 10/2001 | Lammers et al. |
| 6,314,237 | B1 | 11/2001 | Glucksman |
| 6,332,462 | B1 | 12/2001 | Krohn |
| 6,338,473 | B1 | 1/2002 | Hebblewhite et al. |
| 6,340,288 | B1 | 1/2002 | Hulkkonen et al. |
| 6,349,724 | B1 | 2/2002 | Burton et al. |
| D454,393 | S | 3/2002 | Lynch et al. |
| 6,397,841 | B1 | 6/2002 | Kenyon et al. |
| 6,398,197 | B1 | 6/2002 | Dickinson et al. |
| 6,435,180 | B1 | 8/2002 | Hewson et al. |
| 6,471,493 | B2 | 10/2002 | Choi et al. |
| D467,335 | S | 12/2002 | Lithgow et al. |
| D468,011 | S | 12/2002 | Lynch et al. |
| D468,017 | S | 12/2002 | McCombs |
| 6,514,053 | B2 | 2/2003 | Takura et al. |
| 6,543,449 | B1 | 4/2003 | Woodring et al. |
| 6,546,930 | B1 | 4/2003 | Emerson et al. |
| 6,554,260 | B1 | 4/2003 | Lipscombe et al. |
| 6,591,834 | B1 | 7/2003 | Colla et al. |
| 6,604,390 | B1 | 8/2003 | Nooner |
| 6,615,444 | B2 | 9/2003 | McGilll et al. |
| 6,622,724 | B1 | 9/2003 | Truitt et al. |
| 6,669,630 | B1 | 12/2003 | Joliat et al. |
| 6,672,300 | B1 | 1/2004 | Grant |
| 6,678,215 | B1 | 1/2004 | Treyz et al. |
| D487,311 | S | 3/2004 | Lithgow et al. |
| 6,718,974 | B1 | 4/2004 | Moberg |
| D493,520 | S | 7/2004 | Bertinetti et al. |
| D493,884 | S | 8/2004 | Virr et al. |
| 6,772,999 | B2 | 8/2004 | Lipscombe et al. |
| 6,775,882 | B2 | 8/2004 | Murphy et al. |
| D498,527 | S | 11/2004 | Virr et al. |
| 6,827,340 | B2 | 12/2004 | Austin et al. |
| 6,837,260 | B1 | 1/2005 | Kuehn |
| 6,874,771 | B2 | 4/2005 | Birdsell et al. |
| 6,896,478 | B2 | 5/2005 | Botros et al. |
| 6,910,483 | B2 | 6/2005 | Daly et al. |
| 6,918,389 | B2 | 7/2005 | Seakins et al. |
| 6,935,337 | B2 | 8/2005 | Virr et al. |
| 7,056,289 | B2 | 6/2006 | Kasper et al. |
| 7,089,930 | B2 | 8/2006 | Adams et al. |
| 7,096,864 | B1 | 8/2006 | Mayer et al. |
| 7,111,624 | B2 | 9/2006 | Thudor et al. |
| 7,128,729 | B2 | 10/2006 | Duchon et al. |
| 7,137,388 | B2 | 11/2006 | Virr et al. |
| 7,225,809 | B1 | 6/2007 | Bowen et al. |
| 7,413,173 | B2 | 8/2008 | DiMatteo et al. |
| 7,478,635 | B2 | 1/2009 | Wixey et al. |
| 7,614,398 | B2 | 11/2009 | Virr et al. |
| 7,616,871 | B2 | 11/2009 | Kramer |
| 7,677,246 | B2 | 3/2010 | Kepler et al. |
| 8,006,691 | B2 | 8/2011 | Trevor-Wilson et al. |
| 8,020,551 | B2 | 9/2011 | Virr |
| 8,028,693 | B2 | 10/2011 | Trevor-Wilson |
| 8,042,535 | B2 | 10/2011 | Kenyon |
| 8,091,547 | B2 | 1/2012 | Thudor et al. |
| RE44,453 | E | 8/2013 | Virr et al. |
| 8,550,072 | B2 | 10/2013 | Thudor et al. |
| 9,038,631 | B2 | 5/2015 | Bath et al. |
| 9,038,632 | B2 | 5/2015 | Crumblin et al. |
| 9,072,860 | B2 | 7/2015 | Lithgow et al. |
| 9,227,035 | B2 | 1/2016 | Crumblin et al. |
| 9,358,359 | B2 | 6/2016 | Lithgow et al. |
| 9,539,409 | B2 | 1/2017 | Crumblin et al. |
| 2001/0017134 | A1 | 8/2001 | Bahr |
| 2001/0050080 | A1 | 12/2001 | Seakins et al. |
| 2002/0020930 | A1 | 2/2002 | Austin et al. |
| 2002/0022973 | A1 | 2/2002 | Sun et al. |
| 2002/0056453 | A1 | 5/2002 | Klopp et al. |
| 2002/0129815 | A1 | 9/2002 | McPhee |
| 2002/0159897 | A1 | 10/2002 | Kegg et al. |
| 2003/0062045 | A1 | 4/2003 | Woodring et al. |
| 2003/0065308 | A1 | 4/2003 | Lebel et al. |
| 2003/0066526 | A1 | 4/2003 | Thudor et al. |
| 2003/0066530 | A1 | 4/2003 | Shahbazpour et al. |
| 2003/0076745 | A1 | 4/2003 | Chapman |
| 2003/0084900 | A1 | 5/2003 | LeClerc et al. |
| 2003/0115085 | A1 | 6/2003 | Satoh |
| 2003/0187525 | A1 | 10/2003 | Mann et al. |
| 2003/0208465 | A1 | 11/2003 | Yurko et al. |
| 2003/0230308 | A1 | 12/2003 | Linden |
| 2003/0236450 | A1 | 12/2003 | Kocinski |
| 2004/0035422 | A1 | 2/2004 | Truitt et al. |
| 2004/0055597 | A1 | 3/2004 | Virr et al. |
| 2004/0060559 | A1 | 4/2004 | Virr et al. |
| 2005/0005937 | A1 | 1/2005 | Farrugia et al. |
| 2005/0103339 | A1 | 5/2005 | Daly et al. |
| 2005/0217673 | A1 | 10/2005 | Daly et al. |
| 2006/0191531 | A1 | 8/2006 | Mayer |
| 2006/0237005 | A1 | 10/2006 | Virr et al. |
| 2007/0036662 | A1 | 2/2007 | Pensola et al. |
| 2007/0134085 | A1 | 6/2007 | Daly et al. |
| 2008/0072900 | A1 | 3/2008 | Kenyon et al. |
| 2009/0229606 | A1 | 9/2009 | Tang et al. |
| 2010/0192094 | A1 | 7/2010 | Jeha et al. |
| 2010/0229867 | A1 | 9/2010 | Bertinetti et al. |
| 2011/0017212 | A1 | 1/2011 | Kenyon et al. |
| 2011/0023877 | A1 | 2/2011 | Kenyon et al. |
| 2011/0180068 | A1 | 7/2011 | Kenyon et al. |
| 2015/0020805 | A1 | 1/2015 | Lithgow et al. |
| 2016/0175554 | A1 | 6/2016 | Lithgow et al. |

FOREIGN PATENT DOCUMENTS

| | | |
|---|---|---|
| CN | 2086150 | 10/1991 |
| CN | 2239819 | 11/1996 |
| CN | 1210020 | 3/1999 |
| CN | 1314192 | 9/2001 |
| DE | 275612 | 1/1913 |
| DE | 30 05 094 | 8/1981 |

(56) References Cited

FOREIGN PATENT DOCUMENTS

| | | | |
|---|---|---|---|
| DE | 3623162 | A1 | 7/1986 |
| DE | 3642637 | | 6/1988 |
| DE | 3823242 | A1 | 2/1990 |
| DE | 9014848.7 | | 3/1991 |
| DE | 4138098 | C2 | 11/1991 |
| DE | 4244493 | A1 | 7/1993 |
| DE | 93 17 450 | | 6/1994 |
| DE | 3789221 | | 8/1994 |
| DE | 9409231.1 | | 12/1994 |
| DE | 19515739 | C2 | 5/1995 |
| DE | 19630466 | | 2/1998 |
| DE | 29817685 | | 10/1998 |
| DE | 69409024 | T2 | 11/1998 |
| DE | 19752672 | | 3/1999 |
| DE | 29817685 | U1 | 6/1999 |
| DE | 29909611 | | 10/1999 |
| DE | 29909611 | U1 | 10/1999 |
| DE | 200 13 392 | U1 | 10/2000 |
| DE | 10021782 | | 11/2000 |
| DE | 1999 36 499 | | 2/2001 |
| DE | 10016005 | | 12/2001 |
| DE | 10016005 | A1 | 12/2001 |
| DE | 20213232 | | 4/2003 |
| DE | 102005007773 | A1 | 9/2005 |
| EP | 0201985 | | 11/1986 |
| EP | 0274996 | A2 | 7/1988 |
| EP | 0274996 | B1 | 7/1988 |
| EP | 0 376 584 | | 7/1990 |
| EP | 0298367 | B1 | 10/1993 |
| EP | 0589 429 | | 3/1994 |
| EP | 0 760 247 | | 3/1997 |
| EP | 0845277 | A2 | 6/1998 |
| EP | 0 893 750 | | 1/1999 |
| EP | 0 903 160 | | 3/1999 |
| EP | 0903160 | A1 | 3/1999 |
| EP | 1 002 552 | A2 | 5/2000 |
| EP | 1023912 | A2 | 8/2000 |
| EP | 1 055 431 | | 11/2000 |
| EP | 1 087 322 | | 3/2001 |
| EP | 1318307 | | 6/2003 |
| EP | 1 374 938 | | 1/2004 |
| FR | 2 323 436 | | 4/1977 |
| FR | 2 714 985 | | 7/1995 |
| GB | 1556492 | | 11/1979 |
| GB | 2069607 | A | 8/1981 |
| GB | 2177006 | A | 1/1987 |
| GB | 2192136 | A | 1/1988 |
| GB | 2293325 | | 3/1996 |
| GB | 2353904 | A | 3/2001 |
| JP | 55-104925 | | 8/1980 |
| JP | 58-036560 | | 3/1983 |
| JP | 61-179161 | | 8/1986 |
| JP | 64-500088 | | 1/1989 |
| JP | 2-19168 | | 1/1990 |
| JP | 4-69434 | | 3/1992 |
| JP | 05-104681 | | 4/1993 |
| JP | 5-285220 | | 11/1993 |
| JP | H06-502921 | | 3/1994 |
| JP | 6-26894 | | 4/1994 |
| JP | 06-190928 | | 7/1994 |
| JP | 7-145795 | A | 6/1995 |
| JP | 07-037195 | | 7/1995 |
| JP | 7-275362 | | 10/1995 |
| JP | 08-178781 | | 7/1996 |
| JP | 9-103490 | | 4/1997 |
| JP | 11-398 | A | 1/1999 |
| JP | 2000-237316 | | 9/2000 |
| JP | 2000-337670 | | 12/2000 |
| JP | 2001-61814 | | 3/2001 |
| JP | 2001-160102 | | 6/2001 |
| JP | 2001-251802 | | 9/2001 |
| JP | 2001-516277 | | 9/2001 |
| JP | 2002-206498 | A | 7/2002 |
| JP | 2002-248167 | | 9/2002 |
| JP | 2002-253672 | | 9/2002 |
| JP | 2002-306601 | | 10/2002 |
| JP | 2003-506161 | | 2/2003 |
| JP | 2003-527160 | | 9/2003 |
| JP | 2004-532666 | | 10/2004 |
| WO | 88/00068 | | 1/1988 |
| WO | WO 93/05451 | | 3/1993 |
| WO | WO 95/15778 | | 6/1995 |
| WO | WO 97/32619 | | 9/1997 |
| WO | 98/04311 | | 2/1998 |
| WO | WO 98/31937 | | 7/1998 |
| WO | WO 98/33433 | | 8/1998 |
| WO | 98/41306 | | 9/1998 |
| WO | WO 98/57691 | | 12/1998 |
| WO | WO 99/13932 | | 3/1999 |
| WO | WO 99/22794 | | 5/1999 |
| WO | WO 99/64747 | | 12/1999 |
| WO | WO 0021602 | | 4/2000 |
| WO | WO 00/27457 | | 5/2000 |
| WO | WO 00/32261 | | 6/2000 |
| WO | 0038771 | | 7/2000 |
| WO | WO 00/42324 | | 7/2000 |
| WO | WO 01/10489 | A2 | 2/2001 |
| WO | WO 01/32069 | | 5/2001 |
| WO | WO 01/73653 | A1 | 10/2001 |
| WO | WO 02/02169 | A1 | 1/2002 |
| WO | 02/20075 | | 3/2002 |
| WO | 02/053217 | | 7/2002 |
| WO | 02/066105 | | 8/2002 |
| WO | 02/066106 | | 8/2002 |
| WO | 02/066107 | | 8/2002 |
| WO | WO 02/066107 | A1 | 8/2002 |
| WO | 03/090827 | | 11/2003 |
| WO | 2004/069318 | A1 | 8/2004 |
| WO | 2004/112873 | | 12/2004 |
| WO | 2005/011556 | | 2/2005 |
| WO | WO 2007/019628 | | 2/2007 |
| WO | WO 2009/059359 | | 5/2009 |
| WO | WO 2009/156921 | A1 | 12/2009 |
| WO | WO 2010/092496 | | 8/2010 |

OTHER PUBLICATIONS

Notification of the Second Office Action dated Mar. 17, 2016 issued in Chinese Application No. 201410017494.4 with English translation (12 pages).

Office Action for U.S. Appl. No. 10/533,940, filed Dec. 29, 2006, mailed Oct. 12, 2010, 10 pages.

Kenyon et al., U.S. Appl. No. 12/900,008, filed Oct. 7, 2010.

Kenyon et al., U.S. Appl. No. 12/900,781, filed Oct. 8, 2010.

Office Action and English Translation issued in Japanese Application No. 2006-515549, mailed Nov. 2, 2010, 7 pages.

Further Examination Report dated Dec. 16, 2015 issued in New Zealand Application No. 710686 (4 pages).

Patent Examination Report No. 2 dated Feb. 12, 2016 issued in Australian Application No. 2014246587 (3 pages).

Office Action dated Nov. 9, 2015 issued in Japanese Application No. 2014-253908 with English language translation (9 pages).

Office Action dated Nov. 30, 2015 issued in U.S. Appl. No. 12/659,963 (54 pages).

Fisher & Paykel Healthcare, "HC200 Series Nasal CPAP Blower & Heated Humidifier User's Manual", 1998, 17 pages.

Notice of Reasons for Rejection dated Sep. 7, 2015 issued in Japanese Application No. 2014-006622 with English language translation (7 pages).

First Examination Report dated Aug. 28, 2015 issued in corresponding New Zealand Application No. 710686 (2 pages).

Notification of First Office Action dated Jul. 28, 2015 issued in Chinese Application No. 2014100174944 with English translation (11 pages).

Patent Examination Report No. 1 dated Jul. 27, 2015 issued in Australian Application No. 2014246587 (4 pages).

Patent Examination Report No. 1 dated Jul. 27, 2015 issued in Australian Application No. 2014246586 (4 pages).

Proceedings Correspondence issued Mar. 1, 2012 in corresponding New Zealand Application No. 567371.

(56) References Cited

OTHER PUBLICATIONS

Office Action issued on Aug. 24, 2012 in corresponding Australian Application No. 2010257238.
Office Action issued on Aug. 7, 2012 in corresponding Japanese Application No. 2010-153008 (with translation).
Office Action issued on Jan. 22, 2013 in corresponding Japanese Application No. 2011-201622.
Office Action issued on Mar. 7, 2013 in corresponding New Zealand Application No. 607671.
Office Action issued on Mar. 7, 2013 in corresponding New Zealand Application No. 596207.
Search Report issued on Jun. 6, 2013 in corresponding European Application No. 11175449.5.
Japanese Office Action (Decision of Rejection) for Application No. 2011-201622 dated Aug. 13, 2013 w/ English Translation (7 pages).
Office Action issued on Sep. 17, 2013 in corresponding Japanese Application No. 2010-153008 (with Translation).
Office Action issued on Oct. 4, 2013 in corresponding Australian Application No. 2013201490.
Office Action issued on Oct. 4, 2013 in corresponding Canadian Application No. 2,753,378.
Notice of Reasons for Rejection issued Aug. 11, 2014 in corresponding Japanese Application No. 2011-201622 with English translation (2 pages).
Office Action dated Sep. 8, 2014 issued in corresponding Canadian Application No. 2,753,378 (2 pages).
Statement of Case dated Dec. 1, 2014 in New Zealand Application No. 607671 (6 pages).
Amended Notice of Opposition to Grant Patent (Section 21) in New Zealand Application No. 607671 (2 pages).
Notice of Reasons for Rejection dated Dec. 22, 2014 issued in Japanese Application No. 2014-0006622 with English translation (6 pages).
Notice of Allowance dated Jan. 7, 2015 issued in U.S. Appl. No. 14/445,143 (32 pages).
Notice of Allowance dated Jan. 13, 2015 issued in U.S. Appl. No. 14/445,152 (35 pages).
Notification of Second Office Action dated Dec. 24, 2014 issued in Chinese Application No. 201210297972.2 with English-language translation (14 pages).
Office Action dated Feb. 5, 2015 issued in related U.S. Appl. No. 14/445,190.
REMStar® Heated Humidifier Manual, Mar. 15, 2001 (8 pages).
Australian Application No. PR 7288, filed Aug. 27, 2001 (23 pages).
Australian Application No. PR 3117, filed Feb. 16, 2001 (17 pages).
De Vilbiss® Healthcare, "De Vilbiss IntelliPAP® Standard CPAP System", Nov. 2007, 2 pages.
Photos of tray system available before the critical date, with sample flow generator and humidifier (5 pages).
New Zealand Patent Application No. 503495, filed Jan. 22, 2004 (29 pages).
Office Action dated Feb. 25, 2015 issued in U.S. Appl. No. 12/659,963 (99 pages).
Extended Search Report dated Jun. 9, 2015 issued in European Application No. 14200112.2 (8 pages).
Office Action dated Mar. 11, 2016 issued in U.S. Appl. No. 14/965,976 (25 pages).
Notice of Allowance dated Oct. 28, 2015 issued in U.S. Appl. No. 14/790,693 (36 pages).
Office Action dated Sep. 25, 2015 issued in U.S. Appl. No. 14/791,744 (30 pages).
U.S. Appl. No. 14/445,190, filed Jul. 29, 2014.
U.S. Appl. No. 14/965,976, filed Dec. 11, 2015.
U.S. Appl. No. 13/916,930, filed Jun. 13, 2013.
U.S. Appl. No. 14/791,744, filed Jul. 6, 2015.
U.S. Appl. No. 14/791,775, filed Jul. 6, 2015.
U.S. Appl. No. 15/042,474, filed Feb. 12, 2016.
U.S. Appl. No. 14/790,693, filed Jul. 2, 2015.
U.S. Appl. No. 12/659,963, filed Mar. 26, 2010.
U.S. Appl. No. 14/445,143, filed Jul. 29, 2014.
U.S. Appl. No. 14/445,152, filed Jul. 29, 2014.
Petition for Inter Partes Review of U.S. Pat. No. 7,614,398, mailed Aug. 16, 2013.
Declaration of Joseph Dyro, Petition Exhibit 1007.
Notification of Acceptance of Request for Invalidation, Issued: Dec. 24, 2014, in Chinese Patent No. 02804936.5, with English translation, 62 pages.
U.S. International Trade Commission, Inv. No. 337-TA-890, "Office of Unfair Import Investigations' Petition for Review of the Initial Determination," dated Sep. 3, 2014 (Public Version Filed: Oct. 8, 2014), 34 pages.
U.S. International Trade Commission, Inv. No. 337-TA-890, "Office of Unfair Import Investigations' Response to the Petitions for Review of the Initial Determination," dated Sep. 11, 2014 (Public Version Filed: Oct. 8, 2014), 37 pages.
Fisher & Paykel Limited, New Zealand Application No. 503495, filed Mar. 21, 2000, 29 pages.
U.S. International Trade Commission, Inv. No. 337-TA-890, "Office of Unfair Import Investigations' Response to ResMed's Motion to Withdraw the '487 Patent or Alternatively Find No Violation Based on Technical Prong," dated Nov. 19, 2014 (Public Version Filed: Dec. 3, 2014), 5 pages.
U.S. International Trade Commission, Inv. No. 337-TA-890, "Notice of the Commission's Final Determination; Issuance of a Limited Exclusion Order and Cease and Desist Orders; Termination of the Investigation," Issued: Dec. 23, 2014, 25 pages.
U.S. Patent and Trademark Office, Case IPR2014-01196, U.S. Pat. No. Re. 44,453 E, "Decision Institution of Inter Partes Review 37 C.F.R. §42.108," Paper No. 7, Entered: Dec. 21, 2014, 11 pages.
U.S. Patent and Trademark Office, Case IPR2014-01196 and IPR2014-01363, U.S. Pat. No. Re. 44,453 E, "Scheduling Order," Entered: Jan. 21, 2015, 9 pages.
US. Patent and Trademark Office, Case IPR2014-01363, U.S. Pat. No. Re. 44,453 E, Decision Institution of Inter Partes Review 37 C.F.R. §42.108, Paper No. 7, Entered: Jan. 21, 2015, 21 pages.
Communication Pursuant to Article 94(3) EPC mailed Feb. 4, 2015 in European Application No. 12 159 042.6 (4 pages).
Notification of Acceptance of Request for Invalidation and English Translation for corresponding Chinese Patent No. 02804936.5, issued Mar. 20, 2014, 188 pages.
Map Medizintechnik, "Moritz II biLevel® —The gentle therapy for sleep-related breathing disorders" brochure, 6 pages, Jan. 2001.
Notification of Second Office Action mailed Jan. 27, 2006 in Chinese Appln. No. 02804936.5, with English translation (6 pages).
Notification of Reasons for Rejection mailed Feb. 19, 2008 in Japanese Appln. No. 2002-565664, with English translation (5 pages).
Final Notice of Reasons for Rejection delivered Sep. 24, 2008 in Japanese Appln. No. 2002-565664, with English translation (6 pages).
Notification of the First Office Action mailed Jul. 22, 2005 in Chinese Appln. No. 02804936.5, with English translation (8 pages).
Extended European Search Report mailed Apr. 28, 2011 in European Appln. No. 10189422.8 (5 pages).
International Search Report mailed Mar. 21, 2002 in International Appln. No. PCT/AU02/00155 (2 pages).
International Preliminary Examination Report completed Oct. 4, 2002 in International Appln. No. PCT/AU02/00155 (3 pages).
Office Action dated Jan. 22, 2008 in Japanese Patent Appln. No. 2002-565665 (w/ English translation) (12 pages).
Examination Report mailed Oct. 10, 2003 in New Zealand Appln. No. 527088 (2 pages).
Supplementary European Search Report mailed Sep. 15, 2009 in European Appln. No. 02700014.0 (3 pages).
ITC Action related to Certain Sleep-Disordered Breathing Treatment Systems And Components Thereof, Inv. No. 337-TA-__, CBI 13-185, filed on Mar. 28, 2013, 57 pages.
ResMed's First Amended Complaint for Patent Infringement, filed in the United States District Court Central District of California Southern Division, filed on Apr. 8, 2013, 342 pages.
"Complaint for Patent Infringement—Jury Trial Demanded" as filed in the United States District Court, Southern District of California, Case No. '13CV1246 MMAWMC, dated May 29, 2013, 25 pages.

(56) References Cited

OTHER PUBLICATIONS

"Motion to Amend the Complaint and Notice of Investigation" as filed in the United States International Trade Commission, Investigation No. 337-TA-879, dated May 31, 2013, 18 pages.
Petition for Inter Partes Review of U.S. Pat. No. Re. 44,453, *BMC Medical Co., Ltd.*, Petitioner v. *ResMed Limited*, Patent Owner, Case No. IPR2014-01363, Aug. 22, 2014, 66 pages.
Petition Exhibit 1004 in IPR2014-01363, Declaration of Steve Bordewick, Aug. 22, 2014, 90 pages.
Petition for Inter Parties Review of U.S. Pat. No. Re. 44,453 Under To 35 U.S.C. §§ 311 ET SEQ. And 37 C.F.R. §42.100 ET SEQ., *Apex Medical Corp.*, Petitioner v. *ResMed Limited*, Patent Owner, Case No. IPR2014-00551, Mar. 27, 2014, 38 pages.
Apex Medical Corporation, Petition Exhibit 1002 in IPR2014-00551, "ResMed's First Amended Complaint for Patent Infringement—Jury Trial Demanded", Case No. SACV-13-00498 CJC (RNBx), USDC, Central District of California, Southern Division, 18 pages.
Petition Exhibit 1006 in IPR2014-00551, Patent Owner Amendment mailed Mar. 27, 2009, in U.S. Appl. No. 11/181,807, 10 pages.
Petition Exhibit 1007 in IPR2014-00551, Declaration of Joseph Dyro in Support of Inter Panes Review of U.S. Pat. No. Re. 44,453, executed Mar. 26, 2014, 15 pages.
Communication mailed Jul. 1, 2010 in European Appln. No. 02 700 014.0 (5 pages).
Extended European Search Report mailed May 4, 2012 in European Appln. No. 12159042.6 (5 pages).
Petition Exhibit 1006 in IPR2014-01196, Patent Owner ResMed Limited's Preliminary Response filed Jul. 10, 2014, in IPR2014-00551, 41 pages.
Petition Exhibit 1007 in IPR2014-01196, ITC Investigation No. 337-TA-890,: Order No. 7: Initial Determination Granting Complainants' Motion to Amend Complaint and Notice of Investigation and Granting Respondents' Motion to Terminate the Investigation with Respect to U.S. Pat. No. 7,614,398, served Feb. 4, 2014, 8 pages.
Petition Exhibit 1008 in IPR2014-01196, Case No. 13-cv-1246-CAB (WMc), Order on Motion to Stay, Motion to Dismiss, and Related Discovery Request, Oct. 15, 2013, 3 pages.
Petition Exhibit 1009 in IPR2014-01196, Case No. SACV 13-00498: Order Granting Defendants' Motion to Stay Litigation Pending Inter Partes Review, Oct. 4, 2013, 3 pages.
Petition Exhibit 1010 in IPR2014-01196: Patent Prosecution History of Reissue U.S. Appl. No. 13/944,960, filed Jul. 18, 2013, 228 pages.
Petition Exhibit 1011 in IPR2014-01196: Patent Prosecution History of U.S. Pat. No. 7,614,398, 174 pages.
Petition Exhibit No. 1012 in IPR2014-01196: Patent Prosecution History of U.S. Pat. No. Re. 44,453, 2157 pages.
Petition Exhibit No. 1013 in IPR2014-01196: Proof of Service of 3B Medical, Inc. In Civil Action No. 13-cv-1246-MMA-WMC, 5 pages.
Petition Exhibit No. 1014 in IPR2014-01196: Australian Application No. PR 3117, filed Feb. 16, 2001, 17 pages.
Petition Exhibit No. 1016 in IPR2014-01196: ITC Investigation No. 337-TA-890: Order No. 14: Denying Respondents' Motion for Summary Determination of Invalidity of U.S. Pat. No. Re. 44,453, served Mar. 26, 2014, 19 pages.
Petition Exhibit No. 1020 in IPR2014-01196: Australian Application No. PR 7288, filed Aug. 27, 2001, 23 pages.
Petition Exhibit No. 1022 in IPR2014-01196: ITC Investigation No. 337-TA-890: Notice of Commission Determination Not to Review an Initial Determination Granting the Complainants' Motion to Amend the Complaint and Notice of Investigation to Substitute U.S. Pat. No. Re. 44,453 for U.S. Pat. No. 7,614,398 and Granting Respondents' Motion to Terminate the Investigation with Respect to U.S. Pat. No. 7,614,398, Issued: Feb. 10, 2014, 3 pages.
Petition for Inter Parties Review of U.S. Pat. No. Re. 44,453 Under to 35 U.S.C. §§311-319 and 37 C.F.R. §42.100 et seq., *BMC Medical Co. Ltd.*, Petitioner v, *ResMed Limited*, Patent Owner, Case No. IPR2014-01196, Jul. 23, 2014, 62 pages.
Petition Exhibit 1003 in IPR2014-01196, REMStar® Heated Humidifier Manual, Mar. 15, 2001, 8 pages.
Petition Exhibit 1004 in IPR2014-01196, Declaration of Steve Bordewick, Jul. 22, 2014, 59 pages.
Patent Owner Exhibit No. 2010 in IPR2014-00551, Deposition Transcript of Dr. Joseph F. Dyro in Connection with Inter Partes Review Proceedings IPR2013-00511, IPR2013-00512, IPR2013-00514, IPR2013-00515, and IPR2013-00516, Apr. 21, 2014, 46 pages.
Patent Owner Exhibit No. 2011 in IPR2014-00551, Patent Owner ResMed Limited's Preliminary Response to Apex Medical Corp.'s Petition for Inter Partes Review of U.S. Pat. No. 7,614,398, Case No. IPR2013-00513, Nov. 22, 2013, 15 pages.
Petition Exhibit No. 1015 in IPR2014-01196: ITC Investigation No. 337-TA-890: Order No. 8: Construing Terms of the Asserted Patents, served Jan. 17, 2014, 51 pages.
Australian Office Action for corresponding AU Appln. No. 2004248855, Mailed Nov. 6, 2009, 5 pages.
Australian Office Action for corresponding AU Appln. No. 2010201899, Mailed Jun. 10, 2010, 5 pages.
Examiner Summary from Meeting corresponding AU Appln. No. 2010201899, Aug. 12, 2010, 3 pages.
Chinese Office Action for co-pending Chinese Application No. 200480017315.1 and English translation, issued Oct. 9, 2009, 14 pages.
Supplementary European Search Report for Co-pending European Application No. 04737434.3, mailed Oct. 15, 2009, 4 pages.
International Search Report for PCT/AU2004/000810 mailed Oct. 1, 2004.
Office Action dated May 19, 2015 issued in related U.S. Appl. No. 14/445,190 (14 pages).
Hoffrichter/Sandmann CPAP Respirator—Perfect CPAP Therapy, 30 pages plus Translation Verification Certificate, Mar. 1998.
Patent Owner Exhibit No. 2001 in IPR2014-00551, Applicant Transmittal to USPTO re Completion of National Phase Filing of the PCT Application for the Mayer Reference, Aug. 6, 2002, 4 pages.
Patent Owner Exhibit No. 2002 in IPR2014-00551, Re. 44,453 Patent Application Data Sheet, Initial May 4, 2011, 5 pages.
Patent Owner Exhibit No. 2003 in IPR2014-00551, Decision of the Patent Trial and Appeal Board Denying Institution of Inter Partes Review of U.S. Pat. No. 7,614,398, entered Feb. 20, 2014, 5 pages.
Patent Owner Exhibit No. 2005 in IPR2014-00551, U.S. National Stage Worksheet of USPTO re National Phase Requirements Completion for the Mayer Reference, 1 page.
U.S. International Trade Commission, Inv. No. 337-TA-890, "Office of Unfair Import Investigations' Reply to the Private Parties' Responses to the Commission Question," dated Nov. 7, 2014 (Public Version Filed: Dec. 3, 2014), 19 pages.
Final Rejection dated Aug. 1, 2016 issued in Japanese Application No. 2014-253908 with English Translation (10 pages).
Breas Medical AB "iSleep® 20" Brochure, Dec. 2007, 2 pages.
Fisher & Paykel Healthcare "SleepStyle™ 200 CPAP Series" Specification Sheet, 2005, 4 pages.
J. H. Emerson Co., Cough Assist, "Non-Invasive Removal of Bronchial Secretions," 2 pages.
Supplementary European Search Report for copending EP Appln. No. 04737434.3, mailed Oct. 15, 2009, 4 pages.
MAP Medizintechnik, "Moritz II biLEVEL®—The gentle therapy for sleep-related breathing disorders" brochure, 6 pages, Jan. 2001.
Madaus Schwarzer Medizintechnik, "New Approaches in Diagnosis and Therapy—Max nCPAP User Manual", Mar. 1994, 38 pages.
MAP Medizin-Technologie GmbH, Moritz®S/Moritz®ST— Sailing toward therapeutic success . . . , 4 pages, undated.
Australian Office Action for AU Appln. No. 2004248855, Mailed Nov. 6, 2009, 5 pages.
Australian Office Action for AU Appln. No. 2010201899, Mailed Jun. 10, 2010, 5 pages.
Examiner summary from Meeting AU Appln. No. 2010201899, Aug. 12, 2010, 3 pages.

(56) References Cited

OTHER PUBLICATIONS

German Patient Manual for Hoffrichter/Sandmann CPAP Respirator—Perfect CPAP Therapy, 30 pages plus Translation Verification Certificate, no date.
Notice of Reasons for Rejection mailed May 15, 2011 in corresponding Japanese Application No. 1117544, with English translation (4 pages).
Office Action issued in related Chinese Application No. 201010154162.2 (May 31, 2011) w/English translation.
Chinese Office Action and English Translation for copending CN Appln. No. 200480017315.1,issued Oct. 9, 2009,14 pgs.
International Search Report of PCT/AU2004/000810, mailed Oct. 1, 2004.
Decision of Rejection dated Apr. 25, 2016 issued in Japanese Application No. 2014-006622 with English translation (5 pages).
Office Action dated May 26, 2016 issued in U.S. Appl. No. 15/054,820 (37 pages), which cited U.S. Pat. No. 5,928,177.
Office Action dated Jun. 2, 2016 issued in U.S. Appl. No. 13/916,930 (28 pages).
Office Action dated Jun. 7, 2016 issued in U.S. Appl. No. 15/042,474 (32 pages).
Notice of Reasons for Rejection dated Apr. 4, 2016 issued in Japanese Application No. 2015-059122 with English translation (6 pages).
Office Action dated Jun. 8, 2016 issued in European Application No. 14200112.2 (7 pages).
Notification of the First Office Action dated Mar. 25, 2016 issued in Chinese Application No. 201410559916.0 with English translation (17 pages).
Notification of the Second Office Action dated Dec. 12, 2016 issued in Chinese Application No. 201410559916.0 with English translation (10 pages).
Office Action dated Jan. 19, 2017 issued in Canadian Application No. 2,912,125 (5 pages).
First Examination Report dated Feb. 17, 2017 issued in New Zealand Application No. 728764 (2 pages).
Office Action dated Feb. 22, 2017 issued in Chinese Application No. 2015105124185 with English translation (10 pages).
Notice of Opposition dated Oct. 12, 2016 issued in European Application No. 11175449.5 with English translation (24 pages).
Office Action dated Dec. 26, 2016 issued in Japanese Application No. 2015-59122 with English translation (10 pages).
Fisher & Paykel Healthcare "SleepStyle™ 200 CPAP Series" Specification Sheet, 1998, 4 pages.
Fisher & Paykel Healthcare "SleepStyle™ 600 CPAP Series" Specification Sheet, 2005, 4 pages.
Fisher & Paykel Healthcare Two Easy Steps to Comfort, Humidification and Nasal CPAP Therapy, Aug. 1995, 4 pages.
Hoffrichter GmbH "Vector therapy in perfection" Brochure, 2002, 2 pages.
MAP Medizin-Technologie GmbH "minni Max nCPAP®, The respiratory therapy device with•out an integrated humidifier", Dec. 2003, 17 pages.
MAP Medizintechnik fuer Arzt und Patient "max II nCPAP moritz II biLevel—The gentle therapy for sleep-related breathing disorders" Brochure, 2000, 4 pages.
Respironics "System One Heated Humidifier User Manual", May 2009, 20 pages.
ResMed, "The Sullivan® HumidAire™", 1997, 1 page.
Office Action and English Translation from corresponding JP Appln. No. 2010-224861, mailed Jan. 18, 2011, 7 pages.
Office Action and English Translation from copending JP Appln. No. 2006-515549, mailed Jan. 5, 2010, 11 pages.
Office Action from corresponding European Appln. No. 04737434.3, mailed Apr. 14, 2010, 8 pages.
Office Action from corresponding European Appln. No. 04737434.3, mailed Apr. 26, 2010, 8 pages.
Australian Office Action for corresponding AU Appln. No. 2010257238, Mailed Mar. 10, 2011, 2 pages.
Hoffrichter Medizintechnik GmbH, "Sandmann CPAP—Therapie in Perfektion" brochure, 32 pages, Mar. 1998.
Madaus Schwarzer Medizintechnik, "New Approaches in Diagnosis and Therapy—Moritz biLevel User Manual", May 1994, 38 pages.
MAP Medizintechnik, "minni Max nCPAP®" brochure, 12 pages, Mar. 2005.
Hoffrichter "Vector CPAP—Therapy With Technical Mastery", 4 pages, Oct. 1998.
Fischer & Paykel, "Two Easy Steps to Comfort", 4 pages, Aug. 1995.
Office Action and English Translation from corresponding JP Appln. No. 2010-224862, mailed Jan. 4, 2011, 9 pages.
Office Action and English Translation from corresponding JP Appln. No. 2011-007671, mailed Mar. 1, 2011, 6 pages.
Australian Office Action for corresponding AU Appln. No. 2010241520, Mailed Nov. 29, 2010, 2 pages.
Notice of Reasons for Rejection mailed May 15, 2011 in corresponding Japanese Application No. 2006-515549, with English translation (4 pages).

* cited by examiner

BREATHABLE GAS APPARATUS WITH HUMIDIFIER

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

This is a continuation of U.S. application Ser. No. 10/533,940, filed Dec. 29, 2006, pending, which is a national phase application of PCT/AU2004/000810, filed Jun. 21, 2004 in English, which claims the benefit of Australian Application No. 2003903139, filed Jun. 20, 2003, Australian Application No. 2003905136, filed Sep. 22, 2003, and Australian Application No. 2004901008, filed Feb. 24, 2004, each incorporated herein by reference in its entirety.

BACKGROUND OF THE INVENTION

1. Field of the Invention

This invention relates to breathable gas supply apparatus, and particularly but not exclusively to such apparatus for use in Continuous Positive Airway Pressure (CPAP) treatment of conditions such as Obstructive Sleep Apnea (OSA) and other respiratory disorders and diseases such as emphysema. It will be described herein in its application to CPAP treatment apparatus, but it is to be understood that the features of the invention will have application to other fields of application, such as mechanical ventilation and assisted respiration.

2. Description of Related Art

CPAP treatment of OSA, a form of Noninvasive Positive Pressure Ventilation (NIPPY), involves the delivery of a pressurised breathable gas, usually air, to a patient's airways using a conduit and mask. Gas pressures employed for CPAP typically range from 4 cm $H_2O$ to 28 cm $H_2O$, at flow rates of up to 180 L/min (measured at the mask), depending on patient requirements. The pressurised gas acts as a pneumatic splint for the patient's airway, preventing airway collapse, especially during the inspiratory phase of respiration.

CPAP machines comprising an air flow generator for supplying pressurised air to the patient are known, and over recent years there has been commercial imperative for more compact CPAP machines. However, in seeking to reduce the size of the CPAP machines there has been a trade-off between reduced size on the one hand and reduced performance and/or increased noise on the other, for example Malinckrodt/Tyco/Puritan Bennett 'Goodnight' Series.

The advantages of incorporating humidification of the air supply to a patient are known, and CPAP machines are known which incorporate humidifying devices, either separately from the flow generator or integrated therewith. An example of an integrated flow generator/humidifier unit is the ResMed® S7 sold by the present Applicant.

Another problem with some flow generators is extensive use of foam in the air path for sound absorption. The foam can degrade with time.

SUMMARY OF THE INVENTION

One of the objects of the invention is to provide a simple and compact breathable gas supply apparatus incorporating a humidifier which is simple and economic in its construction, compact, and easy to use. Other objects and advantages of the invention will be described throughout the specification.

It is to be understood that apparatus described herein contains a number of advances on the prior art, many of which are independent inventions, although they contribute together to the realisation of the general object expressed above.

The apparatus described herein incorporates novel aspects of architecture of both the flow generator and the humidifier, and of their integration, which contribute to a reduction in size compared with known units having similar performance. Techniques for noise reduction and damping are described which enable such a smaller machine to have noise performance which is at least as good as known larger machines.

The apparatus described herein achieves full integration of the humidifier with the flow generator, in the sense that air flow, electrical and, if required, data connection between the flow generator and the humidifier are provided automatically upon the physical engagement of the two devices, without the need for any other process of interconnection.

In such an integrated device, provisions to guard against flowback of water from the humidifier tank to the flow generator are important, and novel sealing arrangements, and novel arrangements for minimising the occurrence of flowback while at the same time improving the uptake of water vapour in the humidifier are also described. The humidifier is readily detached and replaced on the machine, and has very few parts to be disassembled during cleaning.

Also described herein are improved, modular, devices for enabling data connection with the apparatus, including the connection of data storage devices such as memory cards, smart cards, communication ports and the like to be selectively attached by the user or by medical personnel.

Another aspect of the invention is to reduce or eliminate the use of foam in the air path.

In one form, the invention provides a flow generator unit for delivering breathable gas to a patient, including:

- a flow generator case;
- a powered gas flow generator within the case;
- a power supply unit adapted for drop-in assembly in said case, said power supply unit including a printed circuit board, a power input connector rigidly attached to said printed circuit board and a power output connector, and
- a power supply unit mounting for mounting said power supply unit in said case such that said power input connector aligns with a power input port of said case.

A further form of the invention provides a blower enclosure for a flow generator used in delivery of breathable gas to a patient, said blower enclosure including a metal container overmoulded with an acoustically damping polymer lining.

A further form of the invention provides a blower enclosure for a flow generator used in delivery of breathable gas to a patient, said blower being adapted to reduce noise from the enclosed blower, said enclosure comprising:

- a cavity within a chassis of the flow generator, the cavity defined by side walls and base, the enclosure being adapted to receive and mount a blower in said cavity and
- a lid adapted to be mounted on said chassis so as to form a top surface of the cavity, wherein at least one of the chassis and lid is moulded from a composite comprising a metal and a plastic.

A further form of the invention provides a blower for a flow generator used in delivery of breathable gas to a patient, said blower comprising an electric motor with a shaft, an impeller adapted to be mounted on the shaft, and a volute having an air-inlet and an air-outlet, the volute defining a chamber in which a flow of air at pressure is developed, the volute being moulded from a composite comprising a first plastic material and a second plastic material, the first plastic material being generally rigid and the second material being generally elastomeric.

Preferably, wherein the first plastic material is overmoulded with the second plastic material.

Preferably, the volute comprises an upper volute and a lower volute, the lower volute incorporating the air-inlet. Preferably also, the lower volute includes feet moulded from the second plastics material.

Preferably, the upper volute incorporates the air-outlet. Preferably also, the upper volute includes a seal constructed from the second plastic material and which in use is adapted to provide a seal between the upper and lower volutes.

In one embodiment the upper and lower volutes are adapted to be snap-fitted together.

A further form of the invention provides a flow generator case for a flow generator used in delivery of breathable gas to a patient, said flow generator case comprising a shell of rigid plastics overmoulded with an elastomeric lining.

Preferably, said elastomeric lining forms external feet of said flow generator case.

A further form of the invention provides a fan support arrangement for a flow generator used in delivery of breathable gas to a patient, including a fan housing containing a motor and fan, said support arrangement including a plurality of mounting springs, wherein said springs, fan housing, motor and fan form a spring system having a natural resonant frequency less than one tenth of the frequency of a lowest operating speed of said fan.

A further form of the invention provides a flow generator unit for delivering breathable gas to a patient, including a flow generator ease having an air outlet, a fan volute contained within said case, further including a flexible tube connecting an outlet of said fan volute to said air outlet, said flexible tube having two or more corrugations therein.

A further form of the invention provides a flow generator and humidifier combination for continuous positive airway pressure treatment of a patient, including a flow generator and a humidifier removably attached to the flow generator, wherein said flow generator includes a humidifier attachment detector including an optical transmitter and an optical sensor and wherein said humidifier includes an optical path connector which, when said flow generator and humidifier are attached, completes an optical path between said optical transmitter and said optical sensor.

A further form of the invention provides a muffler arrangement in an air flow path of a flow generator used in delivery of breathable gas to a patient, including a first muffler volume, a second muffler volume and a connecting portion linking said first and second muffler portions, wherein said connecting portion is narrow relative to said muffler portions and includes a lead-in portion which narrows in a direction away from said first muffler portion.

Preferably said connecting portion includes a venturi.

A further form of the invention provides a handle assembly for a flow generator used in delivery of breathable gas to a patient, including a flow generator case, a handle including a pair of attachment arms, each attachment arm having a projection received in a respective track of said case, and a handle retention member which attaches to said case to retain said handle projections against travel along said track.

A further form of the invention provides a method of attachment of a handle to a flow generator case, said handle including a pair of attachment arms, each attachment arm having a projection received in a respective track of said case, including the steps of sliding said handle projections along respective of said tracks and attaching a handle retention member to said case to retain said projections against travel along said respective tracks.

Preferably, said sliding of said handle projections along said track occurs without substantial distortion of said attachment arms.

A further form of the invention provides a humidifier for delivering humidified breathable gas to a patient, including a humidifier case, a water container, a heater located in heat transfer communication with said water container, a gas flow path including a gas inlet, a humidified gas outlet and an intermediate gas flow path which contacts the gas with water vapour from said container, further including a drainage opening adjacent said heater allowing drainage of water past the heater to exit said humidifier case.

A further form of the invention provides a humidifier for delivering humidified breathable gas to a patient, including a humidifier case, a water container, a heater pad located in heat transfer communication with said water container, a gas flow path including a gas inlet, a humidified gas outlet and an intermediate gas flow path which contacts the gas with water vapour from said container, wherein said heater pad has an upper heating surface and a peripheral heating surface which includes a side wall of said heater pad, and wherein a heat transfer surface of said water container is shaped to correspond to said heater pad so as maintain close heat transfer communication with said upper heating surface and peripheral heating surface of said heater pad.

Preferably, said water container defines a water volume which extends both above and below a level of said heating pad upper heating surface, A further form of the invention provides a humidifier for delivering humidified breathable gas to a patient, including a humidifier case having a hinged lid, a water container adapted for drop-in assembly in said case, a heater in heat transfer communication with said water container, a gas flow path including a gas inlet, a humidified gas outlet and an intermediate gas flow path which contacts the gas with water vapour from said container, wherein said water container has a gas passage inlet communicating with said gas flow path, said humidifier further including a gas passage inlet seal for sealing connection said gas passage inlet to said gas flow path, wherein said sealing connection is actuated by drop-in assembly of said water container and hinged closing of said lid.

Preferably, said gas passage inlet is located on a rear face of said water container and aligns with a gas passage aperture on an opposed face of said case.

A further form of the invention provides, in a humidifier assembly for a flow generator used in delivery of a supply of breathable gas to a patient for treatment of sleep disordered breathing, the humidifier assembly comprising a water tub having an inlet, a base having a blower outlet and a water-tub-receiving-portion, and a hinged lid with an engagable locking mechanism, a method of forming a seal between the water tub inlet and the blower outlet of the base comprising the steps of:

placing the water tub in the tub-receiving-portion of the base so as to position the inlet and the outlet adjacent one another;

closing the hinged lid; and engaging the locking mechanism.

Preferably, the blower outlet includes front-facing seal forming surface, and the step of placing the water tub in the water-tub-receiving portion of the base further includes the step of placing the water tub against the seal forming surface of the blower outlet.

A further form of the invention provides, in a humidifier assembly for a flow generator used in delivery of a supply of breathable gas to a patient for treatment of sleep disordered breathing, the humidifier assembly comprising a water tub having an air outlet and an hinged lid with an engagable locking mechanism and an air delivery portion adapted to mate with an air delivery conduit so that the supply of breathable gas can be provided to a patient interface, a method of forming a seal between the water tub air outlet and the air delivery portion comprising the steps of:

closing the hinged lid; and engaging the locking mechanism.

Preferably, the hinged lid has an underside, and the underside includes a seal forming surface comprising a removably attachable gasket.

A further form of the invention provides a humidifier assembly for a flow generator used in delivery of a supply of breathable gas to a patient for treatment of sleep disordered breathing, the humidifier assembly comprising a water tub having an air inlet and an air outlet, a humidifier base having a blower outlet and a water-tub-receiving portion, and a lid having an air delivery portion adapted to mate with an air delivery conduit so that the supply of breathable gas can be provided to a patient interface, wherein said water-tub-receiving portion and water tub have complementary formations adapted to guide drop-in positioning of said water tub to align said air inlet with said blower outlet.

Preferably, said complementary formations further guide positioning of said water tub to align said air outlet with a position of said air delivery portion of said lid when said lid is closed.

A further form of the invention provides a humidifier for delivering humidified breathable gas to a patient, including a humidifier case having a lid, a water container within said case, a heater in heat transfer communication with said water container, a gas flow path including a gas inlet, a humidified gas outlet in said lid and an intermediate gas flow path which contacts the gas with water vapour from said container, and a gas outlet seal operatively associated with said lid whereby closing said lid creates a sealed communication between said humidified gas outlet the seal and a gas space of said water container.

Preferably, the humidifier further includes a gas passage seal attached to the underside of said lid cooperating with a surface of said water container to form a sealed gas passage between a gas passage inlet and a gas inlet to said gas space.

Preferably also, said gas outlet seal and said gas passage seal are integrally formed.

A further form of the invention provides a humidifier for delivering humidified breathable gas to a patient, including a water container, a heater in heat transfer communication with said water container, a gas flow path including a gas inlet, a humidified gas outlet in said lid and an intermediate gas flow path which contacts the gas with water vapour from said container, wherein said intermediate gas flow path includes a gas passage between a gas passage inlet and a gas inlet to said gas space, said gas passage having a floor sloping downwards from said gas passage inlet to said gas inlet.

Preferably, said gas passage includes a drainage portion below a level of the gas passage inlet, being a forwardmost portion of said gas passage having a front wall below the level of the gas passage inlet.

A further form of the invention provides a humidifier for delivering humidified breathable gas to a patient, including a water container, a gas flow path including a gas inlet, a humidified gas outlet in said lid and an intermediate gas flow path which contacts the gas with water vapour from said container, wherein said gas flow path is adapted to introduce said gas into a headspace of said water container with a swirling motion.

Preferably, said intermediate gas flow path includes a container air inlet adapted to introduce gas generally tangentially into said container headspace.

Preferably also, said intermediate gas flow path includes an arcuate gas flow path leading to said container air inlet, and further includes a container air outlet positioned generally centrally of said headspace.

A further form of the invention provides a control circuit for a humidifier for delivering humidified breathable gas to a patient, including a user operable control for selecting a desired gas humidity setting and a heater control circuit for determining a target heater temperature corresponding to the humidity setting and controlling a heater to attain said temperature, wherein said user operable control includes an off setting for which said heater control selects a target heater temperature less than a lowest operating temperature of said humidifier.

A further form of the invention provides a control circuit for a humidifier for delivering humidified breathable gas to a patient, including a user operable control for selecting a desired gas humidity setting and a heater control circuit controlling a heater current to a value corresponding to the humidity setting, said user operable control including setting a reference voltage in response to said user operable control and amplifying said voltage to control said heater current.

A further form of the invention provides a flow generator for delivering breathable gas to a patient, including a processor, a timer, user input means and a display, said processor being programmed to receive a reminder request input and to generate a reminder display at a time specified in said reminder request input.

Preferably, said processor is adapted to cancel a reminder request upon receiving a cancellation input from said user input means.

Also described herein are improved, modular, devices for enabling data connection with the apparatus, including the connection of data storage devices such as memory cards, smart cards, communication ports and the like to be selectively attached by the user or by medical personnel.

A further form of the invention provides a modular data or electrical connector arrangement for a flow generator unit for delivering breathable gas to a patient, including:

a flow generator case including an aperture;

a gas flow generator;

a control circuit for said flow generator, said circuit including a connector positioned to be accessible through said aperture for data or electrical communication with an external device; and a plurality of closure modules each adapted to attach to said ease to cover said aperture, at least one of said closure modules including an internal connector adapted to connect with said control circuit connector, an external data or electrical port adapted for connection to said external device and a data or electrical pathway between said internal and external connectors.

BRIEF DESCRIPTION OF THE DRAWINGS

The various aspects of the invention will now be described with reference to the accompanying illustrations, which show a presently proposed embodiment.

In the drawings.

DETAILED DESCRIPTION OF PREFERRED EMBODIMENTS

Figure 1:
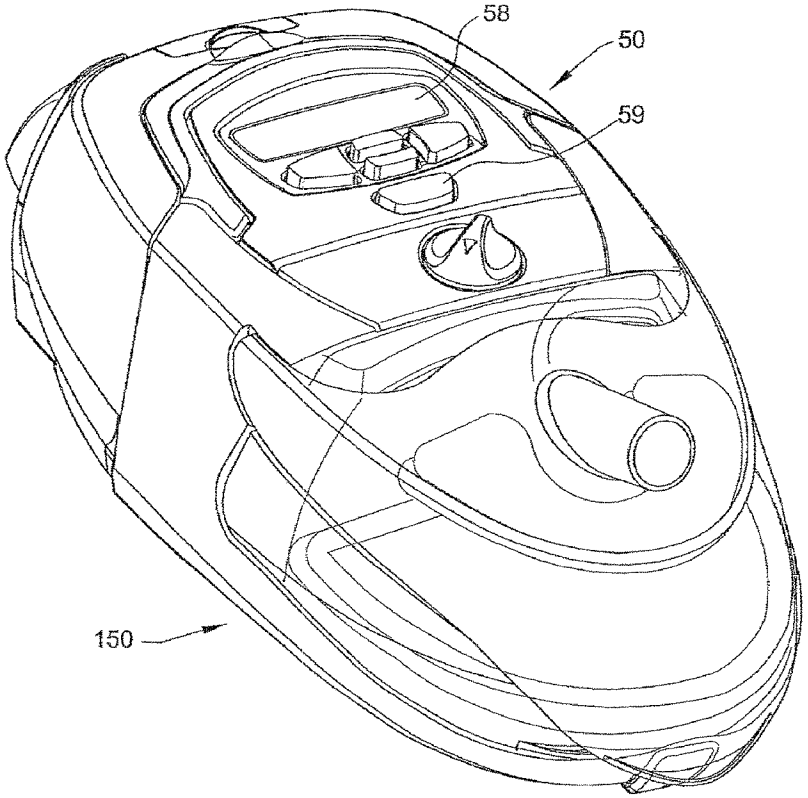
FIG. 1 is a general view of breathable gas apparatus embodying the various features of the invention.
Figure 2:
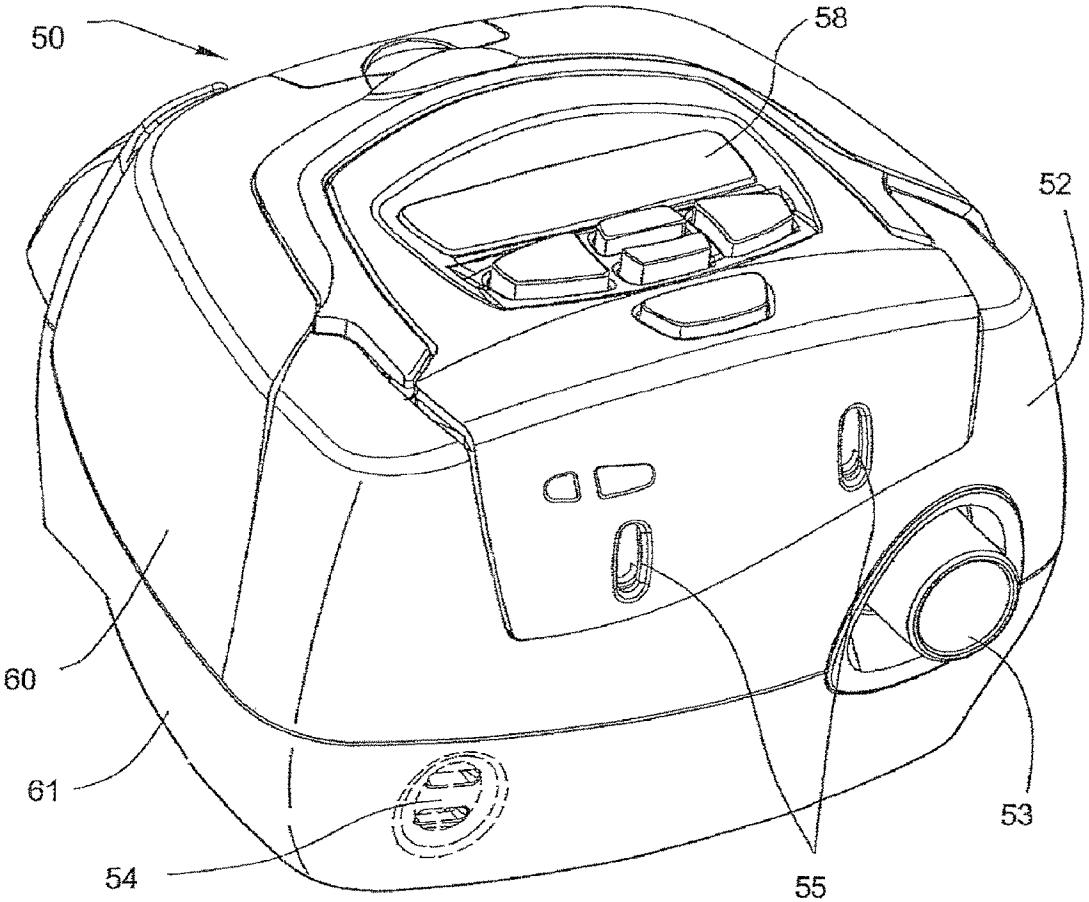
FIG. 2 is a general view of the flow generator of the apparatus.
Figure 3:
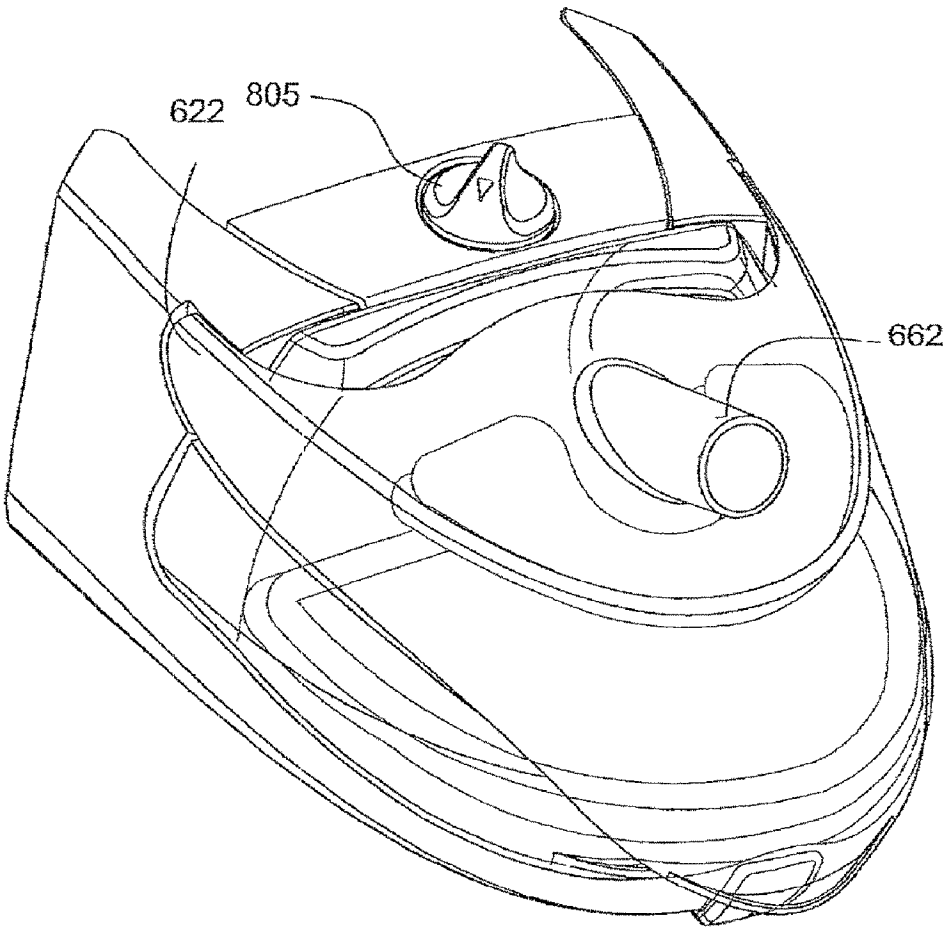
FIG. 3 is a general view of the humidifier unit.
Figure 4:
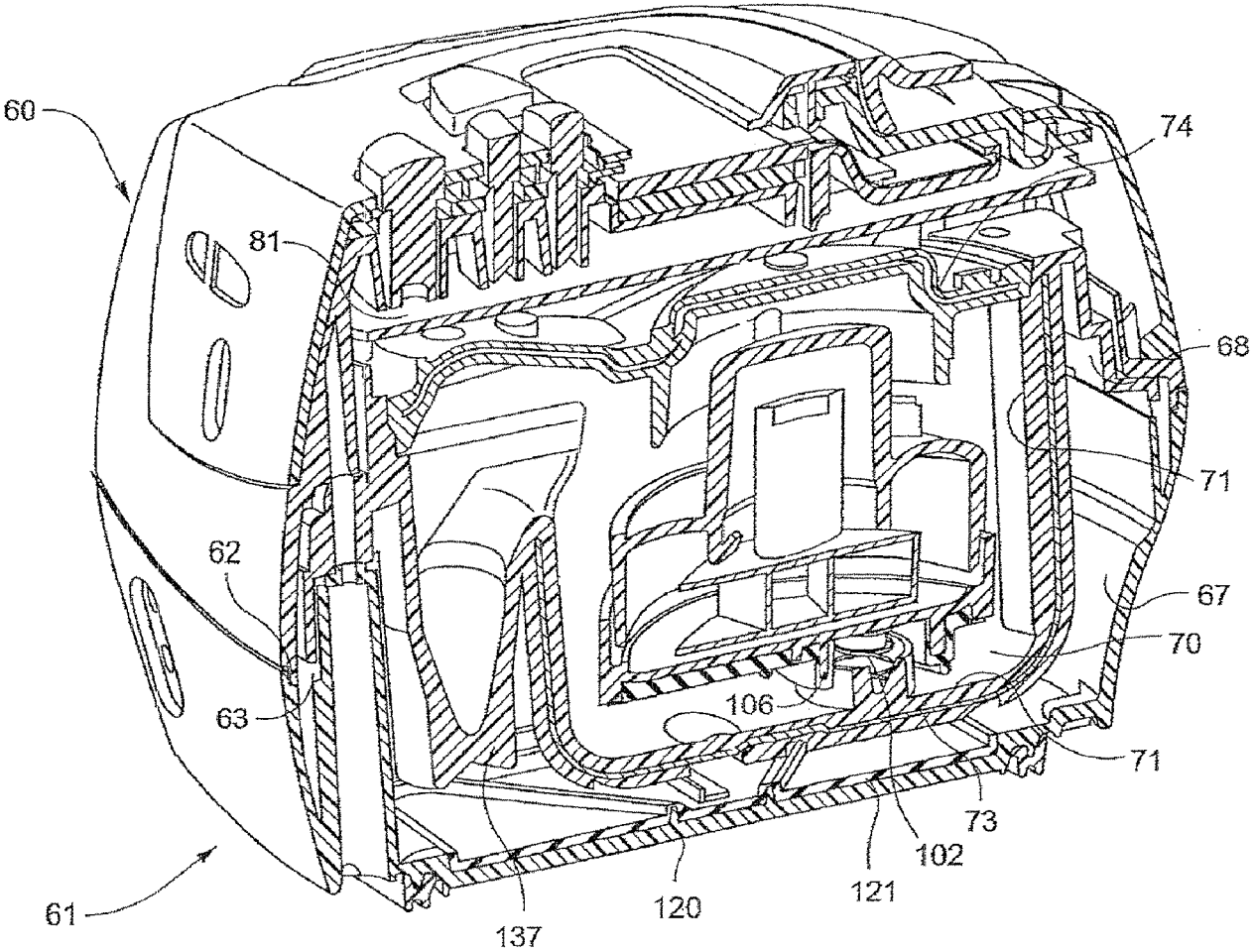
FIG. 4 is a cutaway view of the flow generator.
Figure 5:
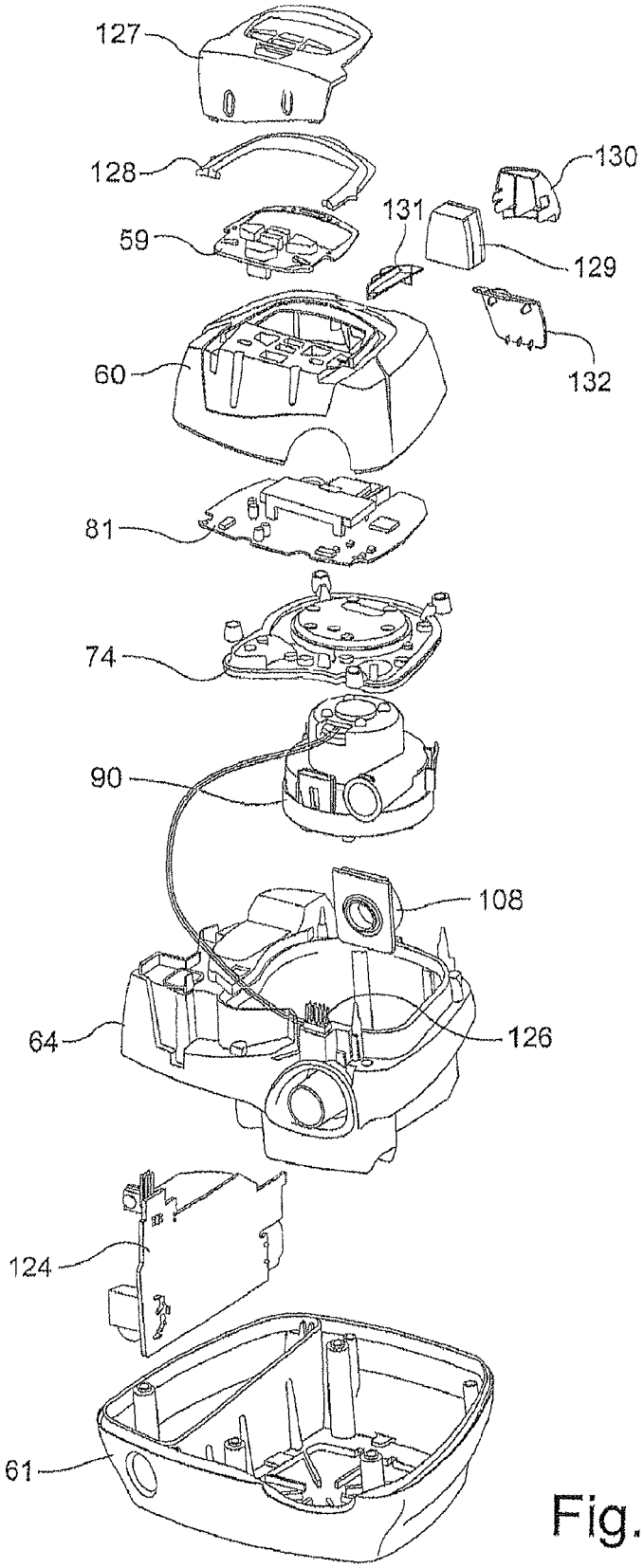
FIG. 5 is an exploded view of components of the flow generator.

The illustrated apparatus comprises a flow generator 50 and a humidifier 150, shown in their assembled condition in FIG. 1, and separately in FIGS. 2 and 3 respectively. As shown in FIG. 2, the flow generator engages with the separable humidifier at an engagement face 52, from which protrudes an air connector 53 for the delivery of air from the fan to the humidifier container, electrical connectors 54 for the delivery of power to the humidifier heater and an optical coupling transmitter 200 and sensor 201 described further below.

Figure 15:
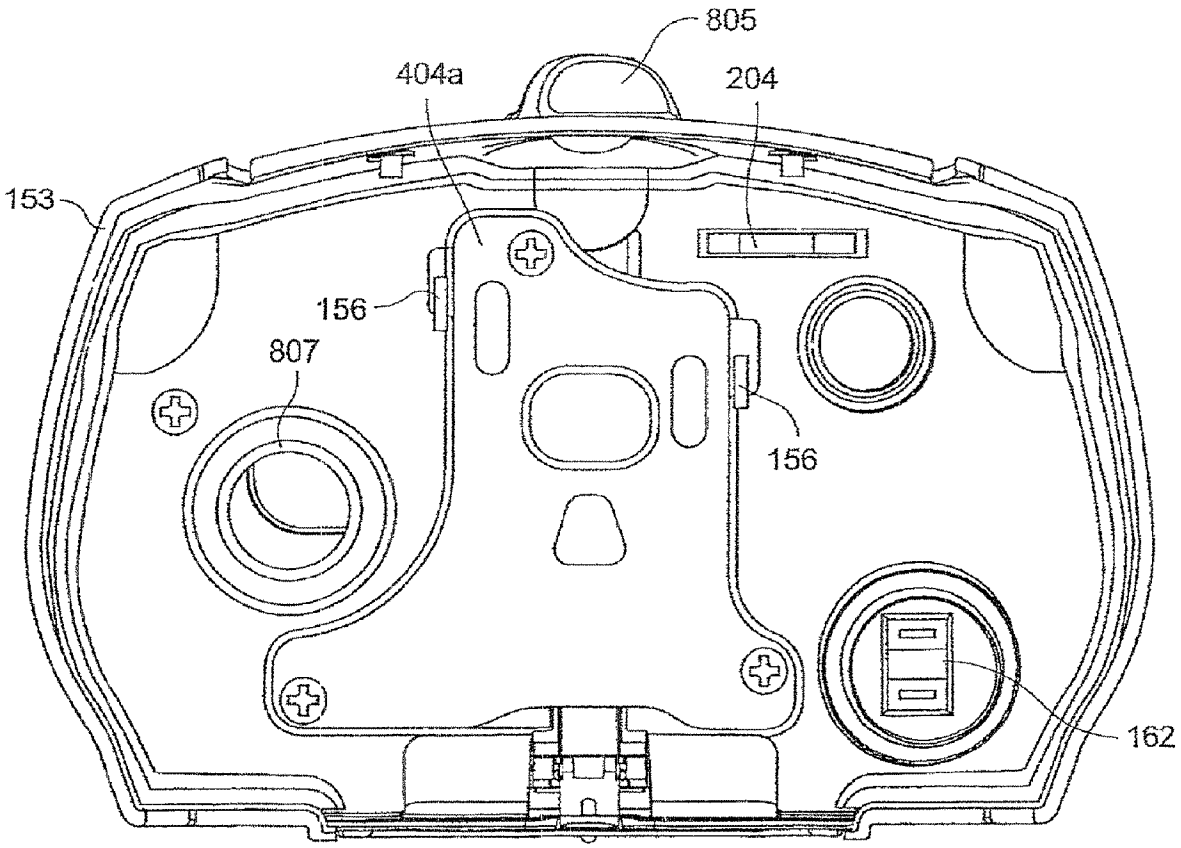
FIG. 15 is a rear view of the humidifier assembly.
Figure 16:
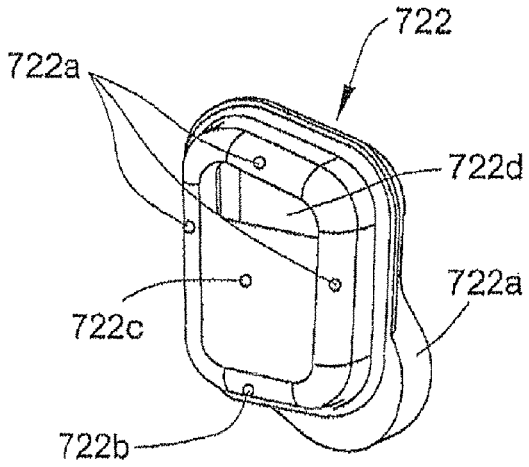
FIG. 16 is a perspective of a seal for the air flow path.

The face 52 also carries a pair of slots 55 which are engaged by corresponding tongues 156 provided on the humidifier engagement face 157 (FIG. 15) by which the flow generator 50 and humidifier 150 are connected together, as will be described in more detail below.

Flow Generator

Externally, the flow generator 50 is also provided with an LCD screen 58 and associated keys 59 by which the user can set the operating parameters of the unit.

Flow Generator Case

The flow generator 50 has an external case of rigid plastics material moulded in two parts, a top case 60 and a bottom case 61. The lower edge of the top case 60 is stepped and flanged at 62 (FIG. 9) to mate with the periphery of the bottom case 61.

Figure 6:
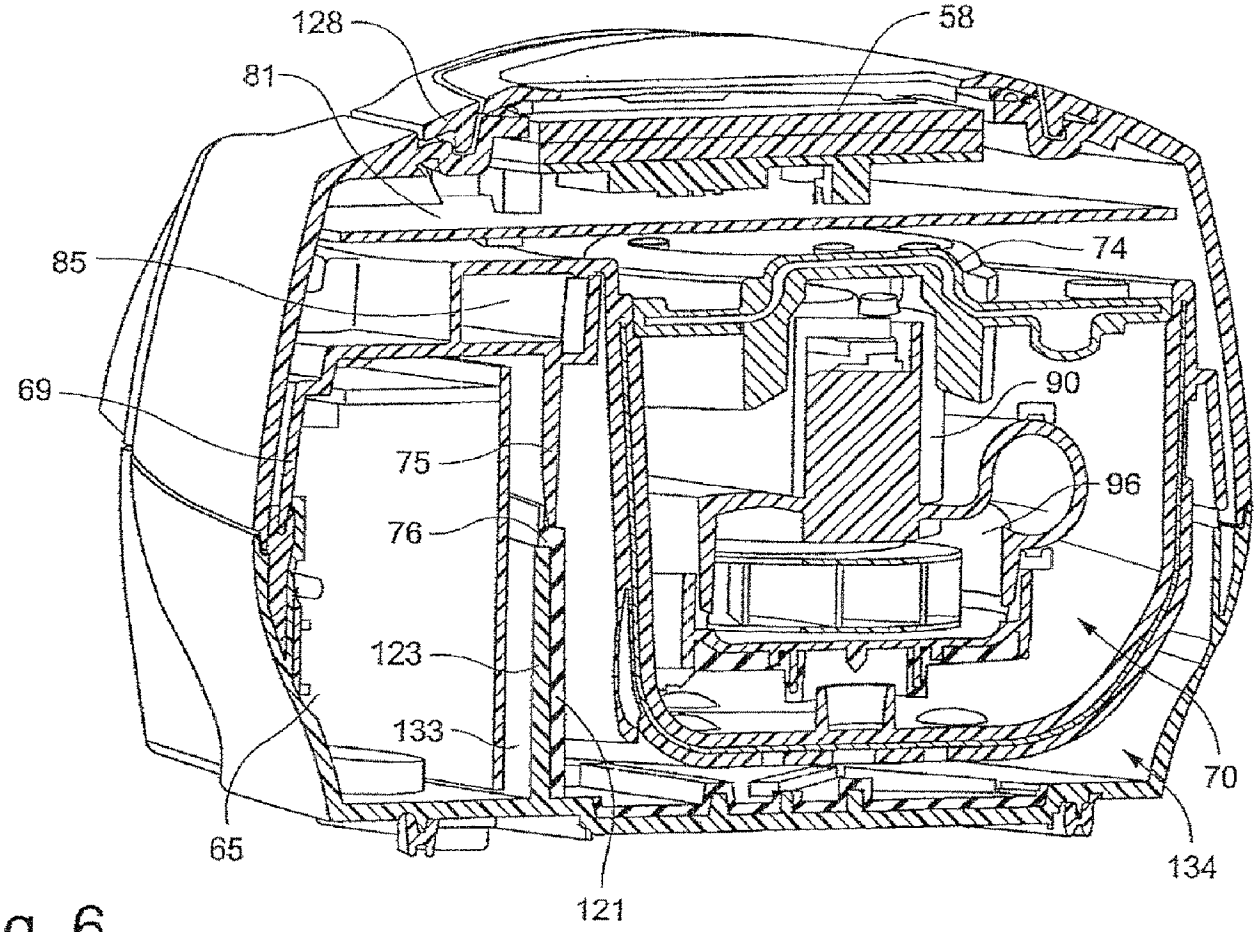
FIG. 6 is a vertical transverse cross-section of the flow generator.
Figure 7:
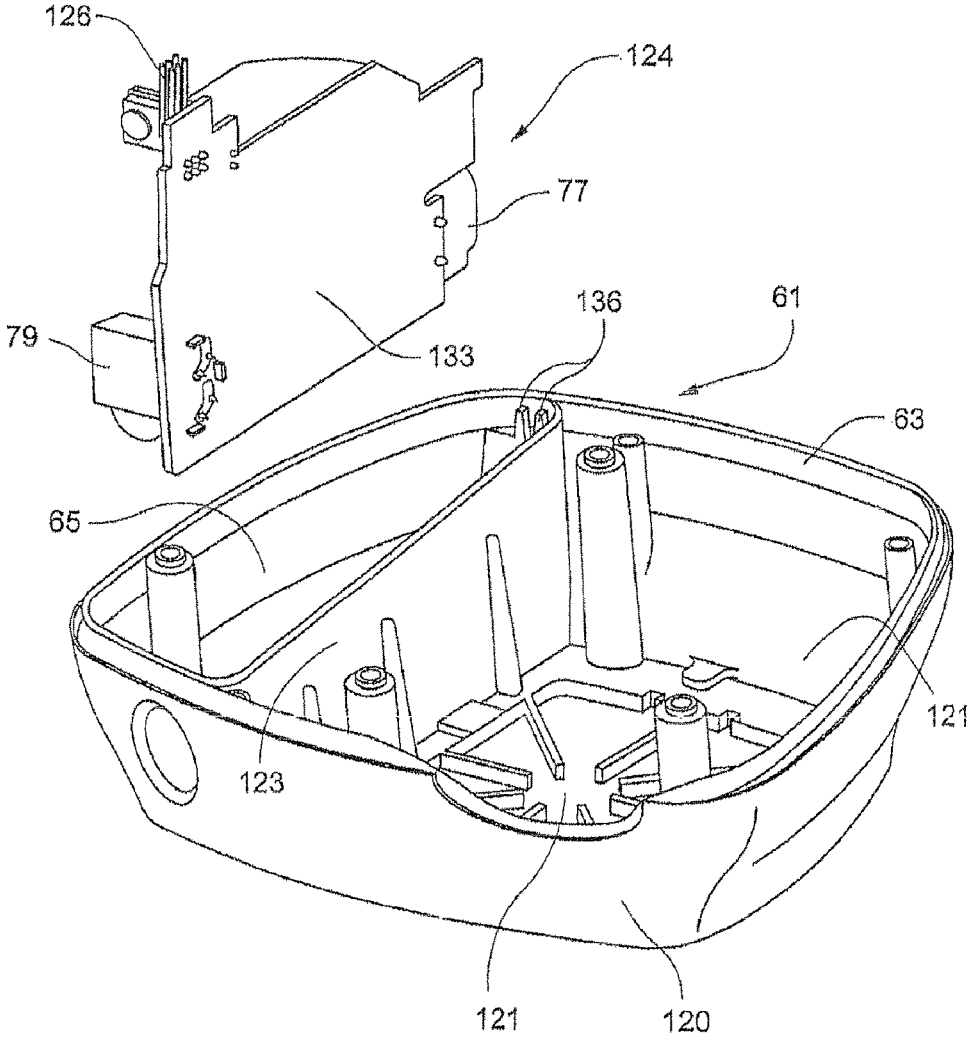
FIG. 7 is a more detailed illustration of the bottom case and power supply of FIG. 5.

With reference to FIG. 7, the bottom case 61 of flow generator 50 has a shell 120 of rigid plastics material, such polycarbonate/ABS blend, forming the structure of the case, integrally overmoulded with a lining 121 of an elastomer such as a synthetic rubber or thermoplastic elastomer which forms the seal 63 between the top and bottom cases and the chassis 64 and also forms the external feet of the case (see FIG. 6). The lining 121 also covers the internal surface of the chassis-receiving cavity of the bottom case and the dividing wall 123 between the power supply cavity 65 and chassis-receiving cavity, the resulting composite of the rigid shell with elastomeric lining serving to reduce radiated noise levels from the flow generator by damping acoustic resonance of the walls.

Formed in the bottom case 61 by walls which join the outer wall of the case are the lower parts and of, respectively, a power supply cavity 65 and a first muffler cavity 134. The upper parts of these cavities are formed by the chassis 64, described below.

The first muffler cavity forms part of the air flow path from the air inlet 85 to the blower, receiving air from an air inlet path defined by the chassis 64, as described below.

The chassis 64 forms the blower or fan cavity 70, inlet and outlet air flow paths and the top of the power supply cavity 65. The fan cavity 70 includes a metal liner tub 73 insert moulded into the chassis as described below.

Flow Generator Chassis

The chassis 64 is formed with a peripheral wall 69 tinged around its lower edge to engage with the inner periphery of the overmoulded sealing flange 63. The chassis 64 includes a downwardly extending fan cavity 70 in which is mounted the fan 90 described below. This cavity 70 is formed by moulded side walls 71 and base 72, which are formed by moulding inner and outer layers of thermoplastic around an inserted steel liner tub 73. The tub may be stainless steel, nickel plated mild steel or other suitable corrosion resistant metal. The fan cavity 70 opens to the upper surface of the chassis 64 to enable insertion of the fan 90, this opening being closed by a lid 74.

The density and stiffness of the steel tub creates a highly effective barrier to transmission of the motor and fan noise, while formation of the cavity 70 by insert moulding from differing materials provides very effective acoustic damping, as does the combination by co-moulding of the hard and soft plastics described already and further described below. In this aspect of the present invention, the use of co-moulding or overmoulding in the combination of materials of different, preferably widely different, stiffness and different, preferably widely different, density has been found to be particularly advantageous in providing acoustic damping.

Preferred materials for the chassis and liner tub are polypropylene thermoplastic for the chassis and metal, preferably steel (optionally stainless steel), for the liner tub. The applicant has found that by forming the fan cavity as a composite of metal and polymer—having a differential in density of greater than 5 times, preferably about 7-8 times, and also significantly different stiffness and damping properties—the resonance peaks of the composite structure are well damped so that noise generated by the fan is well-suppressed by the fan cavity construction.

It is especially preferred that the polymer for the chassis 64 be a glass fibre-filled polymer containing from 10-40%, and more preferably about 30%, glass fibre. The Applicant has found that the use of this material as a composite with a steel liner tub 73 gives both effective damping of fan noise and a good match in thermal expansion characteristics so that the composite material chassis performs well over a wide range of operating temperatures. Further, the Applicant has found that the use of glass fibres outperformed talc, bronze, glass bead filler materials for this purpose.

The top of the fan cavity is formed by the chassis lid 74, which is formed of an embedded steel insert overmoulded with elastomer to provide acoustic damping and sealing of the top of the fan cavity 70 A preferred polymer lining for the lid is an elastomer, for example of the same type used for the lining 121 of the bottom case.

Again, the use of a steel and polymer composite creates an effective and well-damped barrier to transmission of fan and motor noise.

Drop-In Power Supply

The upper part of the power supply cavity 65 is formed by a side wall 75 extending downwardly from the roof of the chassis 64, which sealingly engages the opposed wall of the lower portion of this cavity. Preferably, the lower wall is provided for this purpose with a co-moulded or overmoulded rubber sealing flange 76. The power supply compartment is thus sealed against the ingress of moisture from the interior of the unit in the case of backflow from the humidifier. Similarly, the air path is sealed from the power supply compartment. The interior is at the same time acoustically sealed from the power supply cavity, which may not be completely sealed from the exterior, due to the necessity of providing mains power input and low voltage power output to the humidifier, via connectors 77 and 79 mounted in apertures 78 and 80 respectively in the rear and front walls of the cavity, and if necessary the venting of the compartment to outside air for cooling. This reduces assembly time and allows the overall device to be smaller.

With reference to FIG. 7, a power supply unit 124 is received in the power supply cavity 65, for providing electrical power for operation of the fan, control functions and the humidifier heater pad. The power supply comprises a printed circuit board 133, to which are directly attached by soldering or other suitable means a power inlet connector 77, a fan power outlet connector 126 for the fan motor and a humidifier power outlet 79. Each end of the power supply cavity 65 has mounting guides 136 for supporting the PCB of the power supply in an upright position so that installation of the power supply is achieved by drop-in assembly. By rigid attachment of the connectors by soldering direct to the PCB, the need for connection of wiring looms to the PCB is eliminated and the connectors align with respective ports in the bottom case 61 when the power supply is inserted.

PCB

Figure 8:
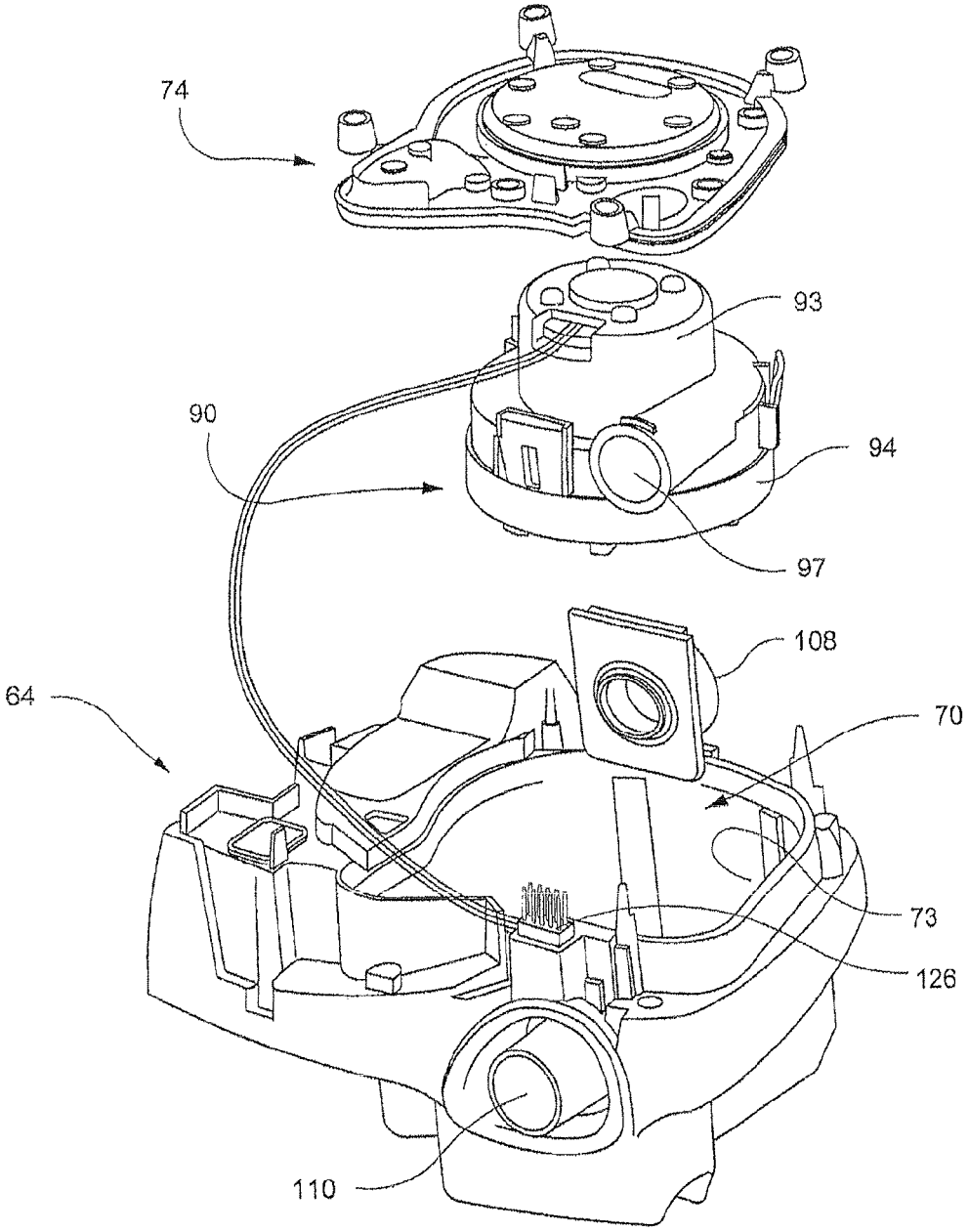
FIG. 8 is a more detailed illustration of the chassis, chassis lid and fan housing of FIG. 5.

With reference to FIG. 8, the fan 90 and fan housing 93, 94 fit into the fan cavity 70 of the chassis and connect to electrical connector 26 at the top of the power supply PCB. Elastomer overmoulding of the base 94 of the fan housing seals the housing, provides acoustic damping of the fan housing base and forms feet on the bottom of base to act as bump stops protecting the fan in case the unit is bumped or dropped.

Figure 9:
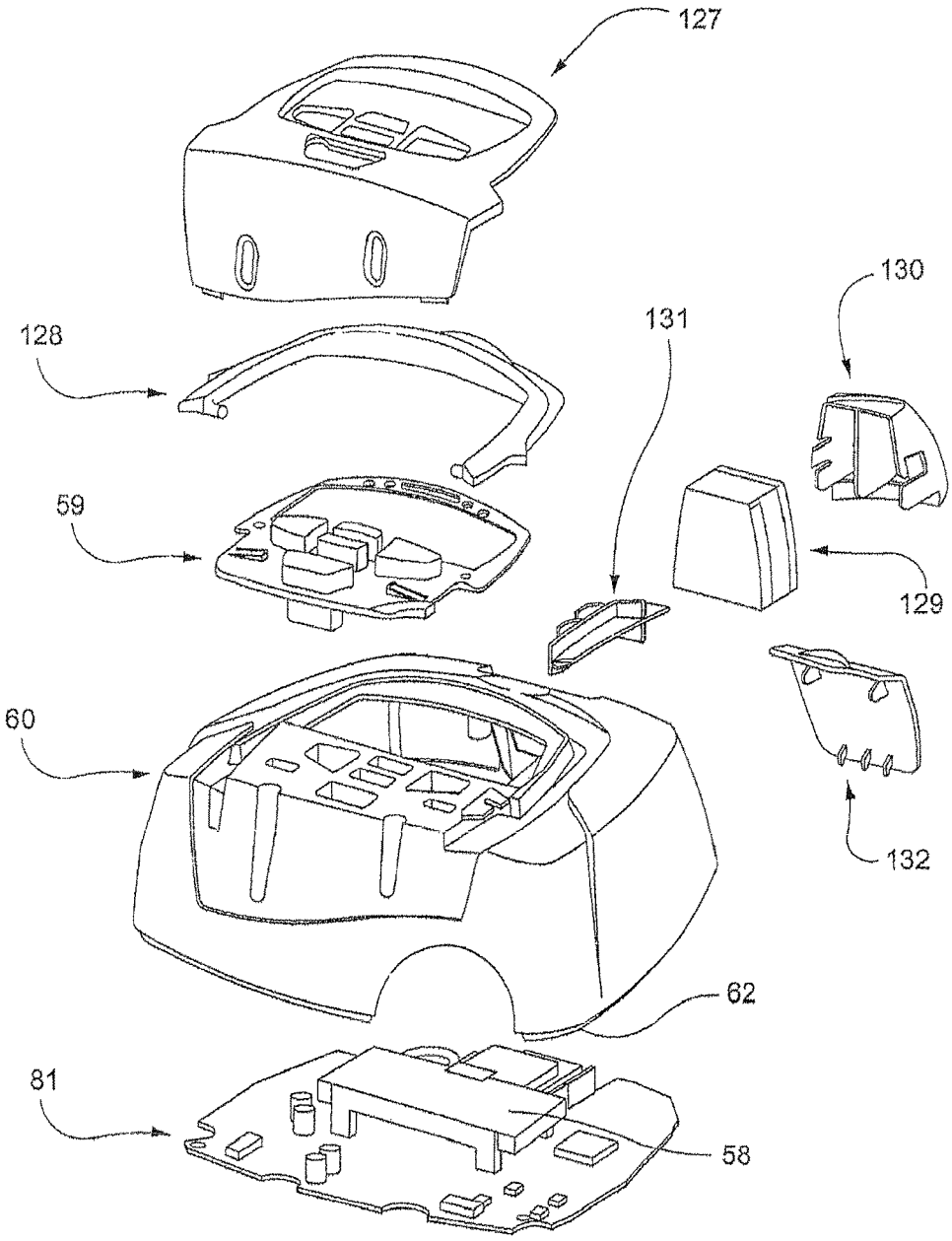
FIG. 9 is a more detailed illustration of the PCB, top case and exterior fittings of FIG. 5.

As shown in FIG. 9, supported on the top of the chassis 64, in the space formed between the chassis and the top of the top case 60, is a printed circuit board 81 carrying the electronic control components of the unit. The printed circuit board 81 preferably includes an LCD display 58. Optionally, at the rear of the board an edge connector 1082 and a sliding connector 1082A may be accessible from a connector aperture in the rear of the case 60, providing for modular connector arrangements to be described in more detail below with reference to FIGS. 25 to 34.

Air Inlet Path and Mufflers

Also provided in the rear wall of the top case is an air inlet 84, and this communicates with an air inlet passage 85 formed in the chassis above the roof of the upper portion of the power supply cavity 65, this passage in turn opening to first muffler cavity 134 surrounding the bottom of the fan cavity of the chassis.

The top case further defines an air inlet to the flow generator, and has a replaceable filter 129 of any suitable material, such as foam or fibre, and filter cover 130 fitted to the top case 60. An inlet wedge 131 serves as an airflow guide. A blank cover 132 clips in place over apertures in the case which align with connectors 1082, 1082A to provide ports on the PCB for communications, etc. Further details of the communications and/other electrical ports in the flow generator case will be described later with reference to FIGS. 25 to 34.

From the first muffler volume 134 under the fan cavity 70, inlet air passes through a connection passage 137 (FIG. 11) into a second muffler volume formed by the space between the fan cavity 70 and the fan.

The fan cavity and the space between the bottom case and the chassis thus form a pair of serially connected volume mufflers, with a restricted diameter passage therebetween. Noise attenuation produced by a muffler system is generally proportional to the ratio of a representative diameter of the muffler volume to that of the constriction, and thus an optimal muffler design must balance optimal noise attenuation against the constraints of available muffler volume—especially in a compact machine—and avoiding unacceptable air flow restriction through the constriction.

Figure 10:
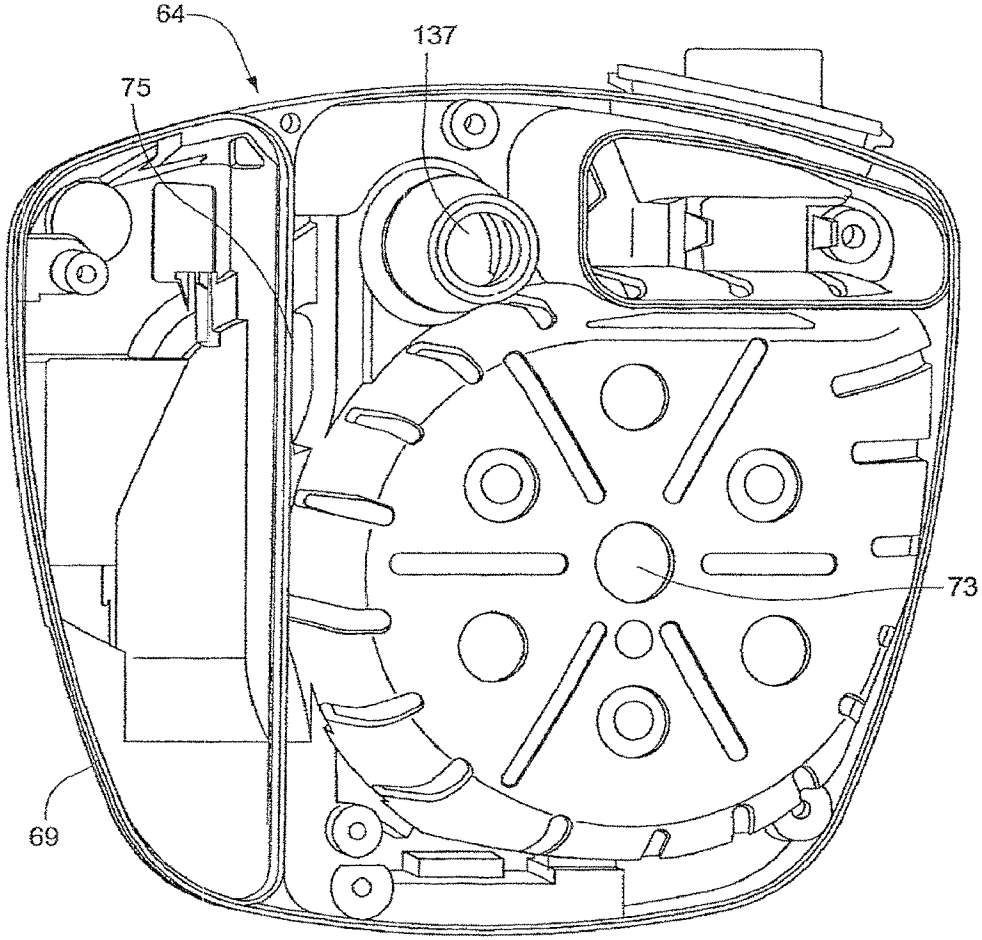
FIG. 10 is an underneath view of a chassis forming part of the flow generator.
Figure 11:
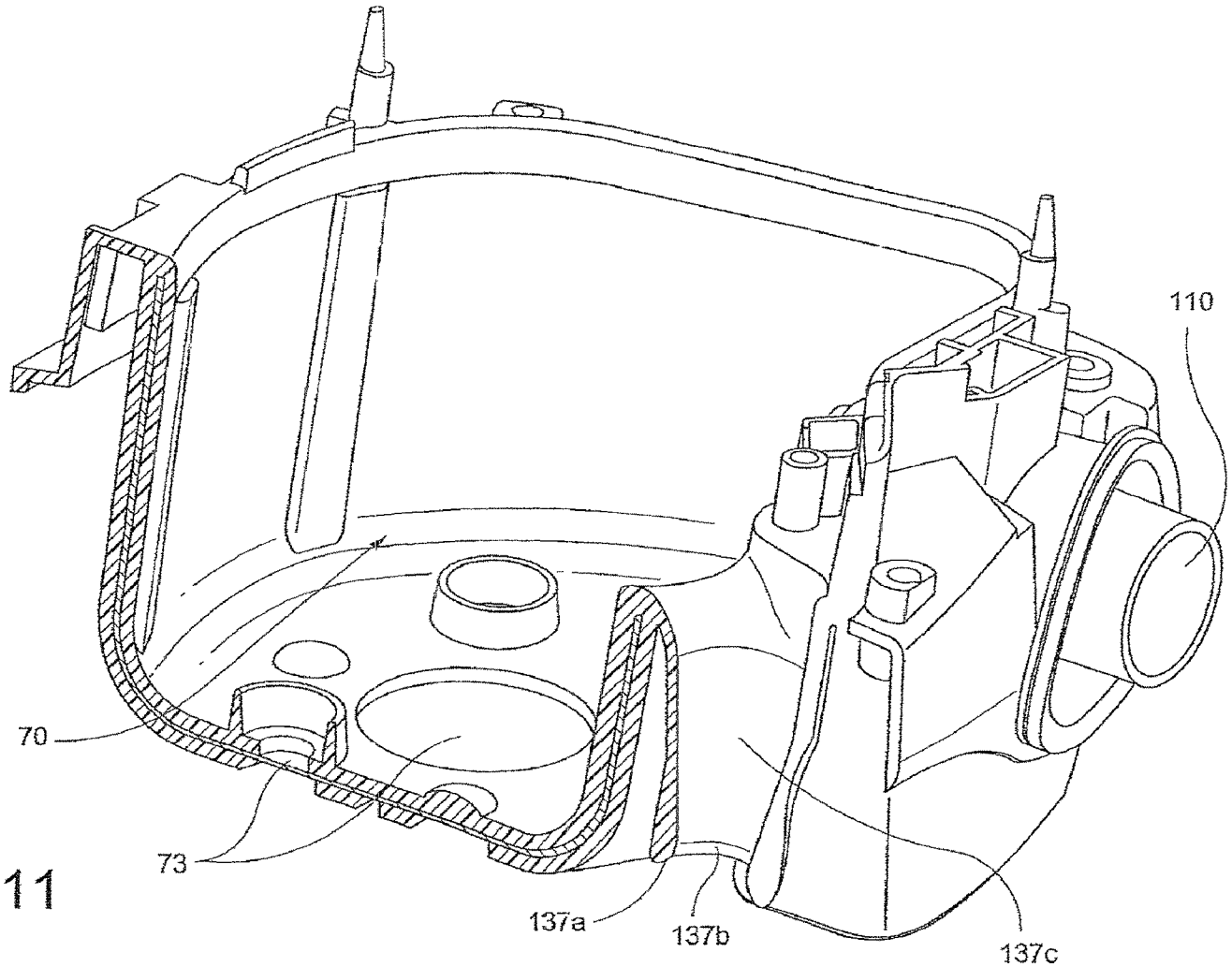
FIG. 11 is a vertical cross-section of the chassis through a venturi passage connecting muffler cavities of the flow generator.

The Applicant has found that a favourable adjustment of this balance may be achieved by forming the intermediate connecting passage 137 between the muffler volumes as a venturi, as shown in FIGS. 10 and 11, with a relatively short, smoothly varying diameter lead in portion 137a at the end adjacent the first muffler, an intermediate constriction 137b and a gradually expanding lead out portion 137c at the downstream end. In this way, the muffler system can achieve the noise attenuation according to the representative diameter of the smallest diameter portion, with better pressure drop characteristics.

Fan

Figure 12:
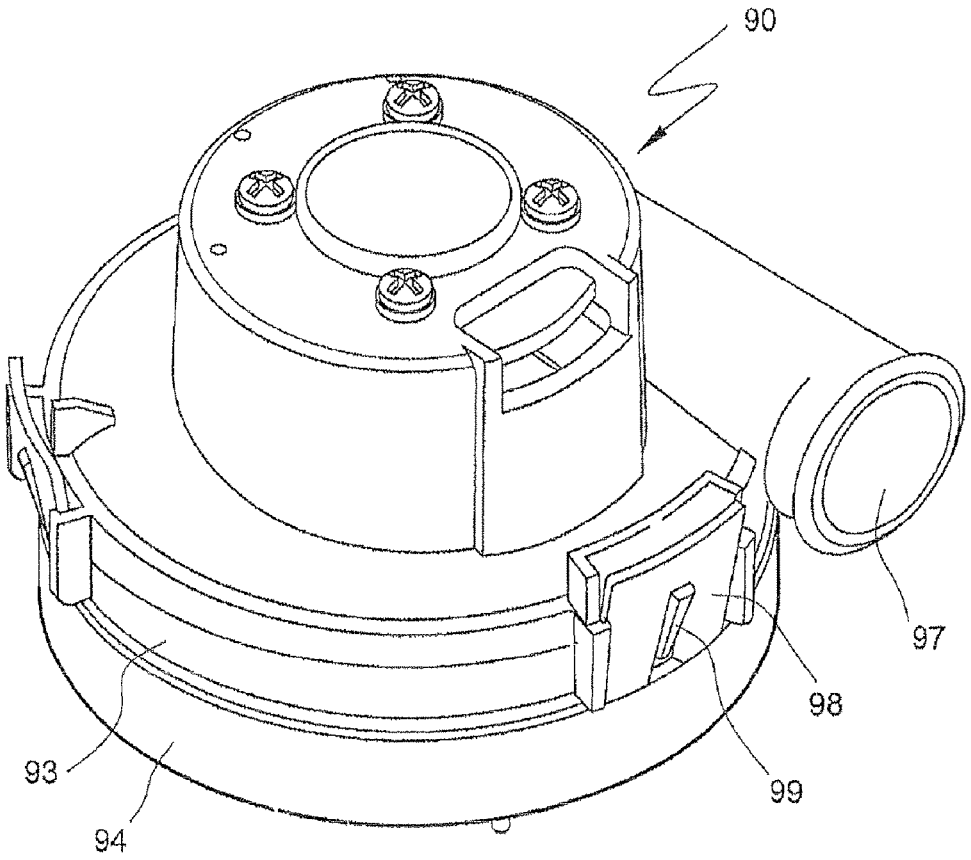
FIG. 12 is a general view of a fan forming part of the flow generator.
Figure 13:
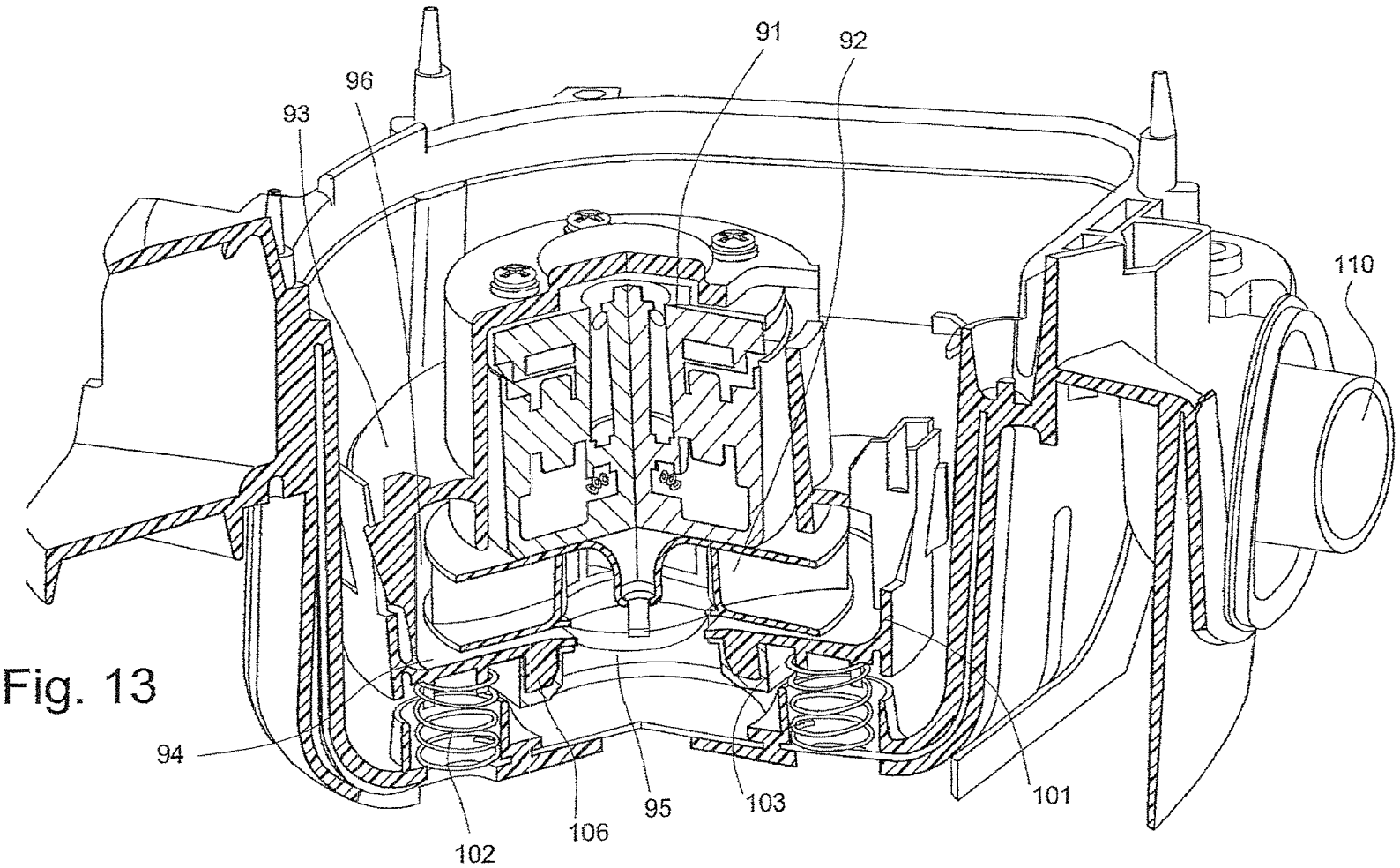
FIG. 13 is a vertical cross-section showing the fan mounting arrangement.
Figure 14:
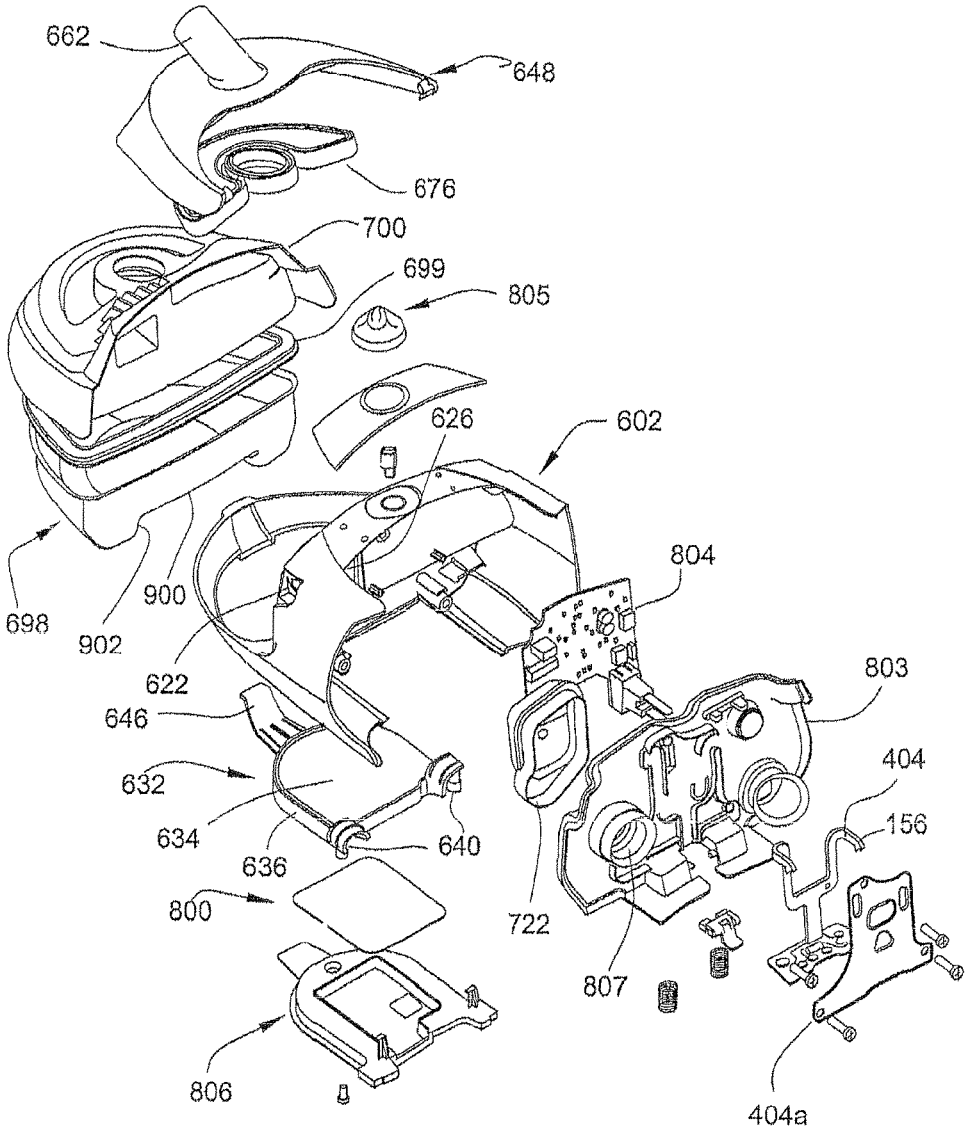
FIG. 14 is an exploded view of a humidifier adapted for use with the flow generator of FIG. 5.

It will now be convenient to describe the features of the fan, which are shown in FIGS. 12 and 13.

The fan 90 comprises a motor 91, preferably brushless DC motor, provided with a coaxial impeller 92, mounted vertically within a fan housing consisting of a cover 93 and a base 94. An air inlet 95 is provided in the floor of the base 94 on the impeller axis, and cavities in the cover and base form a volute 96 which leads from the impeller to an air outlet 97. The cover and base 93 and 94 are joined by means of slotted tabs 98 which extend upwardly from the base to snap over stepped ribs 99, the tabs 98 being further located by fitting between parallel ribs on the cover 93. The joint between the cover 93 and the base 94 is sealed by an elastomeric over- or co-moulded sealing ring 101.

The bottom surface of the fan housing base 94 is provided with radial stiffening ribs, and overmoulded to the base 94 is an elastomer damping member 103 which covers that bottom surface between the ribs, and extends around the edge of the base by a flange portion and peripherally spaced tabs. By overmoulding to the rigid plastics base 94 an elastomer of much lower stiffness substantial acoustical damping is provided to the fan housing.

Moulded integrally with the rigid plastics portion of the fan housing base are feet 106 which extend proud of overmoulded elastomer member 103 to receive helical mounting springs 102 (FIG. 13), preferably of metal, by which the fan is mounted on the base 72 of the fan cavity.

The degree of size reduction which is an objective of the present invention requires great care to be taken to minimise the transmission of noise and vibration, particularly from the motor and the impeller of the fan 90. The mounting springs are therefore chosen to ensure minimal transmission of the vibration frequencies encountered during operation. This is achieved by choosing the springs with reference to the mass of the fan 90, such that the natural frequency of the system comprising the springs and the fan is less than approximately one tenth of the shaft speed of the motor when running at its lowest operating speed.

The air outlet 97, upon the introduction of the fan into the fan cavity, is connected by means of a thermoplastic elastomer or silicone rubber coupling member 108 with an air passage which extends from the side wall of the fan cavity to a connecting nozzle 110 extending through an aperture provided for this purpose in the front face of the flow generator. It is preferred that the coupling member 108 includes at least two corrugations which provide flexibility to the connection and improved resistance against transfer of vibration from the fan to the flow generator case.

The fan 90 therefore floats within its cavity 70 in the chassis 64 with minimum acoustic coupling to the remainder of the flow generator. The characteristics of the mounting springs and the coupling member 108 are chosen to minimise the transmission of characteristic vibration frequencies of the fan.

Further details of the fan construction and fan mounting are described in US20030168064 and WO99/64747, the contents of which are incorporated herein by reference.

The illustrated flow generator construction and materials combinations are adapted to result in a compact CPAP flow generator unit of similar performance and noise characteristics to larger units—eg. capable of generating from 4-20 $cmH_2O$ pressure and a flow rate of 120 L/min and a total radiated noise volume of less than 33 dbA, more preferably less than about 30 dbA, when operating at 10 $cmH_2O$—in a flow generator unit having a total volume of about 2 litres or less.

Handle Attachment

A keypad 59, facia 127 and transport handle 128 attach to the top case 60.

Figure 9A:
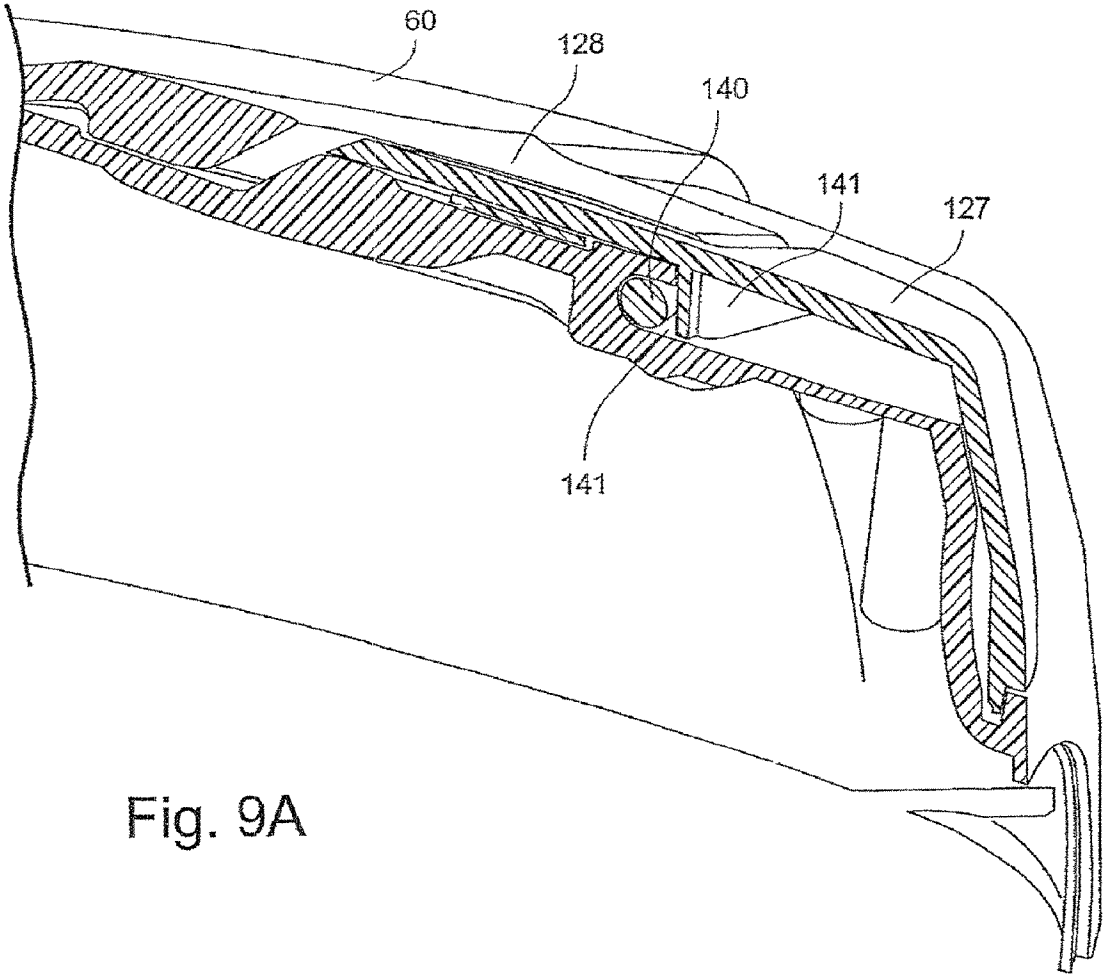
FIG. 9A is a schematic vertical cross-section detail of the connection of the handle to the flow generator top case.

With reference to FIGS. 9 and 9A, a novel and easily assembled handle attachment assembly is described and shown. The handle 128 has opposed arms with inwardly projecting pins 140 at their distal ends. The top case 60 includes a pair of channel-shaped tracks 141 with one open and one closed end, for receiving respective of the pins. To assemble the handle to the top case, the pins are inserted from the open ends of their respective channels and slid toward the closed ends. The facia 127 clips onto the top ease 60, and includes projections 142 which trap the pins 140 in the end of their tracks 141.

The handle attachment configuration thus provides a quick and simple means of assembly without requiring flexing of the handle arms to locate the pins into small recesses as in the prior art.

Humidifier

As shown in FIGS. 14 to 21, the humidifier 150 comprises a base unit designed for simple attachment to and detachment from the flow generator 50, which forms a cradle for a water container which is in turn attachable to and detachable from the base unit.

The general arrangement of the humidifier components includes a base (rear cover 803 and front cover 602) onto which is fitted a heater comprising a heater plate (plate 632 with ceramic heater pad 800) which supports a water tub (tub base 698, seal 699 and tub lid 700) and a hinged humidifier lid 648 which seals against the tub lid 700 to form an air path into the tub through the tub lid.

The rear face of the base has a peripheral flange 153 which seats in a corresponding peripheral recess 113 surrounding the front face of the flow generator 50 when the two units are brought together by linear movement towards each other. A latch 404 is held in place by latch retainer 404a to be moveable vertically and resiliently urged downwardly by spring 404b, so that the tongues 156 engage in the slots 55 and snap home to engage the two units by means of the downwardly extending fingers 158 at the ends of the tongues.

Coupling of Flow Generator and Humidifier

The PCB of the flow generator is provided at the end adjacent the humidifier with an optical transmitter 200 which emits a periodic flash of light from the end face of the flow generator case, and an optical sensor 201 to detect the presence or absence of the humidifier. The rear face of the humidifier contains a curved reflector 202 which, when the humidifier is attached to the flow generator, completes an optical path from the transmitter to the sensor so that the flow generator PCB detects the presence of the humidifier and may adjust the control algorithms accordingly.

The rear face of the base unit also carries a connector 162, in this embodiment a pair of flat male blade connectors, for engagement with a mating connector 114 on the front face of the flow generator, to provide power to the humidifier heater from the power supply in the power supply cavity 65. Although not shown in the illustrated embodiment, the respective faces may also carry further interconnecting devices, where other electrical or data connections are required to be established between the flow generator and the humidifier or downstream devices including the air conduit or the mask. Such devices may take the form of optically coupled devices, or connectors of other suitable kinds.

The use of such an opto-coupling connector enables the implementation of a simple protocol for communications between the flow generator and the humidifier. For example, the current flow levels of the flow generator can be sent to the humidifier controller which then adjusts the operation of the humidifier according to a predetermined algorithm.

In the humidifier construction, the back cover 803 which its to the real of the front cover 602 provides the air, electrical and communications connections to the flow generator and provide support for a control PCB 804 and the catch assembly. The catch assembly includes a latch 404 which is retained by a latch retainer 404a and spring 404b, and operates to attach the humidifier to the flow generator generally as described for the earlier embodiments. A control knob 805 on the top of the front cover 602 is connected to the PCB 804 to allow patient control over the degree of humidification.

There is also provided an aperture 264 (FIG. 15) for electrical connections between the humidifier and the flow generator, or for electrical and signal connections to the humidifier.

The air port 807 in the humidifier rear face mates with the outlet 110 of the flow generator.

An elastomer airway seal 722 fits between the front and back covers to connect the air port 807 in the back cover 803 to the aperture 626 of the front cover 602. The seal (shown in more detail in FIG. 16) has an inlet connector portion 722a which connects to the flow generator output via the air port 807 formed in the back cover 803, and a peripheral seal portion 722b which extends about the aperture 626 periphery at the front face of the cover 602. A wall portion 722c of the seal closes off a lower part of the aperture 626, leaving a smaller aperture 722d defined by the seal.

As a result, the airway seal 722 defines a closed passage from the circular air port 807 to the rectangular aperture 722d in the vertical wall of the front cover.

Heater Pad

The heater pad comprises lower and upper parts 806, 800 and a heater pad cover 632.

The heater pad cover 632 has an upper heating surface 634, a downwardly extending peripheral wall 636 acting as a further heating surface and a rear flange with a pair of attachment portions 640 for attachment of the heater pad to tubular protrusions 628 on the rear of the front cover 602.

The heater pad cover 632 is configured to accommodate, below the upper wall 634 and within bounds of the wall 636, a heater pad or other heating means such as an induction heater, for causing heating of the water in the humidifier water container.

The front of the heater pad cover 632 has a forwardly extending tab 646 of dog-legged shape, which extends to the front of the humidifier cradle front cover 632 to support the heater and also provide a catch for the humidifier lid 648.

Water Tub

The water container consists of a water tub 698, seal 699 and tub lid 700.

The floor of the tub 698 is of complementary shape to the heater pad, and is formed of metal or other material suitable to conduct heat from the heater pad to the water in the tub. The floor has a generally horizontal portion 900 corresponding to the upper heating surface 634 of the heater pad and a U-shaped portion below the level of the heater pad upper surface, including a generally vertical heat transfer portion 902 below the horizontal portion corresponding to the peripheral heating surface. When the water container is placed in the humidifier cradle and the hinged lid 648 closed, the water tub base is held in close contact with the heater pad to transfer heat into the water in the tub.

By providing a part of the water tub volume and heat transfer surface about the periphery of the heater pad, a similar water volume and heating area to those in prior art humidifiers can be obtained in a more compact assembly.

Figure 20:
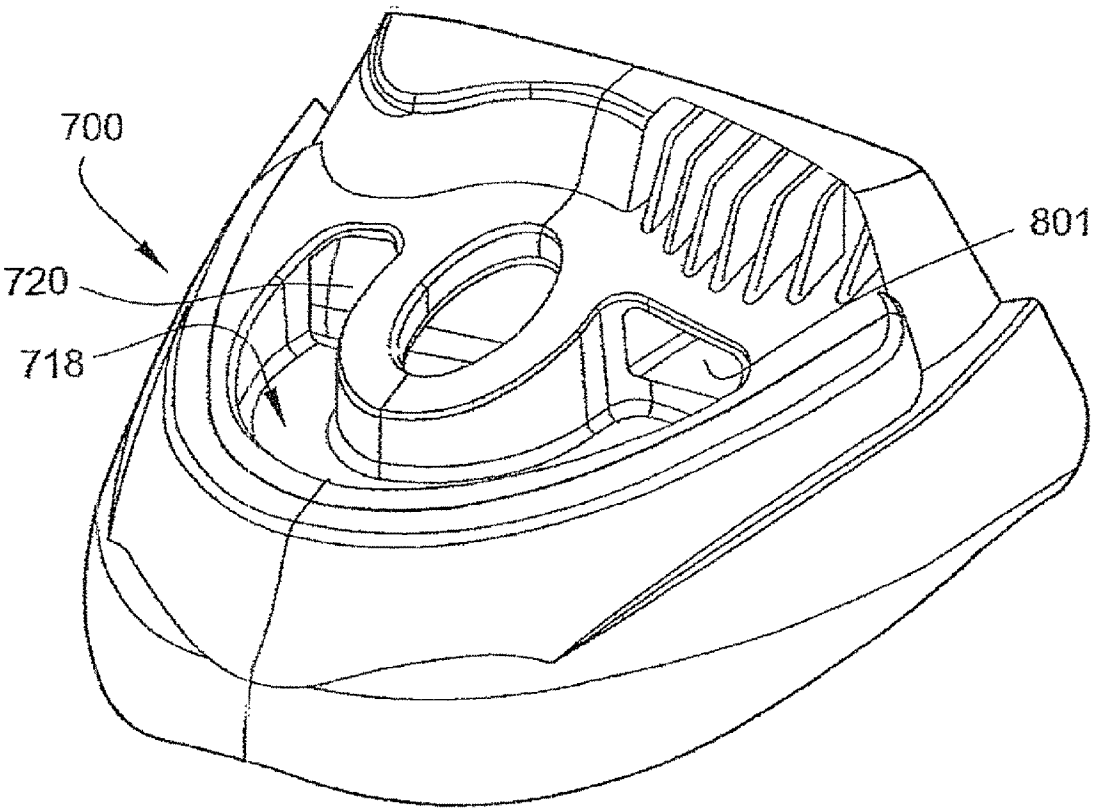

As shown in FIG. 20, the rear surface of the tub lid has an air inlet aperture 801 leading to an inlet end of the U-shaped air passage 718. When the humidifier lid 648 is closed, the tub 698 and tub lid 700 are pressed rearwards so that the peripheral seal 722b abuts the rear surface of the tub lid in a locus surrounding the rear opening of the inlet aperture 801, creating a sealed air path from the flow generator outlet to air passage 718 and into the headspace of the humidifier tub. This allows the humidifier tub to be removed for refilling and replaced without the need for a separate operation to connect the air flow.

Figure 21:
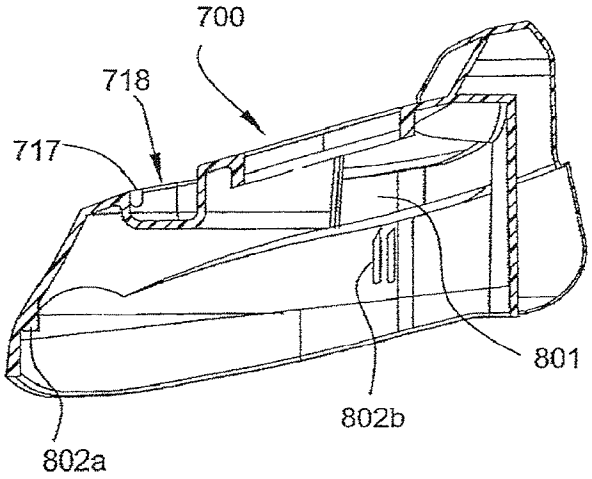
FIGS. 20 and 21 are respectively a perspective and a longitudinal cross section of the humidifier tub lid of FIG. 14.

With reference to FIG. 21, the inside wall of the tub lid 700 has projections 802a, 802b which serve to limit the press fitting of the tub lid onto the tub base 698. One projection 802a is provided at the front of the tub, and further projections 802b, or sets of projections, are provided on opposed side walls of the tub lid, forward of the rear of the tub. This positioning of the projections 802b allows one-handed disengagement of the tub base and tub lid by squeezing together of the base and lid at their rear end, causing the connection to pivot about the side projections 802b and the tub and lid to separate at the front. The ability to separate these components one-handed is a feature of considerable utility, especially for stroke patients or other users with limited dexterity.

As best seen in FIGS. 20 and 21, the water container lid 700 has an air passage 718 formed as a U-shaped channel, leading to the humidified air entry aperture 720 into the headspace of the water container. The channel floor slopes down in the direction of air flow from the air inlet end to the end at which the air enters the water container. The water container lid also has an elliptical humidified air exit aperture 722. These air passages and apertures co-operate with the humidifier lid 648 when closed to define the air flow paths within the humidifier, as will be described below.

Water may be added to the water container via the air exit aperture 722 while the tub lid is in place, or by removing the tub lid.

The tank is intended to be filled via the air outlet 722, and the apparatus may be provided with a filling bottle with a spout dimensioned for a convenient fit with that outlet. Such a bottle may be provided with a spout of the kind incorporating an air bleed passage which will allow the tank to fill to the correct predetermined height.

In alternative embodiments, other filling arrangements may be employed, for example by removing the tub lid. The correct filling height may also indicated by filling level graduations scribed or otherwise marked on the wall of the water tub.

A micro switch (not shown) or other sensing means may be provided to turn off power to the heater pad when the lid is opened, and/or when the water container is removed.

Humidifier Lid and Air Flow Paths

Figure 17:
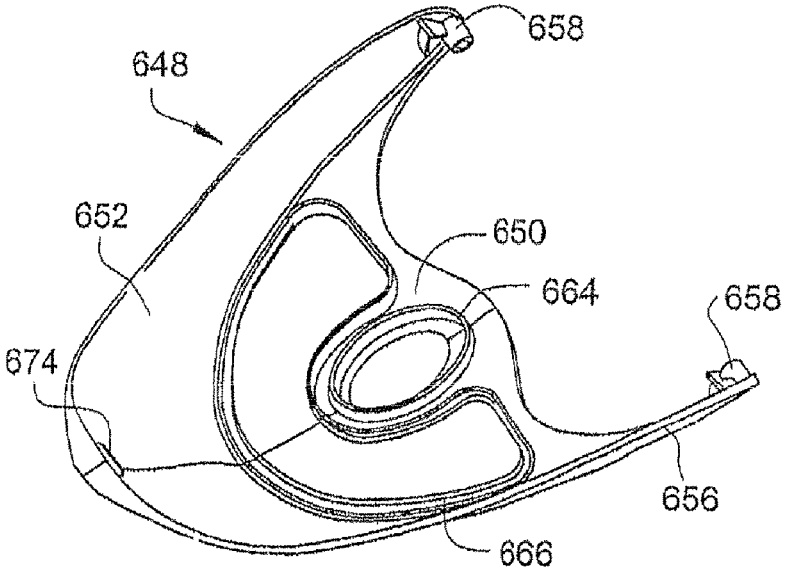
FIG. 17 is an underside perspective of the humidifier lid of FIG. 14.
Figure 18:
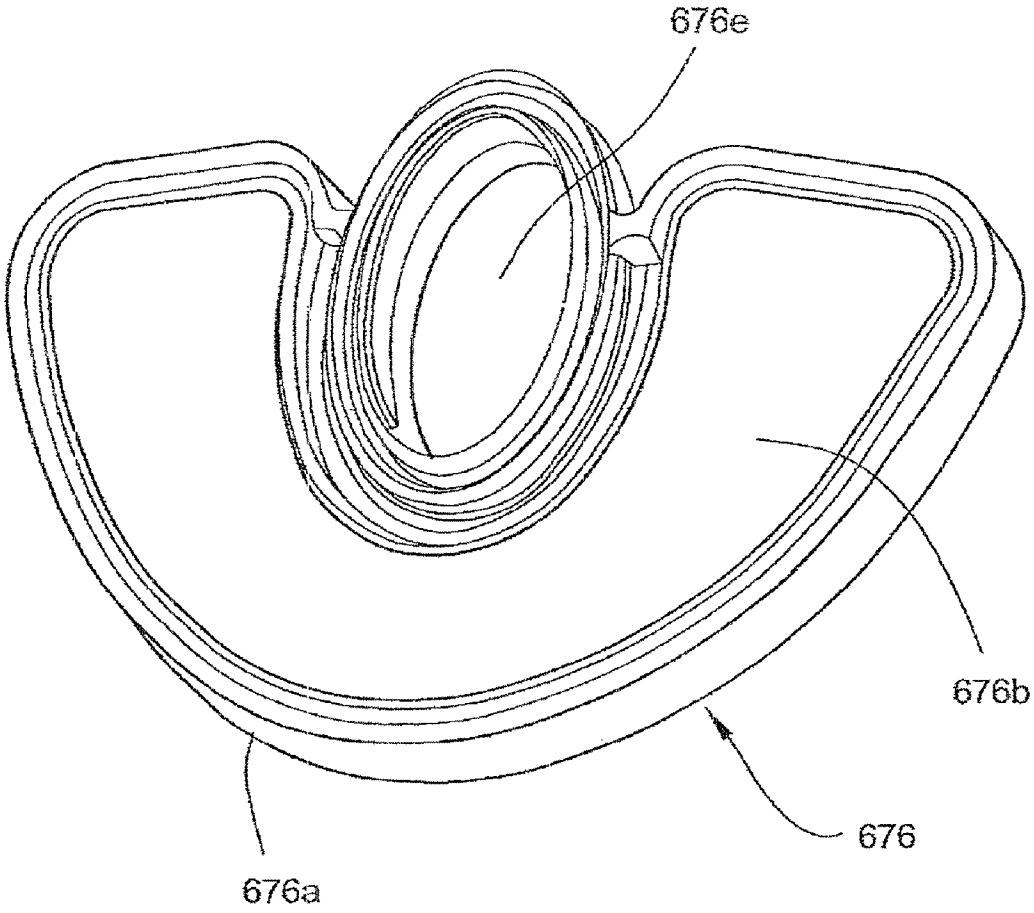
FIGS. 18 and 19 are respectively a perspective and a detail cross section of the humidifier lid seal of FIG. 14.
Figure 19:
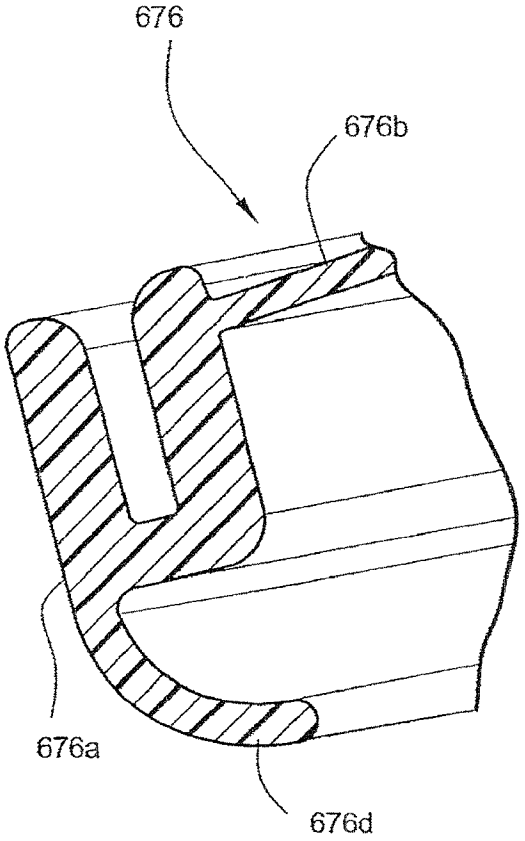

FIGS. 17 to 19 show the underside of the humidifier lid 648 and the seal 676 which provides a seal to the tub lid 700 about the U-shaped passage 718 and the humidified air exit aperture 716. The seal 676 comprises an edge seal portion 676a and membrane portion 676b, as shown in FIGS. 18 and 19.

The lid 648 has an upper wall 650 and a front wall 652 which extends downwards, and outwardly, from the upper wall. The upper wall 650 has a recess at its rear side, such that the part of the upper wall and front wall 652 on each side of the recess constitutes a rearwardly projecting arm 656. At the rearmost extremity of each arm 656 there is an inwardly projecting hub 658. The hubs 658 are configured to be received in the sockets 622 of the humidifier front cover 602 such that each hub and its corresponding socket constitute a hinge connection, for attaching the lid 648 to the front cover.

During opening of the lid 648, it may be freely rotated about the hubs through greater than 90° until it reaches a maximum extent of normal travel. The lid and front cover are configured such that, if the lid is then rotated further, the hubs pop out of the sockets 622. This may be achieved, as would be understood by a person skilled in the art, by providing suitable chamfers on the hubs and/or sockets, or other suitable formations on the lid or cover, so that the lid flexes to release the hubs from the sockets.

The lower edge of each arm 656 is shaped complementarily to the shape of the upper portion of the face of the front cover to accommodate that part of the arm when the lid 648 is in a closed position.

The lid 648 includes a humidified air outlet pipe 662 which passes through the upper wall 650 and extends upwards and forwards at an acute angle from the top of the upper wall, for attachment of a hose to supply humidified air to a patient. The pipe 662 continues below the lower surface of the upper wall 650 to define an elliptical rim 664.

Extending downwards from the lower surface of the upper wall 650 is a wall 666 which is configured to define a closed path and hence a U-shaped enclosed region 668 within the confines of the wall.

At the front extremity of the front wall 652, that is, adjacent the lower edge of that wall, there is provided a recessed notch 674 on the rear (inner) surface of that wall, for snap-fit engagement with the tab 646 of the heater pad cover to act as the catch for the lid. The lid may be opened by flexing the assembly to release the tab from the notch.

Attached to the lid 648 is an elastomer lid seal 676, which is illustrated in FIGS. 18 and 20. The edge seal portion 676a of the lid seal includes a channel 676c which fits over the wall 664 and rim 666 on the bottom of the lid 648, and a curved sealing flange 676d which seals against the top surface of the tub lid, so that the space between the U-channel 718 on the tub lid and the seal membrane forms an inlet air passage of the tub, and the air outlet aperture 722 of the tub lid communicates via the elliptical opening 676e in the lid seal to the air outlet pipe 662 of the humidifier lid 648. This is achieved without the need to connect and disconnect air tubes to remove the water container.

As the air supplied from the flow generator is under pressure, this pressure assists the sealing flange 676d of the sealing member 676 to create a firm seal around the recess 718 by forcing the extension portion outwards and downwards. A similar effect is created on the seal surrounding the elliptical aperture 716 in the tub lid due to the pressure of the air exiting the water receptacle.

Once the air from the flow generator passes into the water container, the air then travels across the surface of the water so that the air becomes humidified. The heating of the water by the heating pad enhances this humidification. The air then exits the water container through the outlet opening 716 to the air outlet pipe 662, which is in turn attached to a suitable hose (not shown) for supplying the humidified air to a patient.

By providing the air inlet to the water tub headspace via an arcuate path, the air mass within the container is caused to swirl and thus enhance the uptake of water vapour from the water contained in the tub.

The enhanced uptake of water vapour achieved by inducing the swirling of air as it passes through the tank enables, in an alternative embodiment of the invention, the elimination of the heating of the water in the tub. In such an embodiment the heating element and its controls, and the heat transfer components including the heating plate and the metal tank base are eliminated, and the humidifier becomes a simpler, passive, device.

A humidifier assembly in accordance with the present invention has a number of advantages over the prior art. One advantage relates to convenience of use. Convenience of use is important for all patients, especially those who have poor dexterity.

The base of the humidifier assembly includes a generally "negative" U-shaped channel. The bottom portion of the water tub has a corresponding "positive" U-shape. The outer wall of the U-shape is sloping, whereas the inner wall is generally vertical. Because the base and water tubs have complementary configurations, placing the water tub generally in the correct position means that it will to some extent self-align into the correct position, which as described below, is a sealing position.

A water tub according to the present design can be easily placed in a sealing position without requiring a patient to connect small fiddly tubes such as used in the prior art. An aspect of this is that a seal is provided by placing a generally flat surface such as the rear of the water tub, or the top surface of the water tub, against respective silicone gaskets that present a corresponding flat surface. The respective seals are formed when the two flat surfaces contact. Thus the humidifier assembly has a very convenient "drop-in" configuration.

The water tub is held in position by the simple motion of swinging the pivoting lid through approximately 90° from fully open to closed. The lid is locked in position via a robust mechanism which provides and audible and reassuring "click"-sound when engaged. Whilst in the preferred embodiment, a pivoting movement is used for the lid, other movements are contemplated including sliding and translation.

The lid of the humidifier assembly includes an air delivery tube connector, which in a preferred form is generally cylindrical. Connection of the air delivery tube to the lid can be achieved regardless of whether the water tub is in position. This arrangement means that the water tub can be removed and refilled with water if necessary without requiring disengagement of the air delivery tube from the humidifier assembly.

The illustrated humidifier construction provides a compact humidifier adapted for ease of manufacture and use, and further provides protection against backflow of water into the flow generator when the humidifier and flow generator units are assembled together. Backflow protection is provided by the sloping floor of the air passage and the location of the air inlet aperture 801 and the aperture 722d in the seal 722 relative to the air inlet 720 from the air passage 718 into the headspace of the humidifier tub 698. In particular, if the tub is overfilled while in its horizontal position, the water will flow back along the U-shaped passage 718 only as far as its forwardmost portion, which has a front wall 717 lower than the air inlet aperture 801, and will drain towards the front of the machine. If the machine is tipped up onto its rear, the water will be prevented from flowing back along the air passage from the tub to the air inlet 801 as the intermediate portion of the air passage 718 will be above the level of the aperture 720. The water will then flow back into the tub once the machine is righted.

If the machine is tipped onto its side, either the air inlet aperture 720 or the air inlet 801 will be above the water level and thus water should not flow back into the low generator. Again, any water which escapes the tub will flow back into the tub once the machine is righted.

If desired, further security against backflow can be provided by locating a non-return valve at an appropriate point, for example a flexible membrane supported in the mouth of the humidifier air inlet.

In addition to those features and advantages already described, the components and features of the humidifier according to the present embodiment have various advantages.

By providing the top seal to the water receptacle as part of the humidifier lid, improved simplicity of use is achieved while minimising the risk of spillage of water. In addition, the contour of the lid seal is adapted to collect condensation which may form in the lid cavity and the headspace of the water receptacle, preventing backflow of this condensation to the flow generator when the lid is opened.

Furthermore, the configuration of the front and back covers of the humidifier and of the heater pad is adapted to allow fitting together in a vertical orientation, to minimise the need for reorientation during assembly of the humidifier unit on the production line.

In addition, the resilience of the connection between the lid and the water receptacle, provided by the lid seal, is adapted to maintain downwards pressure on the water receptacle when the lid is closed, to maintain good heat-transfer contact between the base of the water receptacle and the heater pad without the added complexity and expense of spring-loaded mounting of the heater pad.

Humidifier Power Supply

The humidifier is provided with a control knob allowing adjustment of the humidity of the air supply to the patient. With increasing humidity setting, the temperature of the water container is increased by providing increased power to the heater, to raise the humidity of the air leaving the humidifier. The control knob may have a smoothly variable control, or a series of discrete humidity settings, and will have an 'off' setting where no power is supplied to the heating pad. The correlation between the humidity setting and the power to the heater is controlled by a circuit on the PCB 804.

Figure 22:
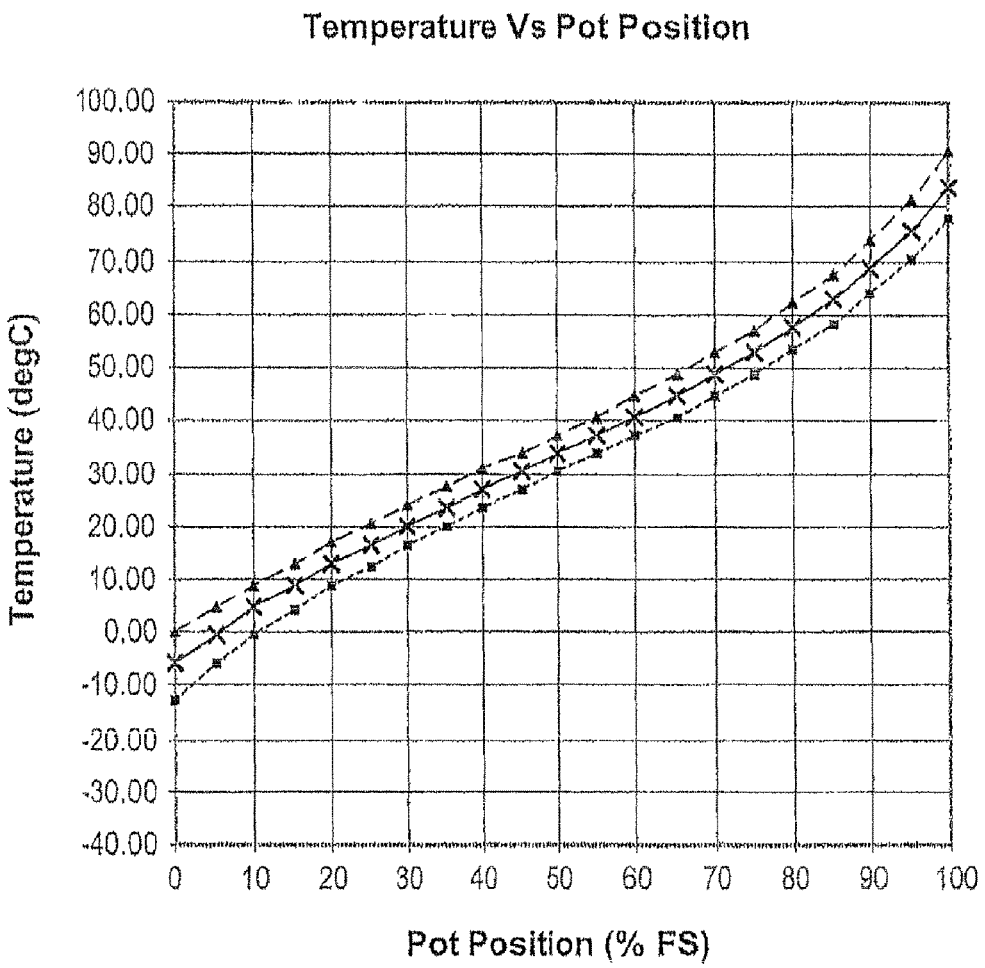
FIG. 22 is a graph of heater target temperature against humidifier setting.

FIG. 22 is a sketch of a preferred calibration curve of target water container temperature (y axis) against humidity setting (x axis), including upper and lower tolerances.

At the left hand end of the correlation curve, corresponding to the low humidity settings and the off position of the control knob, the heater control selects a very low target heater temperature—less than ambient temperature, and preferably lower than the lowest operating temperature of the humidifier. In this way, the heating is turned off when the control knob is in its off position, while allowing use of a less expensive potentiometer without an integral off switch or a separate on/off switch. The mounting of the control knob mechanism may provide a tactile 'click' at the off position of the control knob, to confirm to the user that the heater is turned off.

Figure 23:
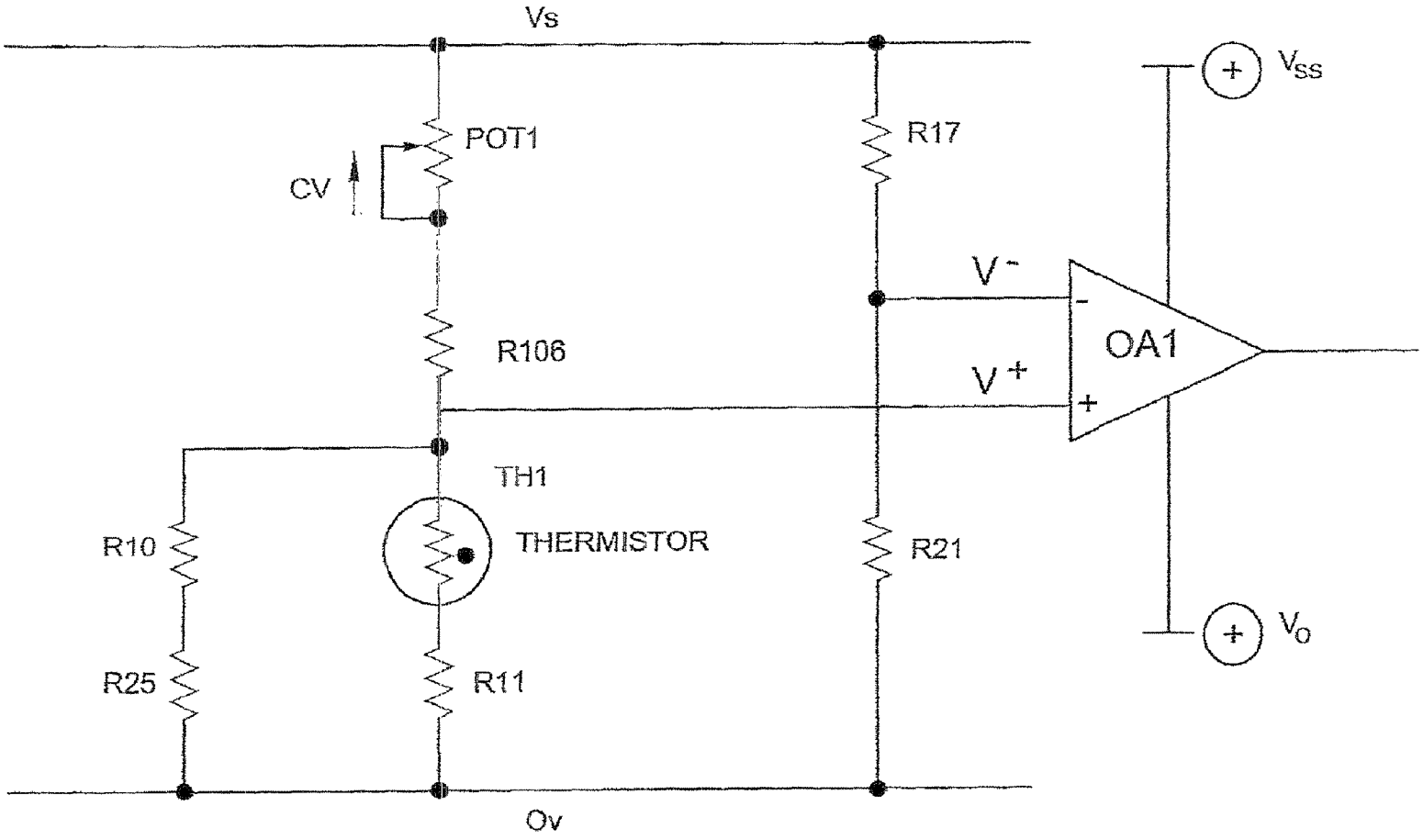
FIG. 23 is a schematic circuit diagram of a power control circuit to the humidifier heater.

FIG. 23 is a circuit diagram of the humidifier control circuit for controlling the water temperature, including a potentiometer POT1 actuated by the control knob 805 and an operational amplifier OA1 providing power to the heater 800.

A potentiometer may be used in series with the heating element to set the operating temperature. However, this may result in large heat losses through the potentiometer as in the following equation $$P=V^2/R$$

where V=the supply voltage and is normally fixed and R=RH+RP where RH is the resistance of the heater and is fixed and RP is the resistance of the potentiometer which is variable and provides the temperature control. The current is: I=V/R, and the proportion of heat through the potentiometer is $I^2*RP=RP*V^2/(RP+RH)^2$. The remainder of the heat is used by the heater element to heat the water.

These heat losses in the potentiometer require large heat dissipation surfaces to prevent overheating.

In the present embodiment, the potentiometer is used in the control path of a semiconductor arrangement to set the operating temperature. This substantially reduces the current through the potentiometer because the potentiometer now only carries a semiconductor control current rather than the load current required to drive the heater element.

In a preferred embodiment, the potentiometer is used in conjunction with a temperature sensing element to control an operational amplifier which drives the heater directly or through a high current semiconductor switch.

FIG. 23 shows an arrangement for controlling temperature via an operational amplifier OA1.

The operational amplifier n1 has a pair of inputs, V+ being an adding input and V− being a subtracting input. The output of the amplifier is proportional to the difference between the voltages on the inputs V+ and V−.

Input V− is connected to a reference voltage determined by the ratio of resistors R21 and R17;

$$Vref=Vs*R12/(R12+R17)$$

The temperature of the water is sensed by temperature sensitive resistive element, thermistor TH1, and the operating point is set by potentiometer POT1. The operational amplifier input V+ is connected to the junction of R106 and thermistor TH1. The operational amplifier switching threshold is determined by the ratio of the resistance of the potentiometer POT1 plus resistor R106 to the resistance of the resistance network formed by thermistor TH1 plus resistor R11 in parallel with resistor R10 plus resistor R10 equals the ratio of resistor R17 to resistor R21. That is, the operational amplifier switches when the junction between the thermistor TH1 and resistor R106 crosses over the potential at V−.

The operational amplifier is powered from supply points Vss and Vo, so the drive current does not pass through the potentiometer. Vss may be the same as Vs, and Vo may be the same as 0 v. The operational amplifier may drive the heater element directly or it may control a power transistor which drives the heater element, This arrangement significantly reduces the dissipation through the potentiometer, allowing a smaller potentiometer, with smaller cooling needs, to be used. The arrangement is also well adapted for use in implementing the 'soft' off setting arrangement described above with reference to FIG. 22.

Reminder Menu

Figure 24:
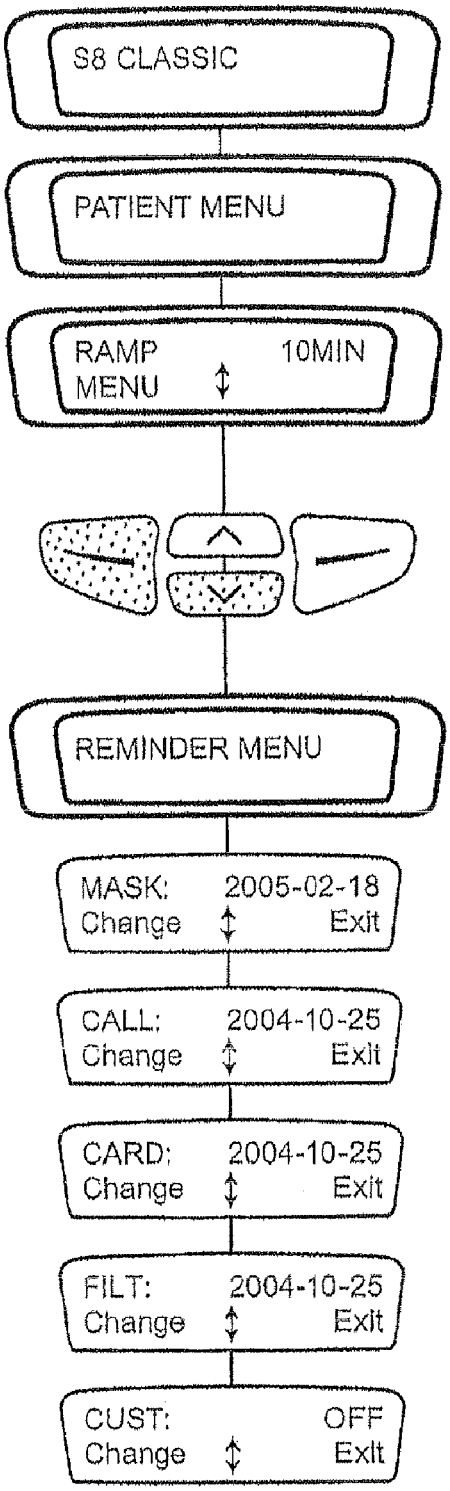
FIG. 24 illustrates reminder menus of the flaw generator control.

FIG. 24 is a flowchart of a Reminder menu to set a number of reminders to alert the patient to specific events; for example, when to replace their mask, when to insert a Data Card (if their device is Data Card enabled) and so on. It can also be used to set special customised reminders.

When a reminder is due, a message is displayed on the LCD and remains whenever the device is not delivering therapy. The backlight on the LCD flashes when a message is displayed. If more than one reminder for a patient is scheduled for the same date, all scheduled reminders are displayed during that day. A patient can clear a message by pressing the LEFT key (or inserting a Data Card, in the case of the Data Card reminder).

The default setting for all reminders is that they are disabled. To use the reminder menu, the patient enters the Reminder Menu from the standby screen by pressing LEFT and DOWN for at least three seconds.

FIG. 24 summarises the Reminder Menu screens:

REPLACE MASK—to set a timed reminder to remind a patient when they need to replace their mask. The patient can press the LEFT (clear) key to remove the message from the LCD.

CALL PROVIDER—to set a reminder for the patient to phone the therapist at a certain time; for example, to discuss how their therapy is going. The patient can press the LEFT (clear) key to remove the message from the LCD.

INSERT CARD—if a patient's flow generator is Data Card enabled, the therapist can set a timed reminder on the flow generator to remind them that they need to insert a Data Card to transfer patient data. This enables the therapist to establish compliance. The patient should actually insert the Data Card in order to clear the message from the LCD. (They can also press the LEFT (clear) key to remove the message.)

REPLACE FILTER—to set a timed reminder to remind the patient when to replace the air filter. The patient can press the LEFT (clear) key to remove the message from the LCD.

FIGS. 25 to 32 are rear views of the flow generator, showing various forms of modular data connections foreshadowed earlier, utilising the slot 83 in the rear of the flow generator housing.

Figure 25:
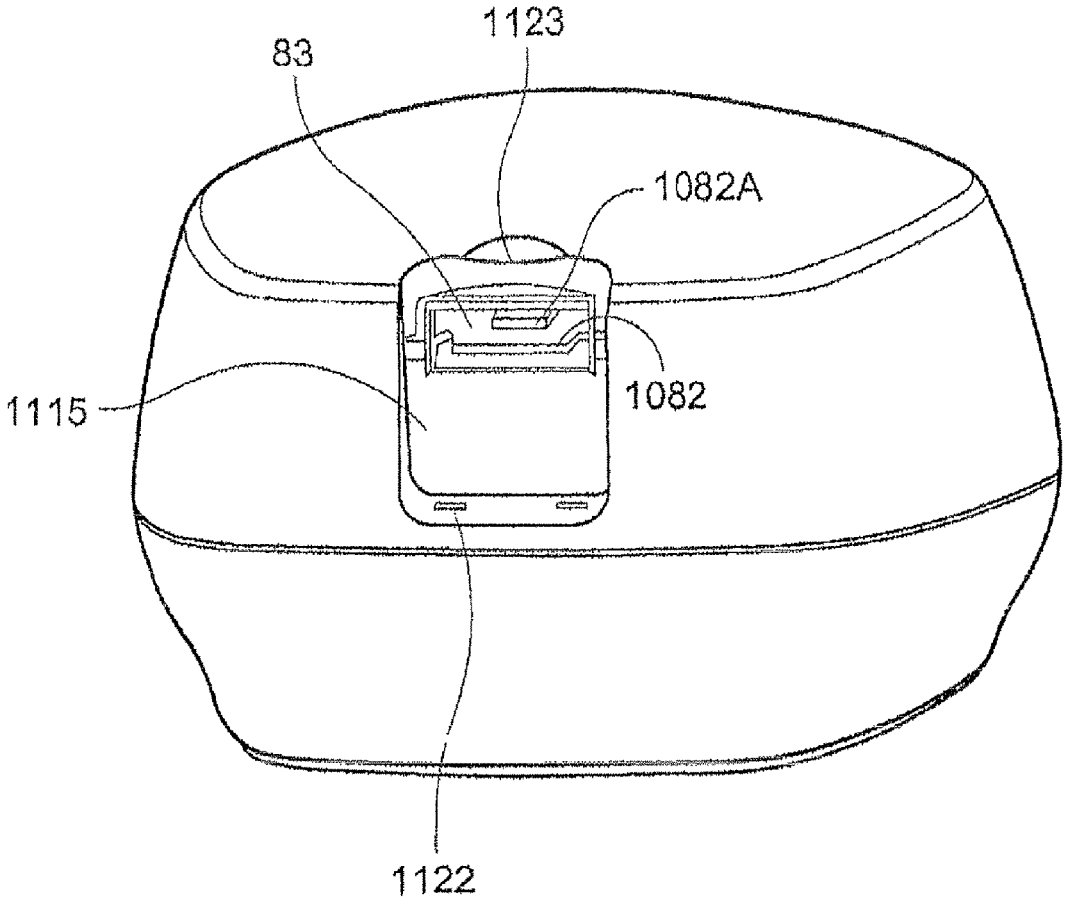
FIGS. 25 to 34 show various modular data connector arrangements.
Figure 27:
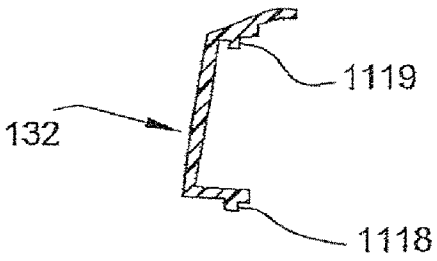

With reference to FIG. 25, the slot 83 is provided in the wall of a rectangular recess 1115. An arcuate depression 1123 is provided in the upper surface of the unit above the recess 1115 to facilitate removal of closure elements from the depression, as described below.

At the rear of the printed circuit board 81, an edge connector 1082 and a sliding connector 1082A are aligned with and accessible through the connector slot 83 in the rear of the case 60, providing for the modular connector arrangements to be described in more detail below.

Figure 26:
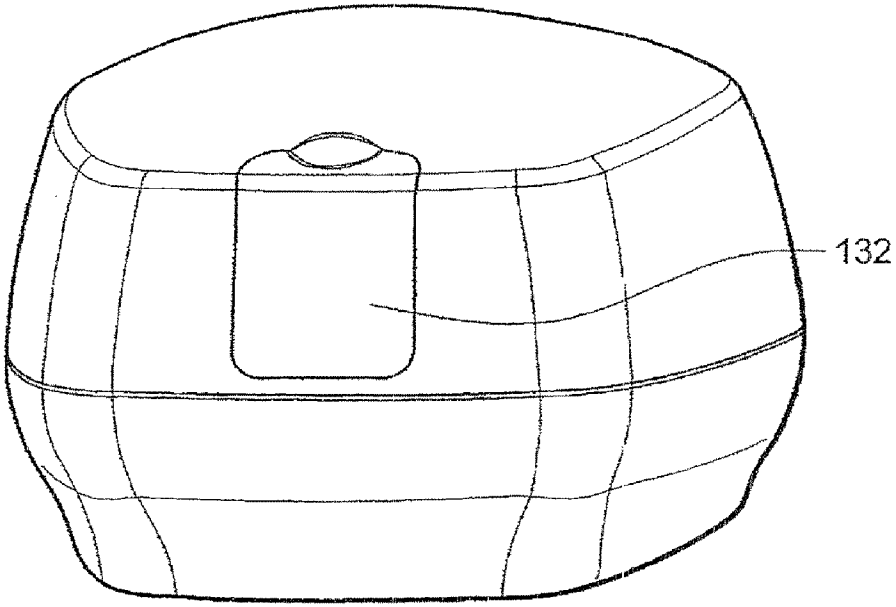

Where, as shown in FIG. 26, the flow generator in question is not intended to be employed with any data connection, the slot 83 is closed off by a blank closure element 132, shaped to fit into the recess 1115. The closure element is shown in more detail in FIG. 27. This element snaps into the recess by means of lower tabs 1118 and an upper tab 1119 which fit corresponding depressions such as 1122 in the walls of the recess 1115, to close the slot 83 and conform to the contours of the surrounding surface of the unit.

Figure 28:
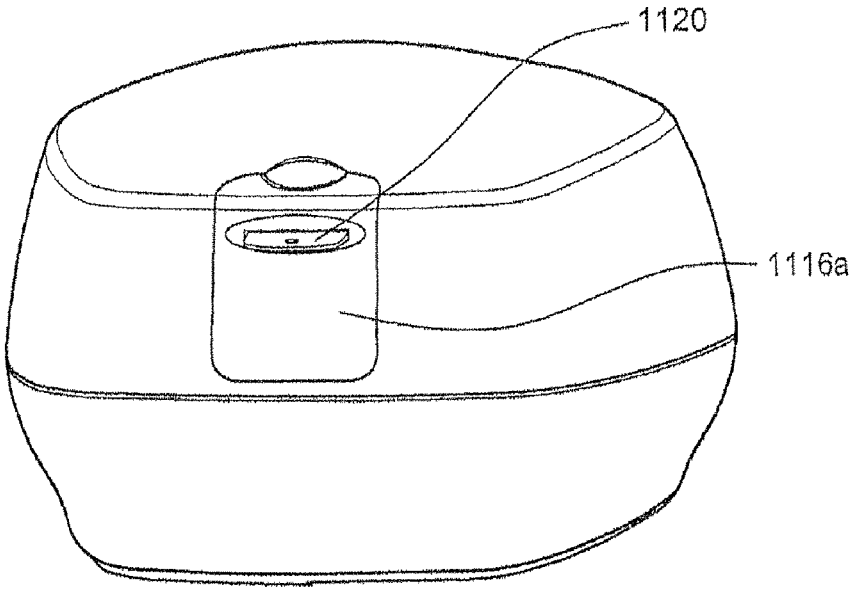

Complementarily shaped closure elements can be provided for the reception of different kinds of data devices. Shown in FIG. 28 is an element 1116a provided with a slot for the reception of a smart card 1120. The element 1116a or the printed circuit board itself may carry the necessary smart card socket.

Figure 29:
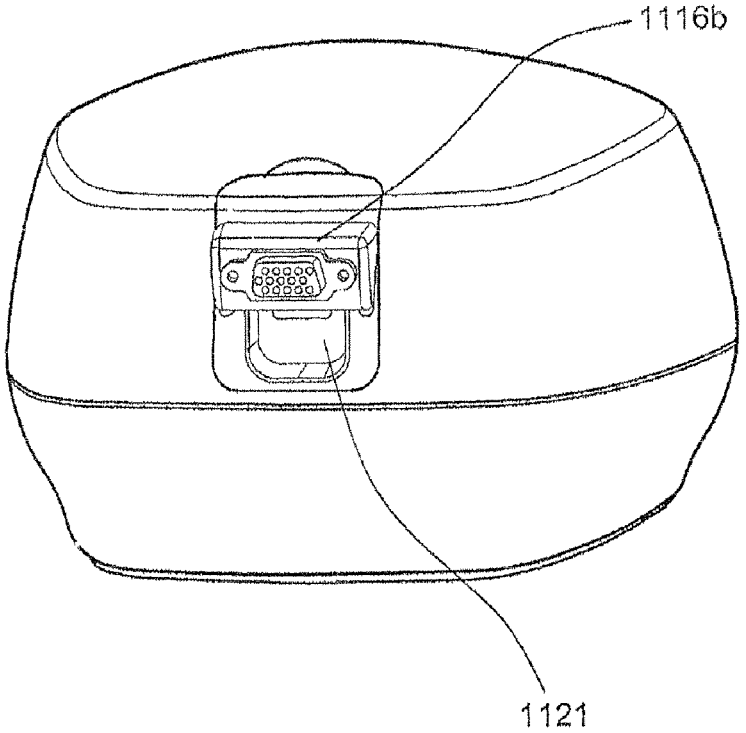
Figure 29A:
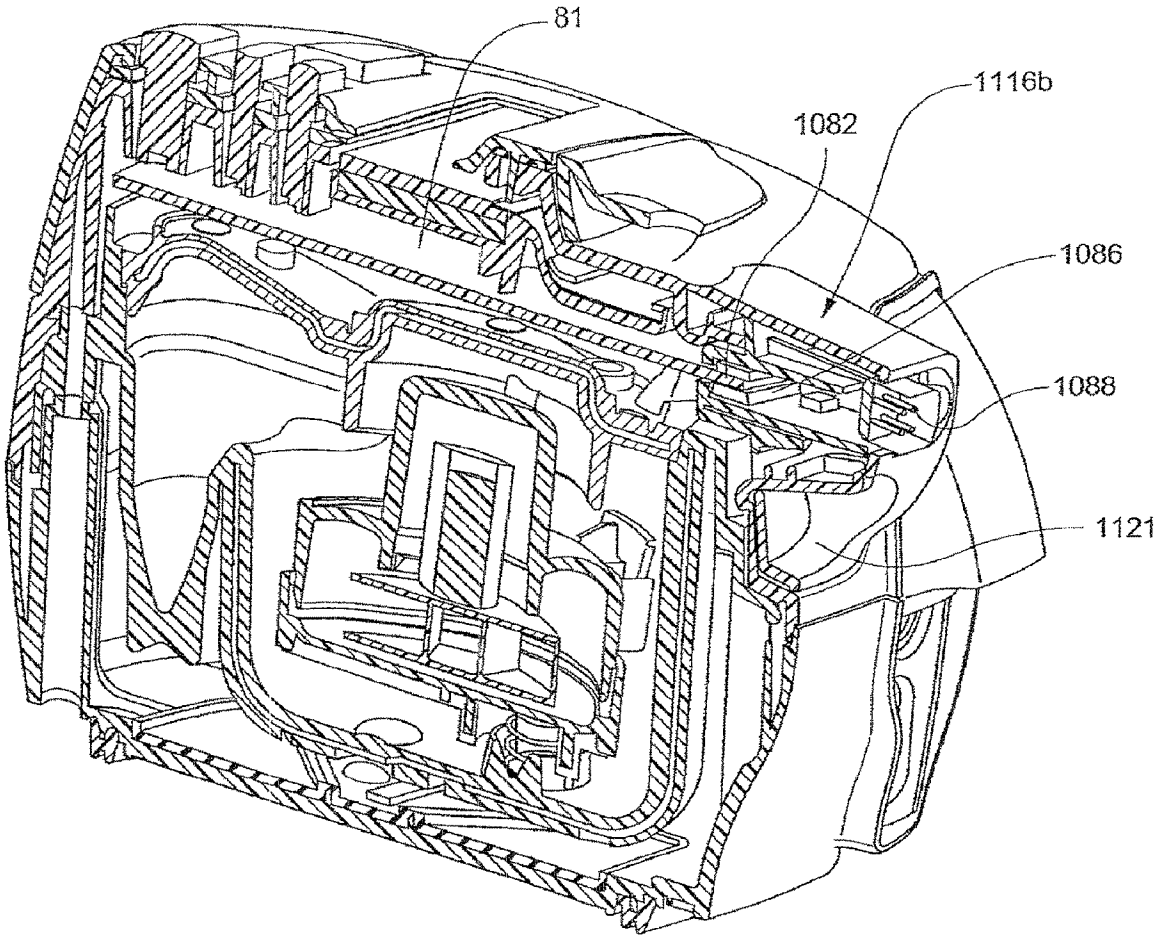

Shown in FIG. 29 is a closure element 1116b provided with a DB type data socket. In this case the element 1116b is contoured to provide a lower front recess 1121 to facilitate gripping of the associated plug. A cross-section of a modified form of this arrangement is shown in FIG. 29A, illustrating the connection between the internal connector 1086 of the element 1116b and the edge connector 1082 of the PCB, and the external DB9 connector 1088.

Other forms of element 1116 can be provided to enable the connection of devices such as memory cards and preprogrammed devices as required. This facility furthermore enables a wide range of devices to be integrated with the apparatus in modular fashion, for example a clock display which may utilise the system clock contained in the flow generator controller, a voice activation unit, oximetry, ECG and other diagnostic aids, a sound recorder, a light.

Figure 30:
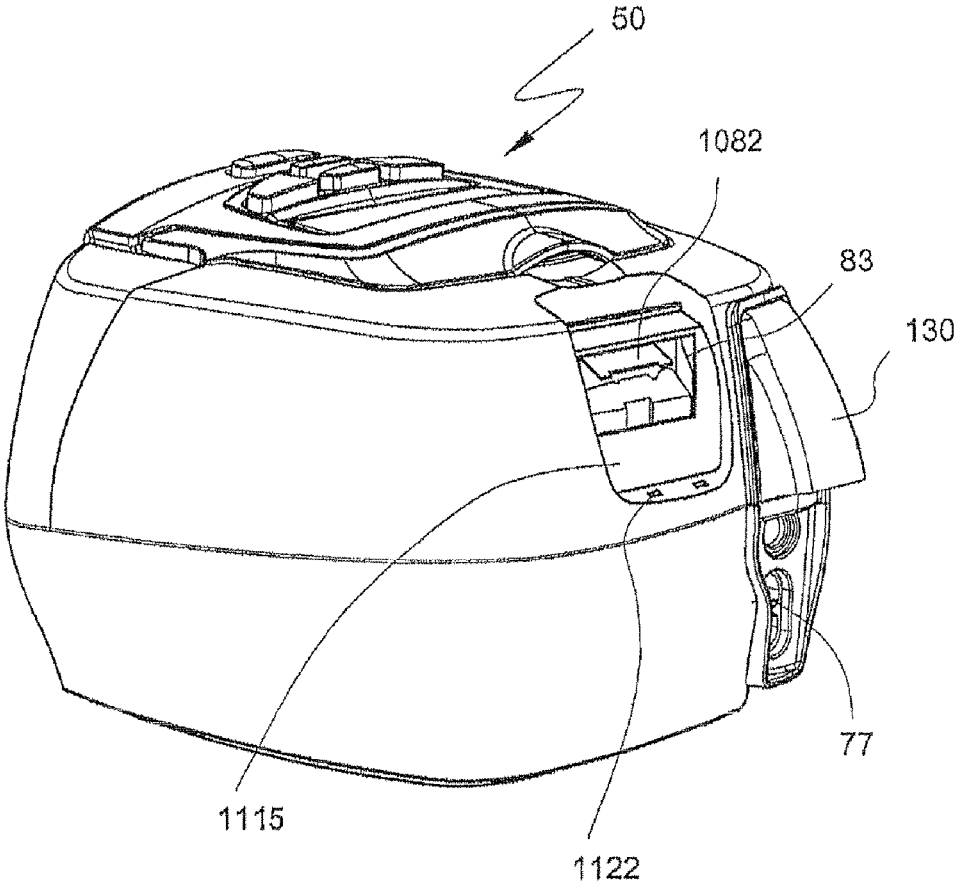
Figure 31:
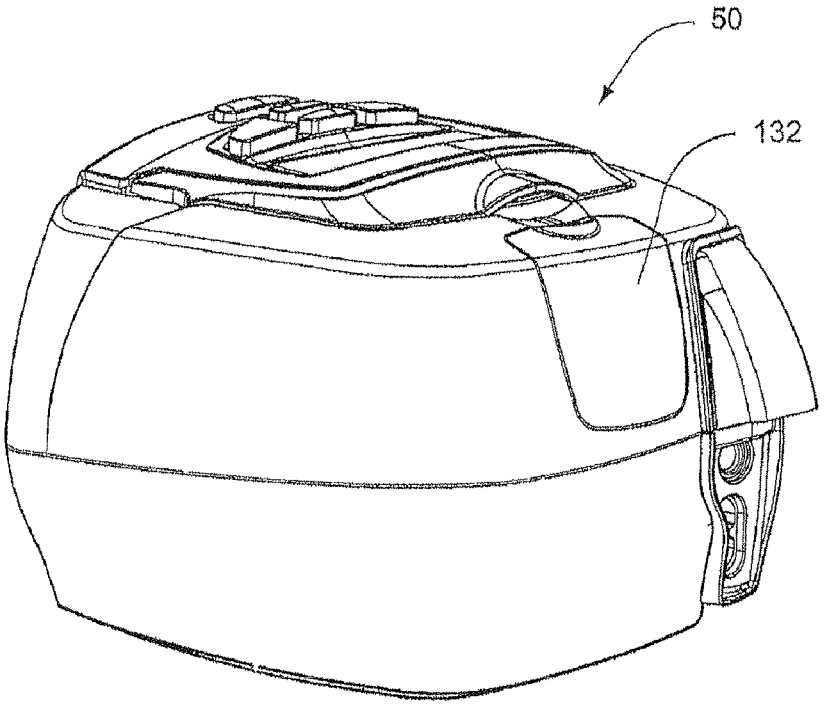
Figure 32:
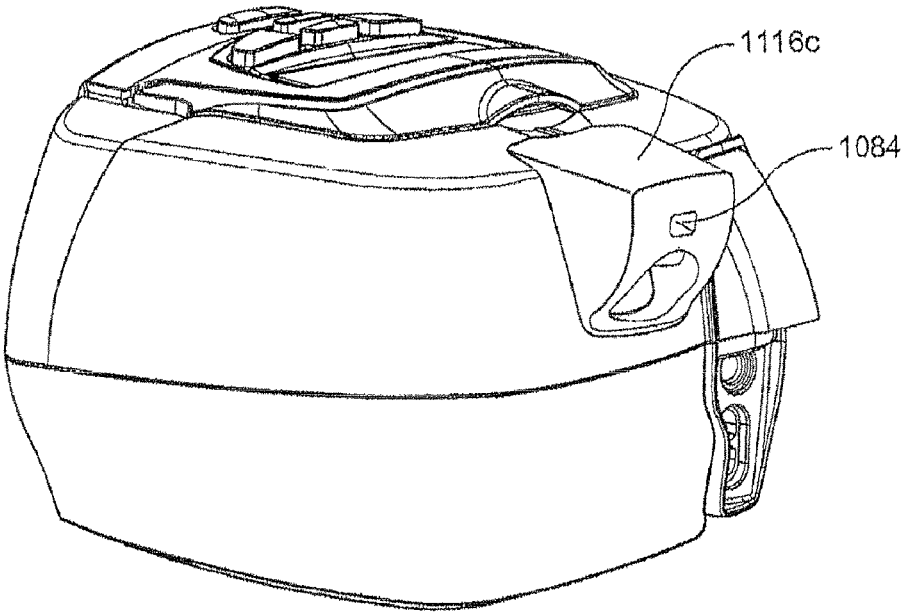
Figure 33:
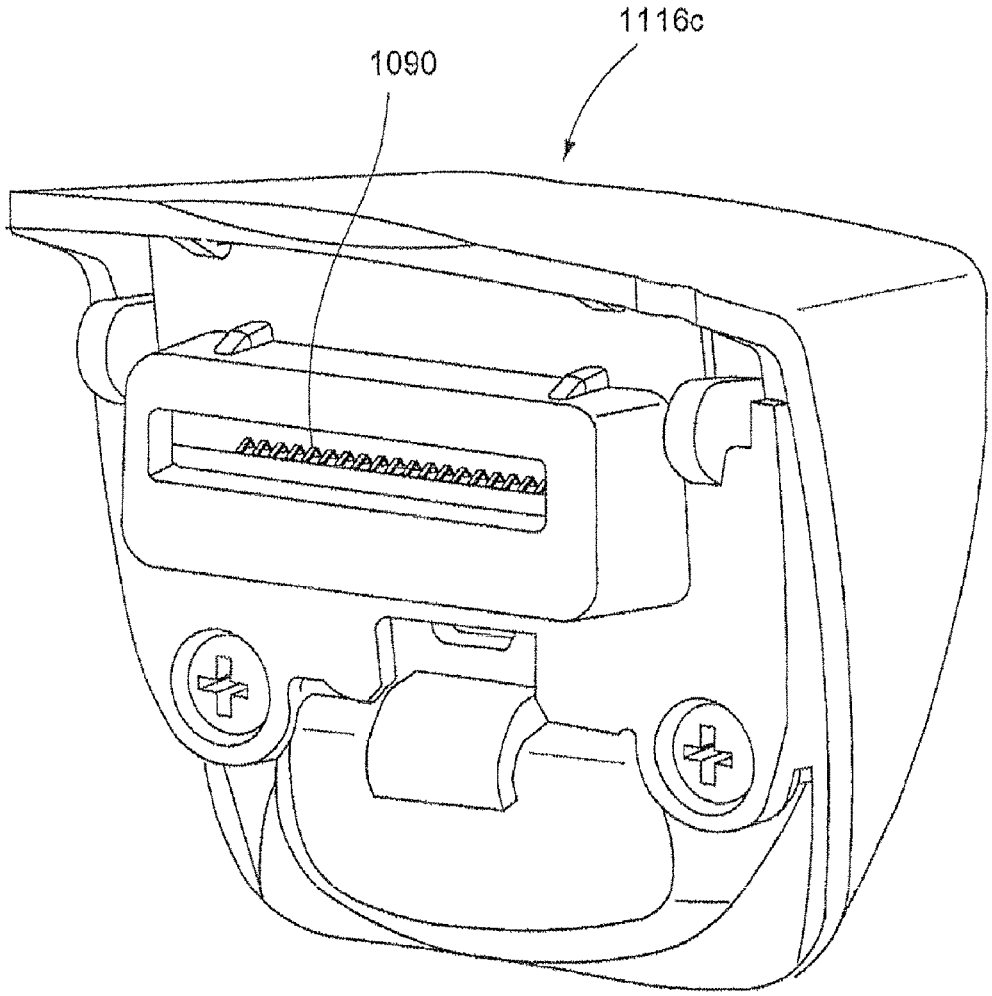
Figure 34:
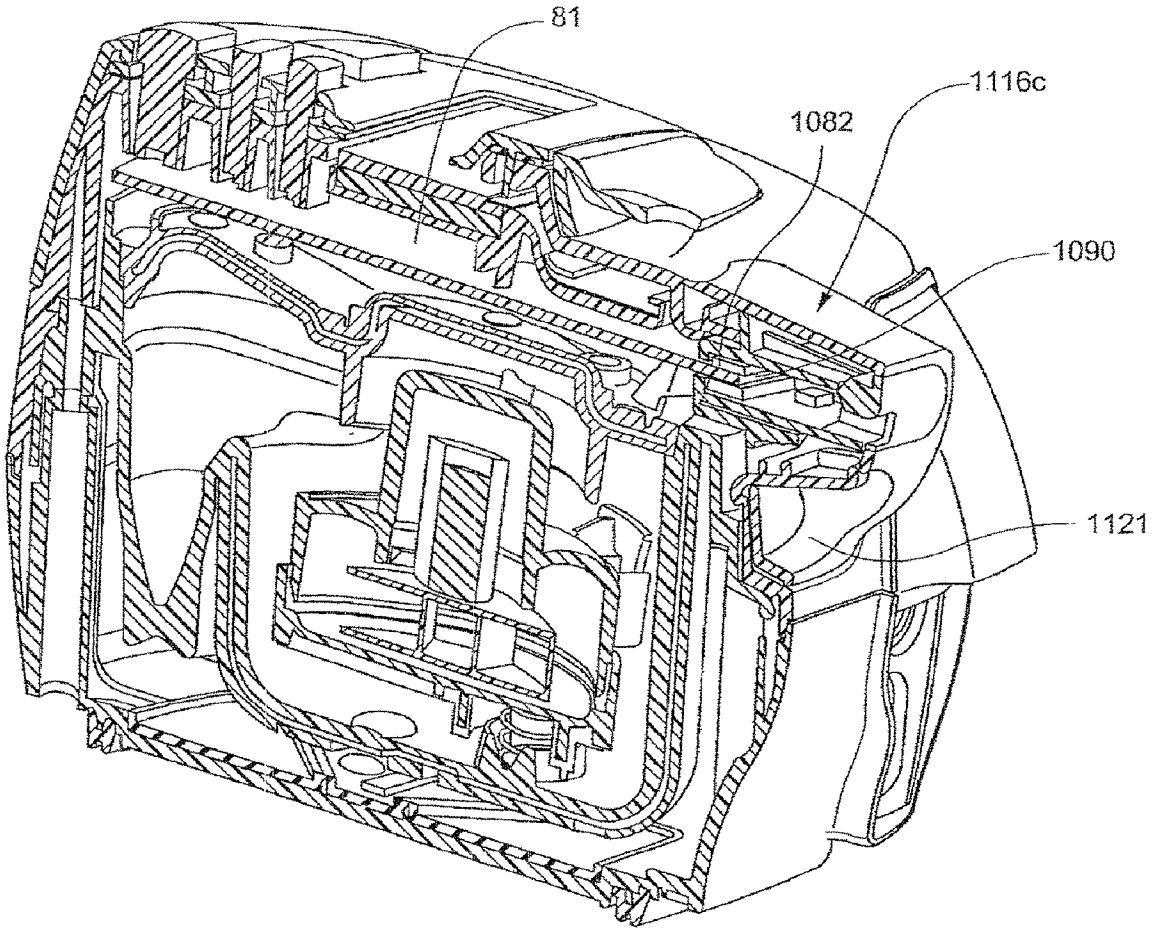

FIGS. 30 to 32 are a series, of rear perspective views of the flow generator, illustrating one embodiment of the modular data connector arrangement. FIG. 33 shows the front, inner surface of the USB closure element module, and FIG. 34 is a vertical cross-section of the flow generator.

FIG. 30 shows the slot 83 open, exposing the edge connector 1082 and sliding connector (not visible in this view) at the rear of the flow generator PCB 81. The connectors 1082, 1082A comprise a plurality of electrical contacts for carrying data and/or power between the PCB and an external device.

FIG. 31 shows the arrangement of FIG. 31 where no data connection is required, with the slot covered by a blank closure element 132 generally as described above with reference to FIGS. 25 to 27.

FIG. 32 shows a removable closure element module 1116c carrying a standard universal serial bus (USB) port 1084 on its rear surface. The element 1116c incorporates an electrical/data pathway to an electrical connector 1090 at its forward, inner surface (FIGS. 33 and 34) adapted to connect with all or selected ones of the contacts of the PCB connector 1082 for electrical and/or data transmission. The closure module 1116c has internal electrical components completing a data and/or electrical pathway between its internal and external connectors so that the module acts as an adaptor between die PCB connector and a standard USB port.

By providing the modular data connection arrangements as described above, in which a plurality of interchangeable connection modules fit to one or more fixed, standard connectors on the PCB, the cost and size of the flow generator unit may be reduced as the unit may be provided with only those connectors which are needed by that patient, and additional connector modules supplied only if the need arises. Furthermore, the arrangement facilitates upgrade of the data connection arrangement of the flow generator to keep up with technological advances or changes in global data connection standards.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise, comprised and comprises where they appear.

While particular embodiments of this invention have been described, it will be evident to those skilled in the art that the present invention may be embodied in other specific forms without departing from the essential characteristics thereof. The present embodiments and examples are therefore to be considered in all respects as illustrative and not restrictive, the scope of the invention being indicated by the appended claims rather than the foregoing description, and all changes which come within the meaning and range of equivalency of the claims are therefore intended to be embraced therein. It will further be understood that any reference herein to known prior art does not, unless the contrary indication appears, constitute an admission that such prior art is commonly known by those skilled in the art to which the invention relates.

The invention claimed is:

1. An apparatus for treatment of obstructive sleep apnea, comprising:

a continuous positive airway pressure device capable of providing a supply of air at a pressure in [the] *a* range of about 4 cmH2O to about 20 cmH2O; and a humidifier connectable to the continuous positive airway pressure device, the humidifier including:

a humidifier base, a humidifier lid hingedly connected to the humidifier base to allow the humidifier lid to close and open, the humidifier lid including an air delivery pipe constructed and arranged to mate with an air delivery tube, the humidifier lid further including a lid seal, the humidifier base further including a humidifier heater plate and a humidifier base seal; and a water tank having a *water* tank base to receive water and a *water* tank lid, the *water* tank base including a heat conductive portion to conduct heat from the humidifier heater plate to water in the *water* tank in use, the apparatus further comprising a latch to releasably connect the continuous positive airway pressure device to the humidifier; and a locking mechanism constructed and arranged to releasably hold the humidifier lid when closed, wherein the humidifier base is constructed and arranged to receive the water tank when the humidifier lid is open;

wherein, when the humidifier base receives the water tank, the heat conductive portion of the water tank is positioned relative to the humidifier heater plate to allow heat transfer communication therebetween in use;

wherein, when the continuous positive airway pressure device and the humidifier are latched together and the humidifier lid is closed with the water tank placed in the humidifier base, a sealed gas flow path is established, said sealed gas flow path extending from the continuous positive airway pressure device, through the humidifier base seal located between the humidifier base and a rear surface of the water tank, through an interior of the water tank, through the lid seal surrounding an outlet of the *water* tank lid and located on an underside of the humidifier lid, and to the air delivery pipe of the humidifier lid; and wherein an engagement face of the continuous positive airway pressure device includes electrical connectors to deliver power to the humidifier heater plate.

2. The apparatus of claim 1, further comprising a backflow prevention structure located adjacent a mouth of [the] *an* inlet aperture *of the water tank.*

3. The apparatus of claim 2, wherein the backflow prevention structure, comprises a non-return valve.

4. The apparatus of [any of the] claim 1, wherein the humidifier includes a pair of flat male blade connectors for engagement with mating connectors on the continuous positive airway pressure device.

5. The apparatus of claim 1, wherein the continuous positive airway pressure device is constructed and arranged to detect automatically the presence of the humidifier and adjust an automatic control algorithm of the continuous positive airway pressure device when the continuous positive airway pressure device and the humidifier are connected.

6. The apparatus of claim 1, [further] wherein the water tank includes filling level graduations [scribed or otherwise] marked on [the] *a* wall of the water tank.

7. The apparatus of claim 1, wherein the humidifier base and the water tank have complementary configurations to guide positioning of the water tank in the humidifier base.

8. The apparatus of claim 1 wherein the water tank further comprises a water tank seal.

9. The apparatus of claim 1 wherein the water tank is constructed and arranged to allow disengagement of the water tank base and the water tank lid.

10. The apparatus of claim 1 further comprising an air delivery conduit and a patient interface, and wherein the air delivery conduit is connected to the air delivery pipe of the humidifier lid, and the air delivery conduit is connected to the patient interface for delivery of humidified air to a patient.

11. The apparatus of claim 1, wherein the humidifier lid is constructed and arranged so that it is rotatable from a closed position to a maximum extent of normal travel in an open position, and wherein, upon further rotation of the humidifier lid beyond the maximum extent, the humidifier lid becomes removed from the *humidifier* base.

12. The apparatus of claim 1, wherein the locking mechanism is configured to provide an audible "click" sound upon locking.

13. The apparatus of claim 1, wherein the lid seal is a pressure-assisted seal.

14. The apparatus of claim 1, wherein the humidifier base seal is a pressure-assisted seal.

15. The apparatus of claim 1, wherein the humidifier base seal includes a connector portion and a peripheral seal to abut and seal against a flat surface radially surrounding an aperture of an inlet of the water tank.

16. The apparatus of claim 1, wherein the lid seal includes a sealing flange to abut and sealingly engage a surface radially surrounding an aperture of the outlet of the water tank lid.

17. The apparatus of claim 1, further comprising a user operable control for selecting a desired air humidity setting.

18. The apparatus of claim 1, constructed and arranged so that when the water tank is received in the *water* tank base and the humidifier lid is closed, the *water* tank base and the *water* tank lid are pressed rearwards.

*19. The apparatus of claim 1 further comprising a user operable control for selecting a desired air humidity setting,*

*wherein the humidifier includes a pair of flat male blade connectors for engagement with mating connectors on the continuous positive airway pressure device,*

*wherein the continuous positive airway pressure device is constructed and arranged to detect automatically the presence of the humidifier and adjust an automatic control algorithm of the continuous positive airway pressure device when the continuous positive airway pressure device and the humidifier are connected,*

*wherein the water tank includes filling level graduations marked on the wall of the water tank,*

*wherein the humidifier base and the water tank have complementary configurations to guide positioning of the water tank in the humidifier base,*

*wherein the water tank further comprises a water tank seal,*

*wherein the water tank is constructed and arranged to allow disengagement of the water tank base and the water tank lid,*

*wherein the humidifier lid is constructed and arranged so that it is rotatable from a closed position to a maximum extent of normal travel in an open position, and wherein, upon further rotation of the humidifier lid beyond the maximum extent, the humidifier lid becomes removed from the humidifier base,*

*wherein the locking mechanism is configured to provide an audible "click" sound upon locking,*

*wherein the lid seal is a pressure-assisted seal,*

*wherein the humidifier base seal is a pressure-assisted seal,*

*wherein the humidifier base seal includes a connector portion and a peripheral seal to abut and seal against a flat surface radially surrounding an aperture of an inlet of the water tank, and*

*wherein the lid seal includes a sealing flange to abut and sealingly engage a surface radially surrounding an aperture of the outlet of the water tank lid.*

*20. An apparatus for treatment of obstructive sleep apnea, comprising:*

*a continuous positive airway pressure device capable of providing a supply of air at a pressure in the range of about 4 cmH2O to about 20 cmH2O; and*

*a humidifier connectable to the continuous positive airway pressure device, the humidifier including:*

*a humidifier base,*

*a humidifier lid hingedly connected to the humidifier base to allow the humidifier lid to close and open, the humidifier lid including an air delivery pipe constructed and arranged to mate with an air delivery tube, the humidifier lid further including a lid seal with a sealing flange,*

*the humidifier lid being constructed and arranged to be a) rotatable from a closed position to a maximum extent of normal travel in an open position and b) removable from the humidifier base by further rotation of the humidifier lid beyond the maximum extent,*

*the humidifier base further including a humidifier heater plate and a humidifier base seal, the humidifier base seal including a connector portion and a peripheral seal; and*

*a water tank having a water tank base to receive water and a water tank lid, the water tank base including a heat conductive portion to conduct heat from the humidifier heater plate to water in the water tank in use, the water tank lid including an outlet with an aperture, the sealing flange of the lid seal being configured to abut and sealingly engage a surface radially surrounding the aperture of the outlet of the water tank lid, the peripheral seal of the humidifier base seal being configured to abut and seal against a flat surface radially surrounding an aperture of an inlet of the water tank,*

*the apparatus further comprising a latch to releasably connect the continuous positive airway pressure device to the humidifier; and a locking mechanism constructed and arranged to releasably hold the humidifier lid when closed, the locking mechanism being configured to provide an audible "click" sound upon locking,*

*wherein the humidifier base is constructed and arranged to receive the water tank when the humidifier lid is open;*

*wherein, when the humidifier base receives the water tank, the heat conductive portion of the water tank is positioned relative to the humidifier heater plate to allow heat transfer communication therebetween in use;*

*wherein, when the continuous positive airway pressure device and the humidifier are latched together and the humidifier lid is closed with the water tank placed in the humidifier base, a sealed gas flow path is established, said sealed gas flow path extending from the continuous positive airway pressure device, through the humidifier base seal located between the humidifier base and a rear surface of the water tank, through an interior of the water tank, through the lid seal surrounding an outlet of the water tank lid and located on an underside of the humidifier lid, and to the air delivery pipe of the humidifier lid; and*

*wherein an engagement face of the continuous positive airway pressure device includes electrical connectors to deliver power to the humidifier heater plate.*

*21. The apparatus of claim 20, wherein the lid seal and the humidifier base seal are pressure-assisted seals.*

*22. The apparatus of claim 20, wherein the water tank further comprises a water tank seal, the water tank is constructed and arranged to allow disengagement of the water tank base and the water tank lid and the water tank includes filling level graduations marked on a wall of the water tank.*

*23. The apparatus of claim 20, wherein the humidifier includes a pair of flat male blade connectors for engagement with mating connectors on the continuous positive airway pressure device.*

*24. The apparatus of claim 20, wherein the humidifier base and the water tank have complementary configurations to guide positioning of the water tank in the humidifier base.*

*25. The apparatus of claim 20, wherein the continuous positive airway pressure device is constructed and arranged to detect automatically the presence of the humidifier and adjust an automatic control algorithm of the continuous positive airway pressure device when the continuous positive airway pressure device and the humidifier are connected.*

*26. An apparatus for treatment of obstructive sleep apnea, comprising:*

*a continuous positive airway pressure device capable of providing a supply of air at a pressure in the range of about 4 cmH2O to about 20 cmH2O; and*

*a humidifier connectable to the continuous positive airway pressure device, the humidifier including:*

*a humidifier base,*

*a humidifier lid hingedly connected to the humidifier base to allow the humidifier lid to close and open, the humidifier lid including an air delivery pipe constructed and arranged to mate with an air delivery tube, the humidifier lid further including a lid seal,*

*the humidifier base further including a humidifier heater plate and a humidifier base seal; and*

*a water tank having a water tank base to receive water, a water tank seal, and a water tank lid, the water tank base including a heat conductive portion to conduct heat from the humidifier heater plate to water in the water tank in use, the water tank being constructed and arranged to allow disengagement of the water tank base and the water tank lid and including filling level graduations marked on a wall of the water tank,*

*the apparatus further comprising a latch to releasably connect the continuous positive airway pressure device*

*to the humidifier; and a locking mechanism constructed and arranged to releasably hold the humidifier lid when closed,*

*wherein the humidifier base is constructed and arranged to receive the water tank when the humidifier lid is open;*

*wherein, when the humidifier base receives the water tank, the heat conductive portion of the water tank is positioned relative to the humidifier heater plate to allow heat transfer communication therebetween in use;*

*wherein, when the continuous positive airway pressure device and the humidifier are latched together and the humidifier lid is closed with the water tank placed in the humidifier base, a sealed gas flow path is established, said sealed gas flow path extending from the continuous positive airway pressure device, through the humidifier base seal located between the humidifier base and a rear surface of the water tank, through an interior of the water tank, through the lid seal surrounding an outlet of the water tank lid and located on an underside of the humidifier lid, and to the air delivery pipe of the humidifier lid; and*

*wherein an engagement face of the continuous positive airway pressure device includes electrical connectors to deliver power to the humidifier heater plate.*

*27. The apparatus of claim 26, wherein the humidifier lid is constructed and arranged so that it is rotatable from a closed position to a maximum extent of normal travel in an open position, and wherein, upon further rotation of the humidifier lid beyond the maximum extent, the humidifier lid becomes removed from the humidifier base,*

*wherein the locking mechanism is configured to provide an audible "click" sound upon locking,*

*wherein the lid seal is a pressure-assisted seal,*

*wherein the humidifier base seal is a pressure-assisted seal,*

*wherein the humidifier base seal includes a connector portion and a peripheral seal to abut and seal against a flat surface radially surrounding an aperture of an inlet of the water tank, and*

*wherein the lid seal includes a sealing flange to abut and sealingly engage a surface radially surrounding an aperture of the outlet of the water tank lid.*

*28. The apparatus of claim 26, wherein the humidifier includes a pair of flat male blade connectors for engagement with mating connectors on the continuous positive airway pressure device.*

*29. The apparatus of claim 26, wherein the humidifier base and the water tank have complementary configurations to guide positioning of the water tank in the humidifier base.*

*30. The apparatus of claim 26 further comprising a controller and a sensor configured to automatically detect the presence of the humidifier and adjust an automatic control algorithm of the continuous positive airway pressure device when the continuous positive airway pressure device and the humidifier are connected.*

* * * * *